US009321796B2

(12) United States Patent
Elewaut et al.

(10) Patent No.: US 9,321,796 B2
(45) Date of Patent: Apr. 26, 2016

(54) GALACTOPYRANOSYL DERIVATIVES USEFUL AS MEDICAMENTS

(71) Applicant: Universiteit Gent, Ghent (BE)

(72) Inventors: Dirk Elewaut, Heusden (BE); Nora Pauwels, Mariakerke (BE); Sandrine Aspeslagh, Oostende (BE); Serge Van Calenbergh, De Pinte (BE)

(73) Assignee: Universiteit Gent, Ghent (BE)

( * ) Notice: Subject to any disclaimer, the term of this patent is extended or adjusted under 35 U.S.C. 154(b) by 0 days.

(21) Appl. No.: 14/411,413

(22) PCT Filed: Jun. 20, 2013

(86) PCT No.: PCT/EP2013/062941
§ 371 (c)(1),
(2) Date: Dec. 26, 2014

(87) PCT Pub. No.: WO2014/001204
PCT Pub. Date: Jan. 3, 2014

(65) Prior Publication Data
US 2015/0210728 A1    Jul. 30, 2015

Related U.S. Application Data

(60) Provisional application No. 61/665,730, filed on Jun. 28, 2012.

(51) Int. Cl.
*C07H 15/26* (2006.01)
*C07H 15/04* (2006.01)
*C07H 15/18* (2006.01)

(52) U.S. Cl.
CPC ............... *C07H 15/26* (2013.01); *C07H 15/04* (2013.01); *C07H 15/18* (2013.01)

(58) Field of Classification Search
None
See application file for complete search history.

(56) References Cited

U.S. PATENT DOCUMENTS

2009/0047299 A1    2/2009  Savage et al.
2012/0270815 A1   10/2012  Savage et al.

FOREIGN PATENT DOCUMENTS

| WO | WO-2004/094444 A1 | 11/2004 |
| WO | WO-2007/118234 A2 | 10/2007 |
| WO | WO-2007/118234 A3 | 10/2007 |

OTHER PUBLICATIONS

Jervis et al., Bioorganic and Medicinal Chemistry Letters, vol. 22(13), pp. 4348-4352, May 2, 2012.*
Jervis et al., "New CD1d agonists: synthesis and biological activity of 6"-triazole-substituted alpha-galactosyl ceramides," Bioorg. Med Chem Lett. 22(13):4348-52 (2012).
Pauwels et al., "Synthesis of 6"-triazole-substituted alpha-GalCer analogues as potent iNKT cell stimulating ligands," Bioorg Med Chem. 20(24):7149-54 (2012).
International Search Report for International Patent Application No. PCT/EP2013/062941, mailed Aug. 23, 2013 (4 pages).
Written Opinion of the International Searching Authority for International Patent Application No. PCT/EP2013/062941, mailed Aug. 23, 2013 (6 pages).

* cited by examiner

*Primary Examiner* — Traviss C McIntosh, III
(74) *Attorney, Agent, or Firm* — Clark & Elbing LLP

(57) ABSTRACT

This invention relates to carbamate-containing or thiocarbamate-containing galacto-pyranosyl compounds useful as therapeutic agents and being represented by the structural formula (II), wherein: X is O or S, R is selected from the group consisting of $C_{1-8}$ alkyl, $C_{3-10}$ cycloalkyl, aryl-$C_{1-4}$ alkyl, heterocyclyl-$C_{1-4}$ alkyl, cycloalkyl-$C_{1-4}$ alkyl, aryl and heterocyclyl, wherein R is optionally substituted with one or more $R_9$; $R_2$, $R_3$, $R_4$, $R_6$ and $R_7$ are independently selected from the group consisting of hydroxyl and protected hydroxyl groups; $R_5$ is selected from the group consisting $C_{6-30}$ alkyl and arylalkyl; $R_8$ is $C_{6-30}$ alkyl; and each $R_9$ is independently selected from the group consisting of halogen, hydroxy, trifluoromethyl, trifluoromethoxy, $C_{1-8}$alkoxy, $C_{1-6}$ alkyl, cyano, methylthio, phenyl, phenoxy, chloromethyl, dichloromethyl, chloro-difluoromethyl, acetyl, nitro, benzyl, heterocyclyl and di-$C_{1-4}$ alkyl-amino, or a pharmaceutically acceptable salt thereof.

14 Claims, 16 Drawing Sheets

α-GalCer (1): X = O, m = 13, n = 24
OCH (2): X = O, m = 4, n = 22
α-C-GalCer (3): X = CH$_2$, m = 13, n = 24

GALACTOPYRANOSYL DERIVATIVES USEFUL AS MEDICAMENTS

The present invention relates to a class of new glycolipids, in particular new galactopyranosyl derivatives, that exhibit biological activity and consequently are useful as active ingredients in the manufacture of medicaments. The present invention also relates to methods of treatment of proliferative disorders and auto-immune diseases wherein the biological profile of the new galactopyranosyl derivatives is capable of efficiently interacting with the causes and effects of such disorders. The present invention further relates to vaccines comprising said new galactopyranosyl derivatives as an adjuvant.

BACKGROUND OF THE INVENTION

During the past years the use of glycolipids as immunostimulating agents has become increasingly important, mainly due to their potential role in the defence against infections, tumour immune surveillance and auto-immunity. An extensively studied subset of T lymphocytes are natural killer T (NKT) cells, which express an invariant T cell antigen receptor (TCR). NKT cells are a subset of regulatory T cells that are involved in different pathological processes, ranging from autoimmunity to protection against tumors and bacterial infections. NKT cell activation results in immediate cytokine production (within several hours), cytotoxicity and proliferation, which subsequently activate several by-stander immune cells (NK cells, dendritic cells, B cells, etc.). Unlike other T cells, NKT cells recognize glycolipid antigens when presented by the major histocompatibility complex (MHC) class I-like molecule CD1d.

The most well studied CD1d-presented antigen that specifically activates invariant NKT (hereinafter iNKT) cells is α-galactosyl ceramide (α-GalCer, also known as KRN7000 and shown as 1 on top of FIG. 1). It resulted from the structural optimisation of a series of agelasphins, a family of α-linked glycosphingolipids isolated from *Agelas mauritianus*, a marine sponge from which extracts had demonstrated anti-tumour properties in murine models. α-GalCer consists of a galactosyl moiety α-linked to D-erythrophytosphingosine, which is N-acylated with a 26-carbons fatty acid.

α-GalCer has been proposed as a promising agent for the treatment of cancer, malaria, hepatitis B, certain bacterial infections and the suppression of auto-immune diseases. Its activity relies on the recognition of the CD1d-α-GalCer bimolecular complex. Upon this recognition, NKT cells are activated, resulting in the rapid release of T helper 1 (Th1) and T helper 2 (Th2) cytokines. Secondary activation of other cell types include NK cells, B cells, CD8+ T cells, dendritic cells, and myeloid cells as well as the differentiation of CD4+ T cells into either Th1 or Th2 cells. This ability to influence both innate and adaptive immune responses puts NKT cells in the position to play a pivotal role in regulating immune responses in both host defence and autoimmune diseases.

Th1 cytokines, such as IFN-γ, are stimuli which drive the development of naive helper T cells toward Th1 type cell formation. In contrast, Th2 cytokines like IL-4 send pre-Th cells down the path of Th2 type cell formation. Th1 cells participate in cell-mediated immunity and are essential for controlling intracellular pathogens, while Th2 cells participate in antibody-mediated immunity control of extra-cellular pathogens. The balance between Th1 and Th2 cytokines is carefully controlled and any disruption between the two can cause disease. Therapeutic strategies could involve trying to restore Th1/Th2 balance through in vivo modulation of NKT cells. While certain auto-immune diseases are characteristic of hypo-responsiveness to Th2 and over-activation of Th1 cells, the opposite is true for many types of cancer that have a predominant Th2 response. Th1 cytokines are thought to mediate the anti-tumour, antiviral, and antibacterial effects of α-GalCer. In a Phase I study, α-GalCer was ineffective in the treatment of solid tumours possibly because the therapeutic effects of IFN-γ were hindered by IL-4 giving no net benefit. Skewing of the cytokine release profile to Th1 would be beneficial for the treatment of these diseases and, therefore, the development of α-GalCer analogues capable to induce a biased Th1 response while maintaining α-GalCer's antigenic potency are highly awaited.

Although initially iNKT cell research was mainly focused on this antigen, the list of novel glycolipids that are able to induce iNKT cell activation is continuously growing and includes very diverse bacterial antigens and endogenously expressed glycolipids, in addition to newly synthesized antigens. Attempts to selectively control the rapid secretion of cytokines by NKT cells have led to the development of several α-GalCer analogues with immunomodulatory properties, as shown on FIG. 10.

The iNKT cell T-cell receptor is semi-invariant as it contains a conserved Vα14 chain in mice and Vα24 in human, while the Vβ chain is more variable. However, only germline encoded residues are important for the recognition of a glycolipid. Although the T-cell receptor plays an important role for initial recognition of the CD1d-glycolipid complex, the strength of a Th1 polarized iNKT cell dependent activation seems to be more determined by the stability of the CD1d-glycolipid complex. Most analogues capable to induce a polarised response reported so far originate from modifications of the hydrophobic chains of α-GalCer. With the synthesis of OCH (structure shown in FIG. 10), an α-GalCer analogue with truncated sphingosine and fatty acyl chains, a direct relationship has been shown relating the shortening of lipid tail lengths and biasing of the cytokine release profile toward a Th2 response. Likewise, it was reported that substituting the N-acyl chain of α-GalCer with shorter, unsaturated fatty acids modifies the outcome of Vα14i NKT cell activation. Analogues containing multiple cis-double bonds in the acyl chain (e.g. shown as 4 in FIG. 10) potently induced a T helper type 2-biased cytokine response, with diminished IFN-γ production and reduced Vα14i NKT cell expansion. Conversely, it has been found that introducing terminal aromatic groups into the fatty acyl tail of α-GalCer (such as in compound 5 of FIG. 10) enhances stability of the glycolipid/CD1d complex and biases the profile toward a Th1 response.

Characterised by an enhanced Th1 response, α-C-GalCer (shown as compound 3 in FIG. 10) exhibits 100- to 1000-fold improved activity against melanoma metastases and malaria compared with α-GalCer. Both are diseases where a Th1 response is beneficial. In this analogue, the O linkage between the sugar and ceramide is replaced with a C-linkage giving the glycosidic bond in vivo stability to enzymatic degradation. It is unclear to what extent the enhanced stability of this compound accounts for its superior in vivo activity. Likewise, a protective effect of OCH was found on Th1-mediated auto-immune diseases, such as collagen-induced arthritis (CIA) and experimental auto-immune encephalomyelitis (EAE) in mice. Recently it was demonstrated that in vivo neutralisation of IFN-γ release induced by α-GalCer early during the course of disease resulted in partial improvement of clinical arthritis symptoms, further indicating the importance of a skewed cytokine profile on the therapeutical outcome.

In 2005, the crystal structure of human CD1d complexed with α-GalCer was elucidated and unravelled the specific binding mode of α-GalCer to CD1 d. The acyl chain of α-GalCer fits into the A' pocket by adopting a counter-clockwise circular curve, while the sphingosine chain adopts an extended conformation to fit into the F' pocket and to reach the end of the binding groove. The galactose ring is well ordered and extends above the surface of the lipid-binding groove. The crystal structure revealed three hydrogen bonds between human CD1d and α-GalCer. The glycosidic linkage 1"-O is hydrogen-bonded to Thr-154, the 2"-OH of the galactose ring forms a hydrogen bond to Asp-151 and the 3-OH of the sphingosine moiety forms the third hydrogen bond to Asp-80. These bonds are assumed to anchor α-GalCer in a proper orientation for recognition by the T-cell receptor of NKT cells.

Previously the naphthylurea derivative NU-α-GalCer was shown to induce a structural change within the A' roof of CD1d to which it binds with its hydrophobic 6"-naphthylurea group, leading to the so called third anchor model. Data suggested that the formation of an extra anchor leads to stronger anti-tumoral responses in vivo. However, the Th1 polarizing strength seemed to be critically dependent on the nature and length of the linker between C-6" of the galactose and the aromatic groups. BnNH-GSL-1', an analogue characterized by an aromatic moiety located one atom closer to the galactose ring, was shown to affect T-cell receptor affinity and decreased antigenicity despite the fact that its amide linker, just like the urea linker of NU-α-GalCer, forms an additional H-bond with CD1d.

Extra binding strength of a glycolipid can also be achieved through alterations of the lipid tails. The altered sphingosine chain of a plakoside analogue was shown to increase the contact surface area with CD1d within the F'-pocket. Additionally it was shown that several acyl chain altered glycolipids can induce superior anti-cancer effects compared to α-GalCer and this was also linked to increased CD1d avidity. Last but not least crystallographic analysis of iGb3, a beta-anomeric tri-hexose containing sphingolipid self-antigen, demonstrated that the T-cell receptor was able to bind to the CD1d-glycolipid complex with its conserved footprint. This mechanism induces the last anchor sugar to bind to CD1d, however this does not happen to Gb3, which only differs by an altered linkage of the last sugar, because Gb3 was not able to form this additional anchor to CD1d.

Recently the structure of a human NKT T-cell receptor in complex with CD1d bound to α-GalCer was reported. Consistent with the previously proposed structures, α-GalCer protrudes minimally from the CD1d cleft with only the galactosyl head group exposed for recognition by the NKT T-cell receptor, interacting solely with the CDR1α and CDR3α loops. The galactose ring is sandwiched between Trp-153 of CD1d and the aliphatic moiety of Arg-95α, the side chain of which also hydrogen bonds to the 3-OH on the sphingosine chain. The 2'-OH, 3'-OH and 4'-OH of the galactose ring form hydrogen bonds to Gly-96α, Ser-30α and Phe-29α, respectively, located on the invariant TCR α-chain. This mode of binding is consistent with the specificity the NKT TCR exhibits for α-GalCer and closely related analogues.

The issue of galactosylceramide therapy for auto-immune diseases has been discussed extensively by L. Van Kaer in *Nature Reviews* (2005) 5:31-42 and references cited therein, the content of which is incorporated herein by reference. Other biological and synthetic issues in respect of certain galactosylceramides have also been disclosed by Kratzer et al in *Eur. J. Org. Chem*. (1998) 291-298; Zhou et al in *Org. Lett.* (2002) 4:1267-1270; Yang et al in *Angew. Chem. Intl. Ed.* (2004) 43:3818-3822; azido and arylurea derivatives of α-GalCer in Trappeniers et al, *J. Am. Chem. Soc.* (2008) 130:16468-9; and Trappeniers et al in *Org. Lett.* (2010) 12:2928-2931, the content of which is incorporated herein by reference.

WO 2004/094444 discloses a 6-substituted amino-6-deoxy-galactosylceramide derivative with NKT cell stimulating activity. WO 2007/118234 also discloses a 6-acylamino derivative for staining and stimulating natural killer T cells.

However none of these galactopyranosyl derivatives has been shown to exhibit both the strong biological activity and the safety/release profile that can make them an acceptable drug to be made commercially available for the treatment of diseases.

Accordingly there is still a need in the art for alternative α-GalCer analogues exhibiting enhanced biological activities, enhanced drug formulation capabilities, and improved safety profile.

There is also a regular need in the art for novel compounds acting as anti-cancer agents that can be used, alone or in combination with another form or therapeutic treatment, for treating various forms of cancer.

There is also a regular need in the art for novel compounds having significant and specific anti-parasitic or anti-infectious properties without having the drawbacks of known effective anti-parasitic agents. There is a regular need in the art for effective anti-parasitic or anti-infectious agents having improved metabolisation and/or pharmacokinetic behaviour and which therefore can be more easily formulated into effective dosage forms. There is also a need in the art for such novel compounds exhibiting a longer plasma half-life and a significantly improved resorption rate. There is also a regular need in the art for novel specific and highly therapeutically active compounds having significant immuno-modulating or immunosuppressive activity, such as, but not limited to, drugs for treating immune or autoimmune disorders, and organ and cells transplant rejections

SUMMARY OF THE INVENTION

In order to further explore the relationship between structure of 6"-substituted α-GalCer analogues and Th1 biased activity we investigated and herein report the preparation and biological evaluation of a series of novel carbamate, thiocarbamate and triazolyl derivatives of α-GalCer, which are synthetically more easily accessible than NU-α-GalCer. Similarly to NU-α-GalCer, these glycolipids showed an increased stability to CD1d compared to α-GalCer, without significantly affecting TCR affinity. Surprisingly, certain carbamate thiocarbamate and triazolyl analogues exhibit highly increased Th1 potency, which is linked to a tenfold increase in IL-12 production compared to α-GalCer. This strong Th1 response led to superior tumor responses compared to NU-α-GalCer. Interestingly, these 6"-carbamate, thiocarbamate and triazolyl analogues are also able to stimulate human iNKT cells, which stands as an important benefit over α-C-GalCer, the prototypical Th1-skewing analogue. In conclusion, these data solidify the in vivo relevance of the additional anchor model and demonstrate that the introduction of aromatic or heterocyclic (preferably hetero-aromatic) moieties to the 6" position of the sugar via judiciously chosen linkers is a promising strategy to generate strong Th1 polarizing glycolipids.

Thus the present invention is based on the unexpected finding that certain galactopyranosyl derivatives with a specific substituting pattern including a carbamate, thiocarbamate or triazolyl moiety exhibit enhanced biological activities, enhanced drug formulation capabilities, and improved safety profile with respect to α-GalCer and existing α-GalCer analogues. Such galactopyranosyl derivatives are defined in claim 1, and medicaments including them are defined in claim.

Definitions

As used herein with respect to a substituent, and unless otherwise stated, the term "$C_{1-6}$ alkyl" means straight and branched chain saturated acyclic (aliphatic) hydrocarbon monovalent groups having from 1 to 6 carbon atoms such as, for example, methyl, ethyl, propyl, n-butyl, 1-methylethyl (isopropyl), 2-methylpropyl (isobutyl), 1,1-dimethylethyl (tert-butyl), 2-methyl-butyl, n-pentyl, dimethylpropyl, n-hexyl, 2-methylpentyl, 3-methylpentyl, and the like. By analogy, the term "$C_{1-4}$ alkyl" refers to such groups having from 1 to 4 carbon atoms, and the term "$C_{6-30}$ alkyl" refers to such groups having from 6 to 30 carbon atoms, including n-octyl, n-nonyl, n-decyl, n-undecyl, n-dodecyl, n-tridecyl, n-tetradecyl, n-pentadecyl, n-hexadecyl, n-heptadecyl, n-octadecyl, n-nonadecyl, and the like.

As used herein with respect to a substituent, and unless otherwise stated, the term "acyl" broadly refers to a group derived from an acid such as an organic monocarboxylic acid, a carbonic acid, a carbamic acid (resulting into a carbamoyl substituent) or the thioacid or imidic acid (resulting into a carbamidoyl substituent) corresponding to said acids, and the term "sulfonyl" refers to a group derived from an organic sulfonic acid, wherein said acids comprise an aliphatic, aromatic (aryl) or heterocyclic moiety (as defined herein) in the molecule. A more specific kind of "acyl" group within the scope of the above definition refers to a carbonyl (oxo) group adjacent to a $C_{1-6}$ alkyl, a $C_{3-10}$ cycloalkyl, an aryl, an arylalkyl or a heterocyclyl group, all of them being such as herein defined. Acyl and sulfonyl groups originating from aliphatic or cycloaliphatic monocarboxylic acids or sulphonic acids, are designated herein as aliphatic or cycloaliphatic acyl and sulfonyl groups and include, but are not limited to, the following:

alkanoyl (for example formyl, acetyl, propionyl, butyryl, isobutyryl, valeryl, isovaleryl, pivaloyl and the like);

cycloalkanoyl (for example cyclobutanecarbonyl, cyclopentanecarbonyl, cyclo-hexanecarbonyl, 1-adamantanecarbonyl and the like);

cycloalkyl-alkanoyl (for example cyclohexylacetyl, cyclopentylacetyl and the like);

alkenoyl (for example acryloyl, methacryloyl, crotonoyl and the like);

alkylthioalkanoyl (for example methylthioacetyl, ethylthioacetyl and the like);

alkanesulfonyl (for example mesyl, ethanesulfonyl, propanesulfonyl and the like);

alkoxycarbonyl (for example methoxycarbonyl, ethoxycarbonyl, propoxycarbonyl, isopropoxycarbonyl, butoxycarbonyl, isobutoxycarbonyl and the like);

alkylcarbamoyl (for example methylcarbamoyl and the like);

(N-alkyl)-thiocarbamoyl (for example (N-methyl)-thiocarbamoyl and the like);

alkylcarbamidoyl (for example methylcarbamidoyl and the like); and alkoxyalkyl (for example methoxyalkyl, ethoxyalkyl, propoxyalkyl and the like);

Acyl and sulfonyl groups may also originate from aromatic monocarboxylic acids or sulphonic acids, and include, but are not limited to, the following:

aroyl (for example benzoyl, toluoyl, xyloyl, 1-naphthoyl, 2-naphthoyl and the like);

arylalkanoyl (for example phenylacetyl and the like);

arylalkenoyl (for example cinnamoyl and the like);

aryloxyalkanoyl (for example phenoxyacetyl and the like);

arylthioalkanoyl (for example phenylthioacetyl and the like);

arylaminoalkanoyl (for example N-phenylglycyl, and the like);

arylsulfonyl (for example benzenesulfonyl, toluenesulfonyl, naphthalene sulfonyl and the like);

aryloxycarbonyl (for example phenoxycarbonyl, naphthyloxycarbonyl and the like);

arylalkoxycarbonyl (for example benzyloxycarbonyl and the like);

arylcarbamoyl (for example phenylcarbamoyl, naphthylcarbamoyl and the like);

arylglyoxyloyl (for example phenylglyoxyloyl and the like).

arylthiocarbamoyl (for example phenylthiocarbamoyl and the like); and arylcarbamidoyl (for example phenylcarbamidoyl and the like).

Acyl groups may also originate from heterocyclic monocarboxylic acids or sulphonic acids, and include, but are not limited to, the following:

heterocyclic-carbonyl, in which said heterocyclic group is as defined herein, preferably an aromatic or non-aromatic 5- to 7-membered heterocyclic ring with one or more heteroatoms selected from the group consisting of nitrogen, oxygen and sulfur in said ring (for example thiophenecarbonyl, furoyl, pyrrolecarbonyl, nicotinoyl and the like); and heterocyclyl-alkanoyl in which said heterocyclyl group is as defined herein, preferably an aromatic or non-aromatic 5- to 7-membered heterocyclic ring with one or more heteroatoms selected from the group consisting of nitrogen, oxygen and sulfur in said ring (for example thiopheneacetyl, furylacetyl, imidazolylpropionyl, tetrazolylacetyl, 2-(2-amino-4-thiazolyl)-2-methoxyiminoacetyl and the like).

As used herein with respect to a substituent, and unless otherwise stated, the term "$C_{3-10}$ cycloalkyl" means a mono- or polycyclic saturated hydrocarbon monovalent group having from 3 to 10 carbon atoms, such as for instance cyclopropyl, cyclobutyl, cyclopentyl, cyclohexyl, cycloheptyl, cyclooctyl and the like, or a $C_{7-10}$ polycyclic saturated hydrocarbon monovalent radical having from 7 to 10 carbon atoms such as, for instance, norbornyl, fenchyl, trimethyltricycloheptyl or adamantyl.

As used herein with respect to a substituent, and unless otherwise stated, the term "aryl" designates any mono- or polycyclic aromatic monovalent hydrocarbon group having from 6 up to 30 carbon atoms such as but not limited to phenyl, naphthyl, anthracenyl, phenanthracyl, fluoranthenyl, chrysenyl, pyrenyl, biphenylyl, terphenyl, picenyl, indenyl, biphenyl, indacenyl, benzocyclobutenyl and benzocyclooctenyl, also including fused benzo-$C_{4-8}$ cycloalkyl groups (the latter being as defined above) such as, for instance, indanyl, tetrahydronaphthyl, fluorenyl and the like, including (where applicable) any isomeric form thereof, all of the said groups being optionally substituted, in any isomeric position of the aromatic ring, with one or more substituents independently selected from the group consisting of halogen, amino, trifluoromethyl, trifluoromethoxy, hydroxyl, $C_{1-4}$ alkyl, $C_{1-4}$ alkoxy and nitro, such as for instance 4-fluorophenyl, 4-chlorophenyl, 3,4-dichlorophenyl, 4-cyanophenyl, 2,6-dichlorophenyl, 2-fluorophenyl, 3-chlorophenyl, 3,5-dichlorophenyl and the like.

As used herein with respect to a substituent, and unless otherwise stated, the term "heterocyclyl" refers to a mono- or polycyclic, saturated or mono-unsaturated or polyunsaturated monovalent hydrocarbon group having from 2 up to 15 carbon atoms and including one or more heteroatoms in one or more heterocyclic rings, each of said rings having from 3 to 10 atoms (and optionally further including one or more heteroatoms attached to one or more carbon atoms of said ring, for instance in the form of a carbonyl or thiocarbonyl or selenocarbonyl group, and/or to one or more heteroatoms of said ring, for instance in the form of a sulfone, sulfoxide, N-oxide, phosphate, phosphonate or selenium oxide group), each of said heteroatoms being independently selected from the group consisting of nitrogen, oxygen, sulfur, selenium and phosphorus, also including groups wherein a heterocyclic ring is fused to one or more aromatic hydrocarbon rings for instance in the form of benzo-fused, dibenzo-fused and naphtho-fused heterocyclic groups; within this definition are included heterocyclic groups such as, but not limited to, diazepinyl, oxadiazinyl, thiadiazinyl, dithiazinyl, triazolonyl, diazepinonyl, triazepinyl, triazepinonyl, tetrazepinonyl, benzoquinolinyl, benzothiazinyl, benzothiazinonyl, benzoxathiinyl, benzodioxinyl, benzodithiinyl, benzoxazepinyl, benzothiazepinyl, benzodiazepinyl, benzodioxepinyl, benzodithiepinyl, benzoxazocinyl, benzo-thiazocinyl, benzodiazocinyl, benzoxathiocinyl, benzodioxocinyl, benzotrioxepinyl, benzoxathiazepinyl, benzoxadiazepinyl, benzothia-diazepinyl, benzotriazepinyl, benzoxathiepinyl, benzotriazinonyl, benzoxazolinonyl, azetidinonyl, azaspiroundecyl, dithiaspirodecyl, selenazinyl, selenazolyl, selenophenyl, hypoxanthinyl, azahypo-xanthinyl, bipyrazinyl, bipyridinyl, oxazolidinyl, diselenopyrimidinyl, benzodioxocinyl, benzopyrenyl, benzopyranonyl, benzophenazinyl, benzoquinolizinyl, dibenzo-carbazolyl, dibenzoacridinyl, dibenzophenazinyl, dibenzothiepinyl, dibenzoxepinyl, dibenzopyranonyl, dibenzoquinoxalinyl, dibenzothiazepinyl, dibenzisoquinolinyl, tetraazaadamantyl, thiatetraazaadamantyl, oxauracil, oxazinyl, dibenzothiophenyl, dibenzofuranyl, oxazolinyl, oxazolonyl, azaindolyl, azolonyl, thiazolinyl, thiazolonyl, thiazolidinyl, thiazanyl, pyrimidonyl, thiopyrimidonyl, thiamorpholinyl, azlactonyl, naphthindazolyl, naphthindolyl, naphthothiazolyl, naphthothioxolyl, naphthoxindolyl, naphthotriazolyl, naphthopyranyl, oxabicycloheptyl, azabenzimidazolyl, azacycloheptyl, azacyclooctyl, azacyclononyl, azabicyclononyl, tetrahydrofuryl, tetrahydropyranyl, tetrahydropyronyl, tetrahydroquinoleinyl, tetrahydrothienyl and dioxide thereof, dihydrothienyl dioxide, dioxindolyl, dioxinyl, dioxenyl, dioxazinyl, thioxanyl, thioxolyl, thiourazolyl, thiotriazolyl, thiopyranyl, thiopyronyl, coumarinyl, quinoleinyl, oxyquinoleinyl, quinuclidinyl, xanthinyl, dihydropyranyl, benzodihydrofuryl, benzothiopyronyl, benzothiopyranyl, benzoxazinyl, benzoxazolyl, benzodioxolyl, benzodioxanyl, benzothiadiazolyl, benzotriazinyl, benzothiazolyl, benzoxazolyl, phenothioxinyl, phenothiazolyl, phenothienyl (benzothiofuranyl), phenopyronyl, phenoxazolyl, pyridinyl, dihydropyridinyl, tetrahydropyridinyl, piperidinyl, morpholinyl, thiomorpholinyl, pyrazinyl, pyrimidinyl, pyridazinyl, triazinyl, tetrazinyl, triazolyl, benzotriazolyl, tetrazolyl, imidazolyl, pyrazolyl, thiazolyl, thiadiazolyl, isothiazolyl, oxazolyl, oxadiazolyl, pyrrolyl, furyl, dihydrofuryl, furoyl, hydantoinyl, dioxolanyl, dioxolyl, dithianyl, dithienyl, dithiinyl, thienyl, indolyl, indazolyl, benzofuryl, quinolyl, quinazolinyl, quinoxalinyl, carbazolyl, phenoxazinyl, phenothiazinyl, xanthenyl, purinyl, benzothienyl, naphtothienyl, thianthrenyl, pyranyl, pyronyl, benzopyronyl, isobenzofuranyl, chromenyl, phenoxathiinyl, indolizinyl, quinolizinyl, isoquinolyl, phthalazinyl, naphthiridinyl, cinnolinyl, pteridinyl, carbolinyl, acridinyl, perimidinyl, phenanthrolinyl, phenazinyl, phenothiazinyl, imidazolinyl, imidazolidinyl, benzimi-dazolyl, pyrazolinyl, pyrazolidinyl, pyrrolinyl, pyrrolidinyl, piperazinyl, uridinyl, thymidinyl, cytidinyl, azirinyl, aziridinyl, diazirinyl, diaziridinyl, oxiranyl, oxaziridinyl, dioxiranyl, thiiranyl, azetyl, dihydroazetyl, azetidinyl, oxetyl, oxetanyl, oxetanonyl, homopiperazinyl, homopiperidinyl, thietyl, thietanyl, diazabicyclooctyl, diazetyl, diaziridinonyl, diaziridinethionyl, chromanyl, chromanonyl, thiochromanyl, thiochromanonyl, thiochromenyl, benzofuranyl, benzisothiazolyl, benzocarbazolyl, benzochromonyl, benzisoalloxazinyl, benzocoumarinyl, thiocoumarinyl, pheno-metoxazinyl, phenoparoxazinyl, phentriazinyl, thiodiazinyl, thiodiazolyl, indoxyl, thioindoxyl, benzodiazinyl (e.g. phthalazinyl), phthalidyl, phthalimidinyl, phthalazonyl, alloxazinyl, dibenzopyronyl (i.e. xanthonyl), xanthionyl, isatyl, isopyrazolyl, isopyrazolonyl, urazolyl, urazinyl, uretinyl, uretidinyl, succinyl, succinimido, benzylsultimyl, benzylsultamyl and the like, including all possible isomeric forms thereof; depending upon the number of unsaturations in the 3 to 10 atoms ring, heterocyclic groups are conventionally subdivided into heteroaromatic (or "heteroaryl", i.e. fully unsaturated) groups and non-aromatic heterocyclic groups.

As used herein with respect to a substituent, and unless otherwise stated, the terms "$C_{1-6}$ alkoxy", "$C_{3-10}$ cycloalkoxy" and "heterocyclyloxy" refer to substituents wherein a carbon atom of a $C_{1-6}$ alkyl, $C_{3-10}$ cycloalkyl or heterocyclyl radical (each of them such as defined herein), is attached to an oxygen atom through a single bond such as, but not limited to, methoxy, ethoxy, propoxy, butoxy, pentoxy, isopropoxy, sec-butoxy, tert-butoxy, isopentoxy, cyclopropoxy, cyclobutoxy, cyclopentoxy, cyclohexyloxy, cycloheptyloxy, cyclooctyloxy, and various isomers of piperidinoxy, methylpiperidinoxy, pyrrolidinoxy, pyridinoxy, tetrahydrofuranyloxy, and the like.

As used herein with respect to a substituent, and unless otherwise stated, the term halogen means any atom selected from the group consisting of fluorine, chlorine, bromine and iodine. As used herein with respect to a substituent, and unless otherwise stated, the term "arylalkyl" refers to an aliphatic saturated hydrocarbon monovalent group (preferably a $C_{1-4}$ alkyl group such as defined above) onto which an aryl group (such as defined above) is attached via a carbon atom, and wherein the said aliphatic group and/or the said aryl group may be optionally substituted with one or more substituents independently selected from the group consisting of halogen, amino, hydroxyl, trifluoromethyl, trifluoromethoxy and nitro, such as but not limited to benzyl, 4-chlorobenzyl, 4-fluorobenzyl, 2-fluorobenzyl, 3,4-dichlorobenzyl, 2,6-dichlorobenzyl, 3-methylbenzyl, 4-methylbenzyl, 4-ter-butylbenzyl, phenylpropyl, 1-naphthylmethyl, phenylethyl, 1-amino-2-phenylethyl, 1-amino-2-[4-hydroxy-phenyl]ethyl, and the like.

As used herein with respect to a substituent, and unless otherwise stated, the term "heterocyclylalkyl" refers to an aliphatic saturated hydrocarbon monovalent group (preferably a $C_{1-4}$ alkyl group such as defined above) onto which a heterocyclyl group (such as defined above) is attached via a carbon atom, and wherein the said aliphatic group and/or the said heterocyclyl group may be optionally substituted with one or more substituents independently selected as defined hereinabove.

As used herein with respect to a substituent of a phenyl group, and unless otherwise stated, the terms "meta substituent", "ortho substituent" and "para substituent" refer to the meta, ortho and para substituting positions respectively with respect to the point of attachment of said phenyl onto the molecule core.

As used herein and unless otherwise stated, the term "stereochemical isomeric form" refers to all possible different isomeric as well as conformational forms which the compounds of this invention may possess, in particular all possible stereochemically and conformationally isomeric forms, all diastereomers, enantiomers and/or conformers of the basic molecular structure.

As used herein and unless otherwise stated, the term "enantiomer" means each individual optically active form of a compound of the invention, having an optical purity or enantiomeric excess (as determined by methods standard in the art) of at least 80% (i.e. at least 90% of one enantiomer and at most 10% of the other enantiomer), preferably at least 90% and more preferably at least 98%.

As used herein and unless otherwise stated, the term "solvate" includes any combination which may be formed by a derivative of this invention with a suitable inorganic solvent (e.g. water forming hydrates) or organic solvent such as, but not limited to, alcohols (thus forming alcoholates), ketones, esters, ethers, nitriles and the like.

DETAILED DESCRIPTION OF THE INVENTION

Figure 1:
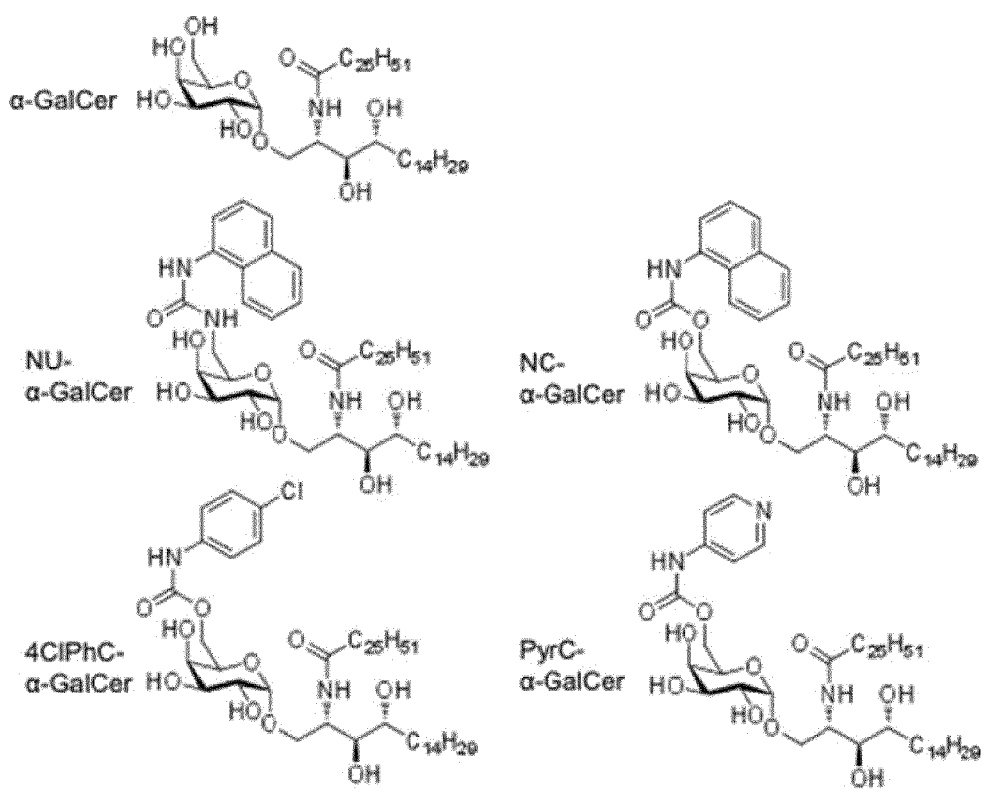
FIG. 1 shows the structural formulae of three representative galactopyranosyl compounds of the present invention (NC-α-GalCer, 4ClPhC-α-GalCer, and PyrC-α-GalCer) as well as α-GalCer itself and its naphthylurea derivative NU-α-GalCer, together with their Th1-Th2 profile manifested by serum levels of IFN-γ and IL-12 at 16 hours after injection of 5 μg glycolipid.
Figure 1:
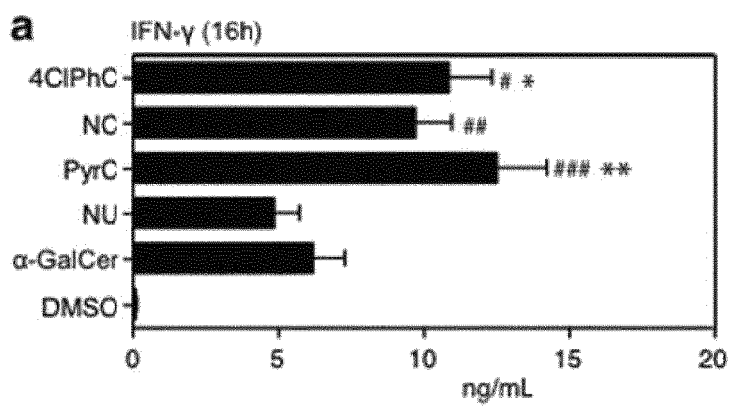
Figure 1:
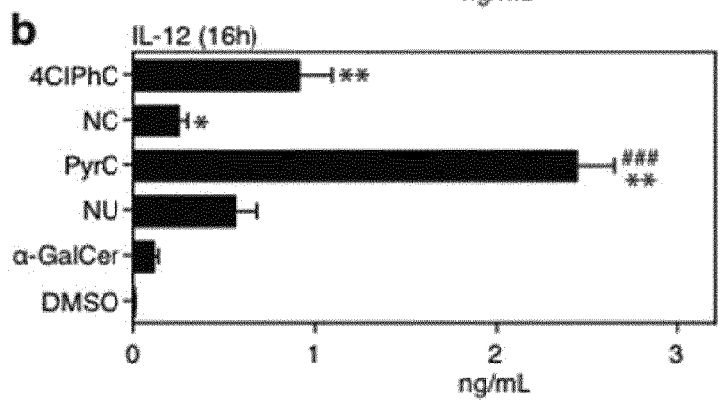

One embodiment of the present invention relates to carbamate-containing galactopyranosyl compounds represented by the structural formula (1):

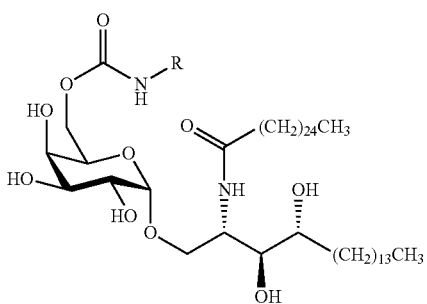

wherein R is selected from the group consisting of $C_{1-8}$ alkyl, $C_{3-10}$ cycloalkyl, aryl-$C_{1-4}$ alkyl, heterocyclyl-$C_{1-4}$ alkyl, cycloalkyl-$C_{1-4}$ alkyl, aryl and heterocyclyl (for instance heteroaryl) as defined hereinabove.

A more specific embodiment of the present invention relates to galactopyranosyl compounds represented by the structural formula (I) wherein R is 4-chlorophenyl, naphth-1-yl and 4-pyridyl. Another embodiment of the present invention relates to galactopyranosyl compounds represented by the structural formula (I) wherein R is not 4-chlorophenyl, naphth-1-yl or 4-pyridyl.

Although the structural formula (I) shows compounds with $C_{25}$ and $C_{14}$ alkyl groups in the respective lipid chains, the present invention is not limited thereto, but these chains may each have a $C_{6-30}$ alkyl terminal group. Although the structural formula (I) shows compounds with three hydroxyl groups on the pyranosyl ring, the present invention is not limited thereto, but each one of said hydroxyl groups may be independently replaced, especially as a precursor in an intermediate synthetic step, with a hydroxyl-protecting group such as, but not limited to, benzyloxy or acyloxy (wherein acyl is as defined hereinabove). Although the structural formula (I) shows compounds with two hydroxyl groups on a lipid chain, the present invention is not limited thereto, but each one of said hydroxyl groups may be independently replaced, especially as a precursor in an intermediate synthetic step, with a hydroxyl-protecting group such as, but not limited to, benzyloxy or acyloxy (wherein acyl is as defined hereinabove).

Although the structural formula (I) shows a carbamate group C(=O)NHR, the present invention is not limited thereto, and a corresponding thiocarbamate group C(=S)NHR wherein R is as defined above is intended as well.

Thus according to a first broad aspect, the present invention relates to a class of carbamate-containing and thiocarbamate-containing galacto-pyranosyl compounds represented by the structural formula (II):

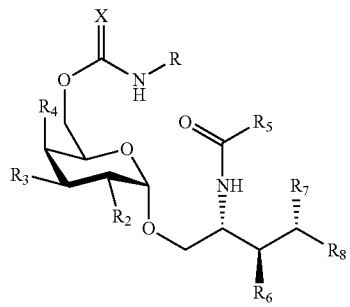

wherein:

X is O or S,

R is selected from the group consisting of $C_{1-8}$ alkyl, $C_{3-10}$ cycloalkyl, aryl-$C_{1-4}$ alkyl, heterocyclyl-$C_{1-4}$ alkyl, cycloalkyl-$C_{1-4}$ alkyl, aryl and heterocyclyl (e.g. heteroaryl), wherein R is optionally substituted with one or more $R_9$;

$R_2$, $R_3$, $R_4$, $R_6$ and $R_7$ are independently selected from the group consisting of hydroxyl and protected hydroxyl groups;

$R_5$ is selected from the group consisting $C_{6-30}$ alkyl and arylalkyl;

$R_8$ is $C_{6-30}$ alkyl; and each $R_9$ is independently selected from the group consisting of halogen, hydroxy, trifluoromethyl, trifluoromethoxy, $C_{1-8}$ alkoxy, $C_{1-6}$ alkyl, cyano, methylthio, phenyl, phenoxy, chloromethyl, dichloromethyl, chloro-difluoromethyl, acetyl, nitro, benzyl, heterocyclyl and di-$C_{1-4}$ alkyl-amino.

The above class of carbamate-containing and thiocarbamate-containing galactopyranosyl compounds of the present invention may be sub-divided into sub-groups each representing useful particular embodiments of the invention, such as but not limited to:

compounds wherein $R_2$, $R_3$, $R_4$, $R_6$ and $R_7$ are benzyloxy;

compounds wherein R is phenyl substituted with one $R_9$;

compounds wherein R is phenyl substituted with one $R_9$ and wherein this $R_9$ is a para-substituent;

compounds wherein R is phenyl substituted with two $R_9$;

compounds wherein R is phenyl substituted with two $R_9$ and wherein at least one of these $R_9$ is a meta-substituent;

compounds wherein R is phenyl substituted with two $R_9$ and wherein one of these $R_9$ is a para-substituent;

compounds wherein R is naphth-1-yl or naphth-2-yl;

compounds wherein R is a heterocyclyl group with 6 atoms in the ring system;

compounds wherein R is a heterocyclyl group with 5 atoms in the ring system;

compounds wherein R is selected from the group consisting of pyrid-4-yl, pyrid-3-yl, pyrid-2-yl, pyrazinyl, pyrimidin-2-yl, pyrimidin-4-yl, pyrimidin-5-yl and pyrimidin-6-yl;

compounds wherein R is phenyl substituted with three $R_9$;

compounds wherein R is phenyl substituted with three $R_9$ and wherein at least one of these $R_9$ is an ortho-substituent;

compounds wherein R is phenyl substituted with three $R_9$; and wherein one of these $R_9$ is a para-substituent;

compounds wherein R is a saturated heterocyclyl group including one nitrogen atom and said R is optionally substituted with benzyl;

compounds wherein R is a saturated heterocyclyl group including one nitrogen atom and one oxygen atom;

compounds wherein R is a heteroaryl group including one nitrogen atom; and compounds wherein R is a $C_{1-4}$ alkyl group substituted, preferably at the terminal end, with a di-$C_{1-4}$ alkylamino group, e.g. a dimethylamino or diethylamino group.

Another embodiment of the present invention relates to a class of triazolyl-containing galactopyranosyl compounds represented by the structural formula (III):

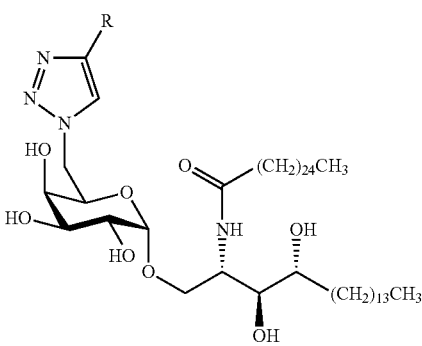

wherein the R substituent of the triazolyl ring is selected from the group consisting of hydrogen, $C_{1-6}$ alkyl, $C_{1-4}$ alkoxy-$C_{1-4}$ alkyl, $C_{1-4}$ alkylcarbonyl, aryl, aryl-$C_{1-3}$ alkyl and heterocyclyl (preferably heteroaryl) as defined hereinabove, i.e. including possible substitutions with amino, halogen, dimethylamino or $C_{1-4}$ alkoxy onto the aryl or heterocyclyl ring, wherein each of the $(CH_2)_{24}CH_3$ and $(CH_2)_{13}CH_3$ groups may independently be replaced with a $C_{6-30}$ alkyl group, and wherein each hydroxyl group on the pyranosyl ring or the lipid chain may independently be replaced with a hydroxyl-protecting group, or a pharmaceutically acceptable salt thereof.

A more specific embodiment of the present invention relates to triazolyl-containing galactopyranosyl compounds represented by the structural formula (III) wherein R is selected from the group consisting of propyl, phenyl, benzyl and phenethyl. Another embodiment of the present invention relates to triazolyl-containing galactopyranosyl compounds represented by the structural formula (III) wherein R is not selected from the group consisting of propyl, phenyl, benzyl, phenethyl, ethylcarbonyl and methoxymethyl. Another specific embodiment of the present invention relates to triazolyl-containing galactopyranosyl compounds represented by the structural formula (III) wherein each of the $(CH_2)_{24}CH_3$ and $(CH_2)_{13}CH_3$ groups on the lipid chain is replaced with a $C_{6-30}$ alkyl group and R is in accordance with the broad definition of formula (III). Another specific embodiment of the present invention relates to triazolyl-containing galactopyranosyl compounds represented by the structural formula (III) wherein at least one hydroxyl group on the pyranosyl ring or the lipid chain is replaced with a hydroxyl-protecting group such as a benzyloxy group. Each of the above recited specific embodiments of the present invention may be combined if desired.

Although the structural formula (III) shows compounds with $C_{25}$ and $C_{14}$ alkyl groups in the respective lipid chains, the present invention is not limited thereto, but these chains may each have a $C_{6-30}$ alkyl terminal group. Although the structural formula (III) shows compounds with three hydroxyl groups on the pyranosyl ring, the present invention is not limited thereto, but each one of said hydroxyl groups may be independently replaced, especially as a precursor in an intermediate synthetic step, with a hydroxyl-protecting group such as, but not limited to, benzyloxy or acyloxy (wherein acyl is as defined hereinabove). Although the structural formula (III) shows compounds with two hydroxyl groups on a lipid chain, the present invention is not limited thereto, but each one of said hydroxyl groups may be independently replaced, especially as a precursor in an intermediate synthetic step, with a hydroxyl-protecting group such as, but not limited to, benzyloxy or acyloxy (wherein acyl is as defined hereinabove).

According to another aspect, the present invention relates to various methods for preparing the above-defined galactopyranosyl derivatives, and intermediates therefor, according to the synthetic procedures shown in the attached FIGS. 11 to 15.

Figure 11:
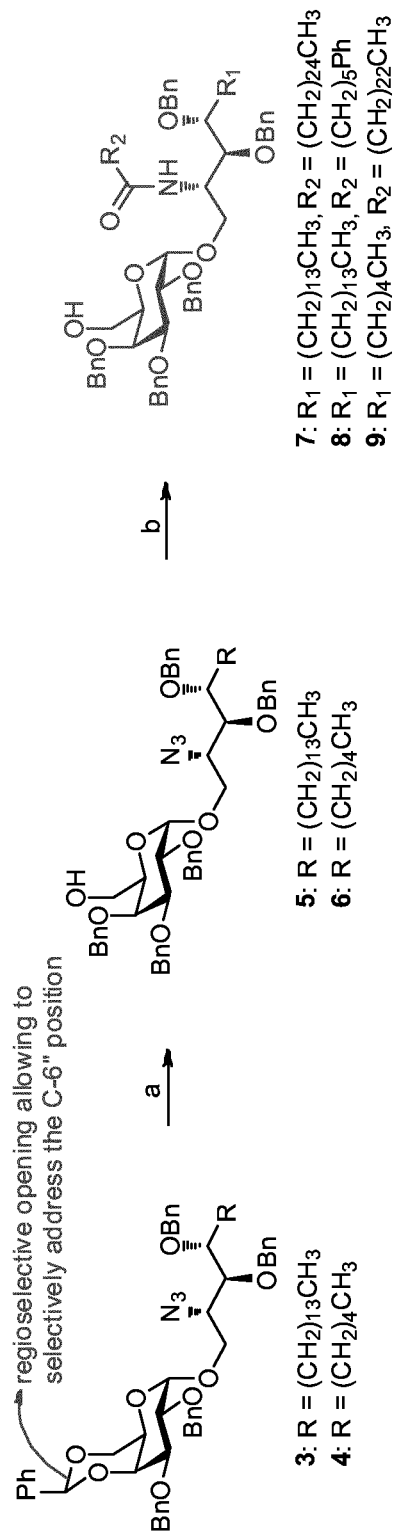
FIG. 11 schematically shows a synthetic procedure for preparing key starting intermediates of the galactopyranosyl compounds of the present invention.
Figure 12:
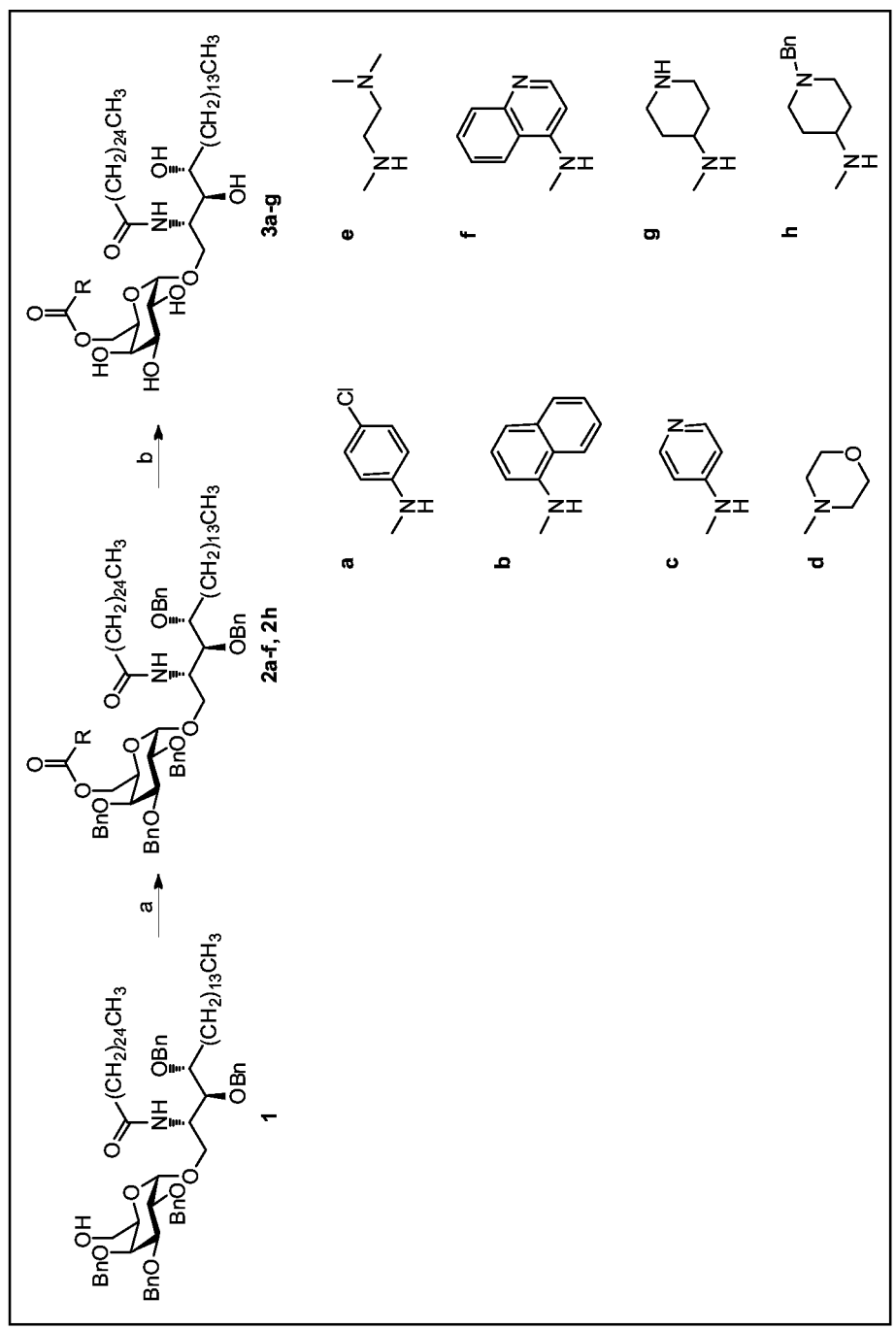
FIG. 12 schematically shows a synthetic procedure for preparing representative galactopyranosyl compounds of the present invention having a carbamate moiety.
Figure 13:
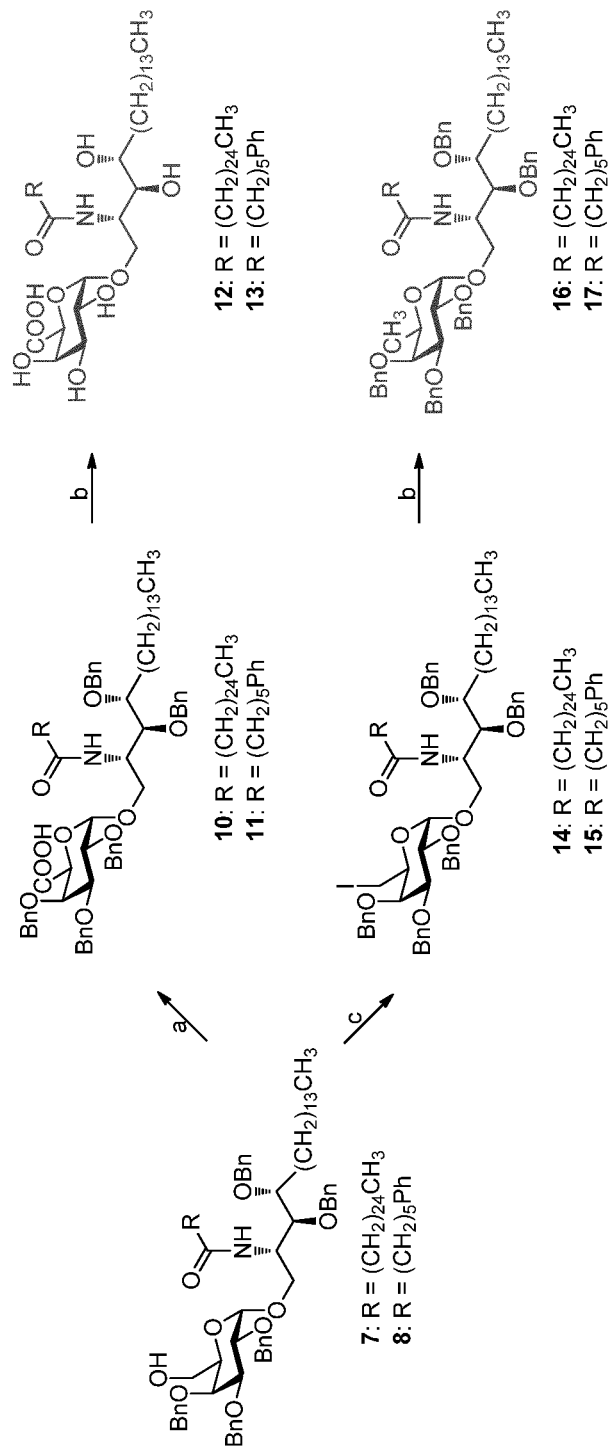
FIG. 13 schematically shows a multi-steps synthetic procedure for preparing representative galacturonic acids and 6"-deoxy analogues.

The synthesis of galactosylceramide derivatives represented by any one of the structural formulae (I), (II) and (III), including any one of the specific embodiments described herein, preferably starts from intermediates previously used in the synthesis of galacturonic acid and α-D-furopyranosyl analogues of α-GalCer, or another hydroxyl-protected analogue thereof, said intermediates being such as, but not limited to, the representative compounds 7-9 shown in FIGS. 11 and 13, or the representative compound 1 shown in FIG. 12. A suitable synthesis of such intermediates is shown in FIG. 11 and follows the basic principles of a method previously described by Figueroa-Perez and Schmidt in *Carbohyd. Res.* (2000) 95-102.

Figure 14:
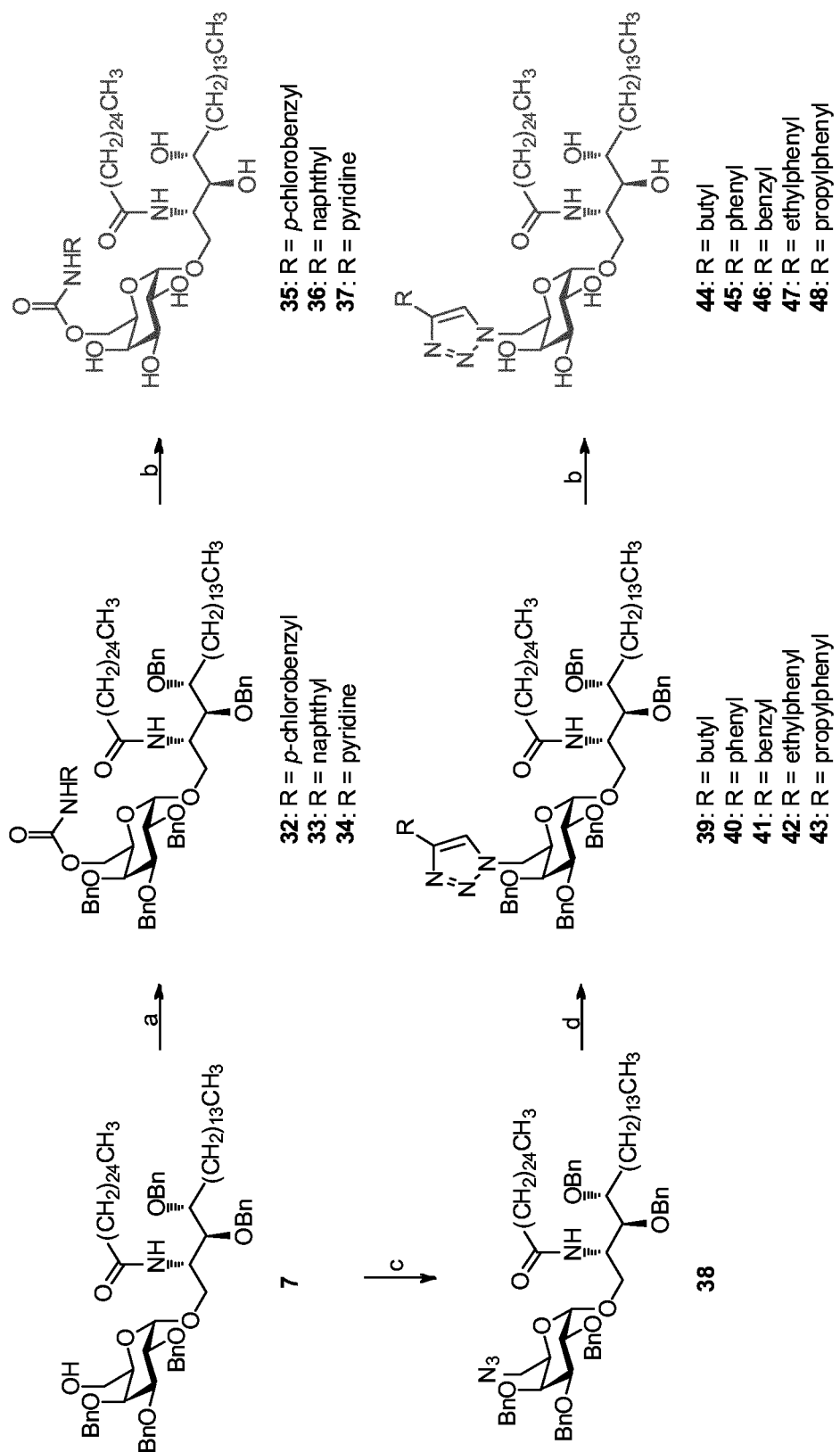
FIG. 14 schematically shows a multi-steps synthetic procedure for preparing representative galactopyranosyl compounds of the present invention having a triazolyl moiety from an azido derivative, and a synthetic procedure for preparing representative galactopyranosyl compounds of the present invention having a carbamate moiety.

Synthesis then proceeds towards the isocyanate derivatives under conditions as shown in FIG. 12 and on top of FIG. 14. The C-6"-carbamate group was introduced by reaction of the primary hydroxyl group with the appropriate isocyanate, affording the hydroxyl-protected intermediates noted as 2a-2b in FIGS. 12, or 32-33 in FIG. 14. Similar synthesis from an appropriate thioisocyanate (not shown in FIGS. 12 and 14) proceeds under similar conditions towards the corresponding thiocarbamate-containing galactopyranosyl compounds. When a specific heterocyclic isocyanate such as, but not limited to, pyridin-4-yl isocyanate was not commercially available, the desired hydroxyl-protected intermediate such as 2c (FIG. 12) or 34 (FIG. 14) was obtained by reacting a suitable heterocyclic amine, such as 4-aminopyridine, and 1,1'-carbonyldiimidazole (CDI). Finally the desired non-protected carbamates 3a-3c (FIGS. 12) or 35-37 (FIG. 14), or the corresponding thiocarbamates (not shown in the figures) may be obtained after catalytic hydrogenolysis of the hydroxyl-protecting benzyl groups, e.g. in the presence of a palladium-carbon catalytic system, or any suitable alternative deprotection method well known in the art.

As shown in FIG. 14, the synthesis of triazolyl-containing galactosylceramide derivatives represented by the structural formula (III) preferably starts from the same intermediate previously used in the synthesis of galacturonic acid and α-D-fucopyranosyl analogues of α-GalCer, or another hydroxyl-protected analogue thereof, e.g. the representative compound 7 shown in FIGS. 11 and 13, or the representative compound 1 shown in FIG. 12. First an azido group is inserted in place of the free primary hydroxyl group of the galactosyl ring by procedures well known in the art such as, but not limited to, the action of a phosphine (such as but not limited to a triarylphosphine, e.g. triphenylphosphine), diethyl azodicarboxylate (DEAD), and/or diphenylphosphoryl azide (DPPA) in a suitable solvent (such as tetrahydrofuran at low temperature (e.g. about −20° C. to about 25° C.). Then in a second step the resulting azido-terminated intermediate derivative 38 is reacted with an optionally substituted alkyne represented by the structural formula HCCR, wherein R is as defined in formula (III), thus affording the hydroxyl-protected intermediates noted as 39-43 in FIG. 14. Suitable optionally substituted alkynes for the purpose of this reaction include, but are not limited to, phenylacetylene, propyne, 1-phenylpropyne, 1-phenylbutyne, 1-phenylpentyne, propargyl bromide, propargyl chloride, propargylamine, butyne, and analogues thereof. This reaction is preferably performed under typical azide-alkyne Huisgen-cycloaddition conditions well known in the art.

Then finally the desired non-protected triazolyl derivatives 44-48 (FIG. 14) may be obtained after catalytic hydrogenolysis of the hydroxyl-protecting benzyl groups, e.g. in the presence of a palladium-carbon catalytic system, or any suitable alternative deprotection method well known in the art. FIG. 13 shows the synthesis of galacturonic acids and 6"-deoxy analogues thereof. preferably starts from the same intermediate as above, e.g. the representative compounds 7-8 shown in FIG. 11. This synthesis method, which is considerably more simple than the method described by Stalforth et al in *Organic Letters* (2008) 1573-1576, led via the hydroxyl-protected intermediates 10-11 and 14-15, and after suitable deprotection, to two known compounds 12 and 16, as well as the new derivatives 13 and 17, which combine two Th1 featuring modifications.

Figure 15:
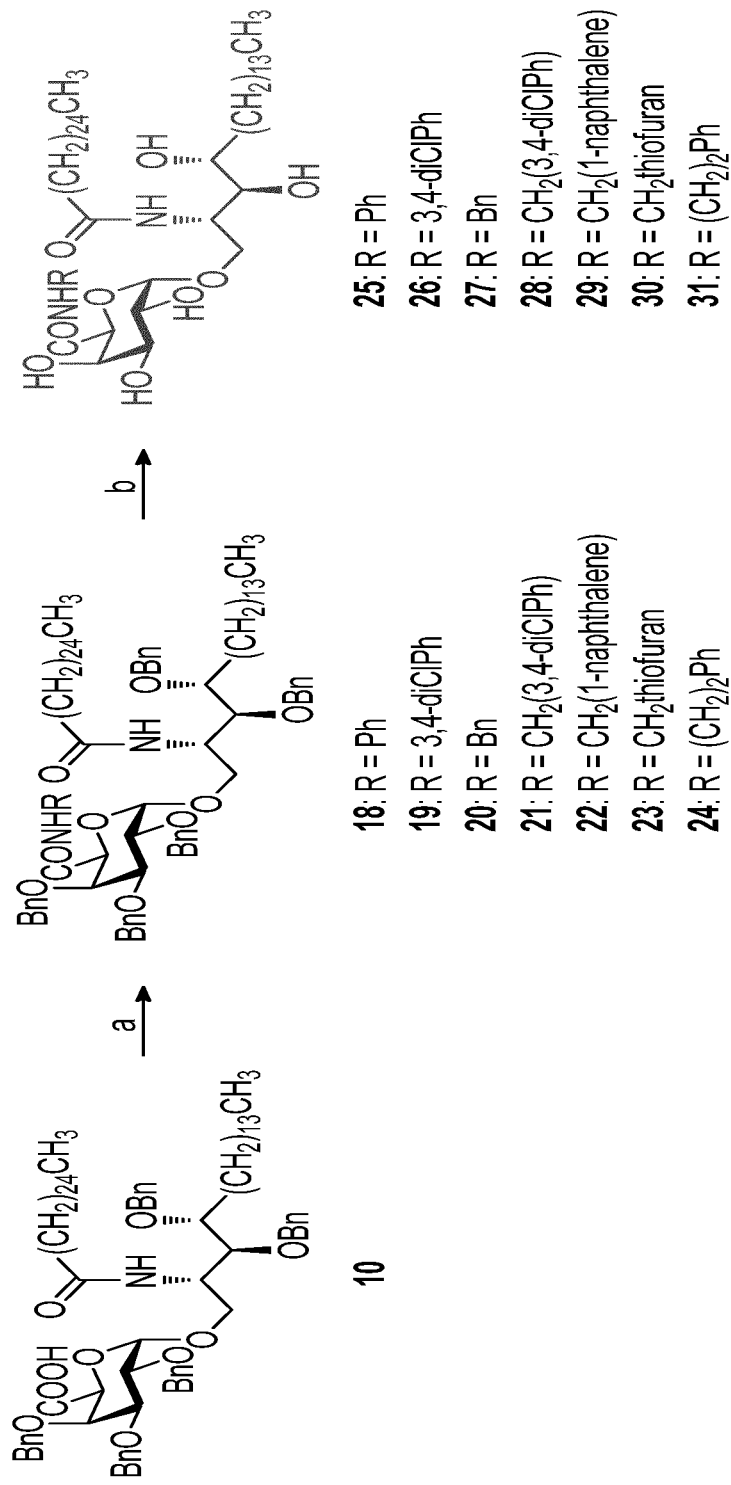
FIG. 15 schematically shows a synthetic procedure for preparing representative galactopyranosyl compounds having a 5"-amide group.

FIG. 15 shows the synthesis of 5"-amides starting for instance from the hydroxyl-protected intermediate 10. This affords first, through reaction with an amine represented by the structural formula $RNH_2$ in a suitable solvent system (such as, but not limited to dimethylformamide, methylene chloride and mixtures thereof) and in the presence of a coupling reagent such as, but not limited to, 2-(6-chloro-1-H-benzotriazol-1-yl)-1,1,3,3-tetramethyluronium haxafluorophosphate (HCTU) or 2-(1H-benzotriazole-1-yl)-1,1,3,3-Tetramethyluronium hexafluorophosphate (HBTU), the hydroxyl-protected intermediate amides 18-24 in a yield ranging from 53% to 87% depending upon the relevant amine. Then finally the desired non-protected amide derivatives 25-31 (FIG. 15) may be obtained after catalytic hydrogenolysis of the hydroxyl-protecting benzyl groups, e.g. in the presence of a palladium-carbon catalytic system, or any suitable alternative deprotection method well known in the art.

Aryl isocyanates suitable for use in the synthesis of the carbamate-containing compounds of the present invention include, but are not limited to, 4-fluorophenyl isocyanate, phenyl isocyanate, m-tolyl isocyanate, p-tolyl isocyanate, 4-chlorophenyl isocyanate, ethyl 4-isocyanatobenzoate, 2-fluorophenyl isocyanate, 3-fluoro-phenyl isocyanate, a,a,a-trifluoro-o-tolyl isocyanate, tolylene-2,4-diisocyanate, tolylene 2,6-diisocyanate, 4-methoxyphenyl isocyanate, 4-bromophenyl isocyanate, 2-methoxy-phenyl isocyanate, 3-Methoxyphenyl isocyanate, 2,4-dichlorophenyl isocyanate, o-tolyl isocyanate, 3,4-dichlorophenyl isocyanate, 2-nitrophenyl isocyanate, 4-nitrophenyl isocyanate, 2,4-difluorophenyl isocyanate, 2-bromophenyl isocyanate, 2,6-difluoro-phenyl isocyanate, 2-(trifluoromethoxy)phenyl isocyanate, 2-chloro-5-(trifluoro-methyl)phenyl isocyanate, 4-chloro-2-(trifluoromethyl)phenyl isocyanate, 4-chloro-3-(trifluoromethyl)phenyl isocyanate, 2,5-difluorophenyl isocyanate, 4-(trifluoro-methoxy)phenyl isocyanate, 2-ethoxyphenyl isocyanate, 4-ethoxyphenyl isocyanate, 4-isopropylphenyl isocyanate, 3-acetylphenyl isocyanate, 2,6-diisopropylphenyl isocyanate, 3-bromophenyl isocyanate, 3,5-dichlorophenyl isocyanate, 4-fluoro-3-nitrophenyl isocyanate, 3,5-dimethylphenyl isocyanate, 3,5-bis(trifluoromethyl)phenyl isocyanate, 3-cyanophenyl isocyanate, 4-(methylthio)phenyl isocyanate, 2-ethylphenyl isocyanate, 2,6-dimethyl-phenyl isocyanate, a,a,a-trifluoro-p-tolyl isocyanate, 2,3-dichlorophenyl isocyanate, 4-methyl-3-nitrophenyl isocyanate, 2,4-dimethoxyphenyl isocyanate, 4-(chloromethyl)phenyl isocyanate, 4-bromo-2-chlorophenyl isocyanate, 2-bromo-4,6-difluorophenyl isocyanate, 4-bromo-2-fluorophenyl isocyanate, 4-(dimethylamino)phenyl isocyanate, 2-fluoro-5-methylphenyl isocyanate, 4-fluoro-2-nitrophenyl isocyanate, 2-fluoro-3-(trifluoromethyl)phenyl isocyanate, 2-fluoro-5-(trifluoromethyl)phenyl isocyanate, 2-fluoro-6-(trifluoromethyl)-phenyl isocyanate, 4-fluoro-2-(trifluoromethyl) phenyl isocyanate, 4-fluoro-3-(trifluoromethyl)phenyl isocyanate, 4-(heptyloxy)phenyl isocyanate, 2-iodophenyl isocyanate, 2-naphthyl isocyanate, 2-n-propylphenyl isocyanate, 4-(trifluoromethyl-thio)phenyl isocyanate, 2,3,4-trifluorophenyl isocyanate, 2,6-dichlorophenyl isocyanate, 3-nitrophenyl isocyanate, 3-chlorophenyl isocyanate, 2-chlorophenyl isocyanate, 1-naphthyl isocyanate, 2,3-dimethyl-phenyl isocyanate, 3-chloro-4-fluorophenyl isocyanate, 2,5-dimethylphenyl isocyanate, 3,4-difluorophenyl isocyanate, 2,3-dihydro-1-benzofuran-5-yl isocyanate, 2,3-dihydro-1,4-benzodioxin-6-yl isocyanate, 6-fluoro-4H-1,3-benzodioxin-8-yl isocyanate, 2,1,3-benzothiadiazol-4-yl isocyanate, 3,4-dihydro-2H-1,5-benzodioxepin-7-yl isocyanate, 3-(cyclopentyloxy)-4-methoxyphenyl isocyanate, 2-(methylthio)phenyl isocyanate, 2-(tert-butyl)phenyl isocyanate, 4-(tert-butyl)phenyl isocyanate, 3-chloro-2-methylphenyl isocyanate, 4-butyl-2-methylphenyl isocyanate, 2-ethyl-6-methylphenyl isocyanate, 4-chloro-3-nitrophenyl isocyanate, 4-bromo-2-methylphenyl isocyanate, 3-(methylthio)phenyl isocyanate, 5,5,8,8-tetramethyl-5,6,7,8-tetrahydro-2-naphthalenyl isocyanate, 5-fluoro-2-methylphenyl isocyanate, 4-phenoxyphenyl isocyanate, 4-methoxy-2-methyl-phenyl isocyanate, α,α,α-trifluoro-m-tolyl isocyanate, 2,6-dibromo-4-isopropylphenyl isocyanate, 2,6-dimethoxyphenyl isocyanate, 2-(4-isocyanatophenyl) thiophene, 4-(3-isocyanatophenyl)-2-methyl-1,3-thiazole, 3-(3-isocyanatophenyl)-5-methyl-1,2,4-oxadiazole, 1-benzothien-5-yl isocyanate, 1-(3-isocyanatophenyl)-1H-pyrrole, 1-(4-isocyanatophenyl)-1H-pyrrole, 3,5-dimethoxyphenyl isocyanate and 2,4,6-trichlorophenyl isocyanate.

Heteroaryl isocyanates suitable for use in the synthesis of the carbamate-containing compounds of the present invention include, but are not limited to, pyridines, pyrimidines and pyrazines substituted by an isocyanato group in a position adjacent to a ring nitrogen such as described in U.S. Pat. No. 3,919,228, the content of which is incorporated herein by reference, for instance trichloro-isocyanato-pyrazine, 5,6-dichloro-2-phenyl-pyrimidine-4-isocyanate, 5,6-dichloro-2-pentachloroethyl-pyrimidyl-4-isocyanate, 5,6-dichloro-2-trichloromethyl-pyrimidyl-4-isocyanate, 5,6-dichloro-2-dichloromethyl-pyrimidyl-4-isocyanate, 2,5,6-trichloropyrimidyl-4-isocyanate, 4,5,6-trichloropyrimidyl-2-isocyanate, 3,4,5,6-tetrachloro-α-pyridyl isocyanate, 6-morpholin-4-ylpyridin-2-yl isocyanate as well as the isocyanates of 3,4,5-trichloropyridine, tetrafluoropyridine, 3,5, 6-trichloro-4-phenylpyridine, 3-trichloromethyl-5,6-dibromopyridine, 3,4-dichloro-6-dichloromethylpyridine, 3,5-dinitro-6-chloropyridine, 3,6-dichloro-4-cyanopyridine, 3-chlorocarbonyl-4,5,6-trichloropyridine, 3,4,5,6,7,8-hexachloroquinoline, 4,5,6-trichloro-2-pyrimidine, 4,5,6-trifluoro-2-pyrimidine, 4,6-dichloro-5-dichloromethyl-2-pyrimidine, 4,5,6-tricyano-2-pyrimidine, 4,6-dibromo-5-nitro-2-pyrimidine, 4,6-difluoro-2-pyrimidine, 4,6-dichloro-5-phenylcarbonyl-2-pyrimidine, 2,5,6-trichloro-4-pyrimidine, 2-dichloromethyl-5,6-dichloro-4-pyrimidine, 2-pentachloroethyl-5,6-dichloro-4-pyrimidine, 2-phenyl-3,6-dichloro-4-pyrimidine, 2,5,6-trifluoro- and 2,5,6-tribromo-4-pyrimidine, 2-cyano-5,6-difluoro-4-pyrimidine, 2,5-difluoro-4-pyrimidine, 2-fluoro-5,6-dichloro-4-pyrimidine, 2-cyano-5, 6-difluoro-4-pyrimidine, 2,5-difluoro-4-pyrimidine, 2-fluoro-5,6-dichloro-4-pyrimidine, 2,6-dichloro-5-nitro-4-pyrimidine, 2-phenylcarbonyl-5-trichloromethyl-6-cyano-4-pyrimidine, trichloropyrazine, trifluoropyrazine, 2,5-dichloro-6-trichloromethyl-3-pyrazine, 2,5-dibromo-6-phenyl-3-pyrazine, tris-(trichloromethyl)-pyrazine, 2-chloro-5,6-dicyano-3-pyrazine and the like.

Non-aromatic heterocyclic isocyanates suitable for use in the synthesis of the carbamate-containing compounds of the present invention include, but are not limited to, 4-morpholinyl isocyanate, piperidin-4-yl isocyanate, and 1-benzylpiperidin-4-yl isocyanate.

erocyclyl-$C_{1-4}$ alkyl isocyanates suitable for use in the synthesis of the carbamate-containing compounds of the present invention include, but are not limited to, 4-(4-morpholinyl) butyl isocyanate and 2-(4-morpholinyl)ethyl isocyanate.

Aryl-$C_{1-4}$ alkyl isocyanates suitable for use in the synthesis of the carbamate-containing compounds of the present invention include, but are not limited to, benzyl isocyanate, phenethyl isocyanate and 1-phenylethyl isocyanate.

Cycloalkyl-$C_{1-4}$ alkyl isocyanates suitable for use in the synthesis of the carbamate-containing compounds of the present invention include, but are not limited to, cyclopentylmethyl isocyanate and cyclohexylmethyl isocyanate.

$C_{3-10}$ cycloalkyl isocyanates suitable for use in the synthesis of the carbamate-containing compounds of the present invention include, but are not limited to, cyclopentyl isocyanate and cyclohexyl isocyanate.

$C_{1-8}$ alkyl isocyanates suitable for use in the synthesis of the carbamate-containing compounds of the present invention include, but are not limited to, methyl isocyanate, ethyl isocyanate, propyl isocyanate, isopropyl isocyanate, n-butyl isocyanate, tert-butyl isocyanate, and octyl isocyanate.

Isocyanates desirable, but not commercially available, for use in the synthesis of the carbamate-containing compounds of the present invention can be prepared according to synthetic procedures well known to those skilled in the art, e.g. through reaction of the corresponding primary amine and phosgene.

Aryl isothiocyanates suitable for use in the synthesis of the thiocarbamate-containing compounds of the present invention include, but are not limited to, phenyl isothiocyanate, 4-fluorophenyl isothiocyanate, methyl 2-isocyanatobenzoate, 2-chlorophenyl isothiocyanate, 3-chlorophenyl isothiocyanate, o-tolyl isothiocyanate, m-tolyl isothiocyanate, p-tolyl isothiocyanate, 2-methoxyphenyl isothiocyanate, 2-bromophenyl isothiocyanate, 3-bromophenyl isothiocyanate, 2,4-dichloro-phenyl isothiocyanate, 2-fluoro phenylisothiocyanate, 4-methoxyphenyl isothiocyanate, a,a,a-trifluoro-m-tolyl isothiocyanate, 3-fluorophenyl isothiocyanate, 3,5-bis(trifluoromethyl)phenyl isothiocyanate, 1-naphthyl isothiocyanate, 4-dimethylamino-1-naphthyl isothiocyanate, 4-(methylthio)-phenyl isothiocyanate, 2-methoxy-5-methylphenyl isothiocyanate, 4-cyanophenyl isothiocyanate, 3-chloro-4-fluorophenyl isothiocyanate, 4-nitrophenyl isothiocyanate, 4-bromophenyl isothiocyanate, 2,3-dihydro-1,4-benzodioxin-6-yl isothiocyanate, 1,3-benzodioxol-5-yl isothiocyanate, 4-(1H-pyrazol-1-yl)phenyl isothiocyanate, 2-(trifluoromethyl) phenyl isothiocyanate, 2,3-dimethylphenyl isothiocyanate, 2-isopropyl phenyl isothiocyanate, 4-isopropylphenyl isothiocyanate, 5-chloro-2-methoxyphenyl isothiocyanate, 2,4-dimethoxyphenyl isothiocyanate, 2,4-dichloro-6-methylphenyl isothiocyanate, 2-bromo-4-isopropylphenyl isothiocyanate, 5-chloro-2-fluorophenyl isothiocyanate, 4-(trifluoromethoxy)phenyl isothiocyanate, 3,5-dimethylphenyl isothiocyanate, 3,5-dimethoxyphenyl isothiocyanate, 4-chlorophenyl isothiocyanate, 3,4-dimethoxyphenyl isothiocyanate, 2,6-dimethylphenyl isothiocyanate, 3-methoxyphenyl isothiocyanate, mesityl isothiocyanate, 4-(benzyloxy)phenyl isothiocyanate, 2,4-dimethylphenyl isothiocyanate, 2-bromo-5-fluorophenyl isothiocyanate, 5-fluoro-2-methylphenyl isothiocyanate, 4-chloro-2,5-dimethoxyphenyl isothiocyanate, 2,5-dichlorophenyl isothio-cyanate, 2-(tert-butyl)-4,5,6-trimethyl-3-nitrophenyl isothiocyanate, 2-isopropyl-6-methylphenyl isothiocyanate, 4-ethoxyphenyl isothiocyanate, 5-chloro-2-methylphenyl isothiocyanate, 2-ethyl-6-methylphenyl isothiocyanate and 4-(trifluoromethyl) phenyl isothiocyanate.

Aryl-$C_{1-4}$ alkyl isothiocyanates suitable for use in the synthesis of the thiocarbamate-containing compounds of the present invention include, but are not limited to, benzyl isothiocyanate and phenethyl isothiocyanate. $C_{1-4}$ alkyl isothiocyanates suitable for use in the synthesis of the thiocarbamate-containing compounds of the present invention include, but are not limited to, methyl isothiocyanate.

Isothiocyanates desirable, but not commercially available, for use in the synthesis of the thiocarbamate-containing compounds of the present invention can be prepared according to synthetic procedures well known to those skilled in the art, e.g. through reaction of the corresponding primary amine and carbon disulphide.

In another particular embodiment, the invention relates to a group of compounds represented by any one of the above structural formulae (I), (II) and (III), and being in the form of a pharmaceutically acceptable salt. The latter include any therapeutically active non-toxic addition salt which compounds represented by the structural formulae (I), (II) and (III), including any one of the specific embodiments described herein, are able to form with a salt-forming agent. Such addition salts may conveniently be obtained by treating the compounds of this invention with an appropriate salt-forming acid or base. For instance, derivatives having basic properties may be converted into the corresponding therapeutically active, non-toxic acid addition salt form by treating the free base form with a suitable amount of an appropriate acid following conventional procedures. Examples of such appropriate salt-forming acids include, for instance, inorganic acids resulting in forming salts such as, but not limited to, hydrohalides (e.g. hydrochloride and hydrobromide), sulfate, nitrate, phosphate, diphosphate, carbonate, bicarbonate, and the like; and organic mono- or di-acids resulting in forming salts such as, for example, acetate, propanoate, hydroxyacetate, 2-hydroxypropanoate, 2-oxopropanoate, lactate, pyruvate, oxalate, malonate, succinate, maleate, fumarate, malate, tartrate, citrate, methanesulfonate, ethanesulfonate, benzoate, 2-hydroxybenzoate, 4-amino-2-hydroxybenzoate, benzenesulfonate, p-toluene-sulfonate, salicylate, p-aminosalicylate, pamoate, bitartrate, camphor-sulfonate, edetate, 1,2-ethanedisulfonate, fumarate, glucoheptonate, gluconate, glutamate, hexylresorcinate, hydroxynaphtoate, hydroxyethane-sulfonate, mandelate, methylsulfate, pantothenate, stearate, as well as salts derived from ethanedioic, propanedioic, butanedioic, (Z)-2-butenedioic, (E)2-butenedioic, 2-hydroxybutanedioic, 2,3-dihydroxybutane-dioic, 2-hydroxy-1,2,3-propane-tricarboxylic and cyclohexane-sulfamic acids and the like.

Compounds having acidic properties may be converted in a similar manner into the corresponding therapeutically active, non-toxic base addition salt form. Examples of appropriate salt-forming bases include, for instance, inorganic bases like metallic hydroxides such as, but not limited to, those of alkali and alkaline-earth metals like calcium, lithium, magnesium, potassium and sodium, or zinc, resulting in the corresponding metal salt; organic bases such as but not limited to ammonia, alkylamines, benzathine, hydrabamine, arginine, lysine, N,N'-dibenzylethylenediamine, chloroprocaine, choline, diethanolamine, ethylene-diamine, N-methylglucamine, procaine and the like.

Reaction conditions for treating the compounds of this invention represented by any one of the above structural formulae (I), (II) and (III), including any one of the specific embodiments described herein, with an appropriate salt-forming acid or base are similar to standard conditions involving the same acid or base but different organic compounds with basic or acidic properties, respectively. Preferably, in view of its use in a pharmaceutical composition or in the manufacture of a medicament for treating specific diseases, the pharmaceutically acceptable salt will be designed, i.e. the salt-forming acid or base will be selected so as to impart greater water solubility, lower toxicity, greater stability and/or slower dissolution rate to the compound of this invention.

In another aspect, this invention provides pharmaceutical compositions comprising a therapeutically effective amount of a compound represented by any one of the above structural formulae (I), (II) and (III), including any one of the above embodiments thereof and including pharmaceutically acceptable salts thereof, and one or more pharmaceutically acceptable excipients or carriers. The pharmaceutical compositions of this invention include one or more compounds according to any one of the structural formulae (I) to (III) as an active ingredient in admixture with at least a pharmaceutically acceptable carrier, the active ingredient being in a concentration of at least about 0.1%, preferably at least 0.5%, for instance at least 1%, or at least 5%, by weight of the composition. Preferably the active ingredient is in a concentration of at most about 50%, more preferably at most 30%, most preferably at most 20% by weight of the composition.

More generally, the invention relates to the compounds having any one of the structural formulae (I) to (III) being useful as agents having biological activity (e.g. an anti-metastatic or antitumoral activity) or as diagnostic agents. Any of the uses mentioned with respect to the present invention may be restricted to a non-medical use, a non-therapeutic use, a non-diagnostic use, or exclusively an in vitro use, or a use related to cells remote from an animal.

This invention further relates to a pharmaceutical composition comprising one or more compounds according to any one of the structural formulae (I) to (III) as an active ingredient in combination with at least another therapeutic agent such as, but not limited to, another anti-metastatic or antitumoral agent, or a cell proliferaion inhibitor, or a Th1/Th2 modulator, or an immunomodulating agent. Optimally, the another therapeutic agent should be selected in order to provide a synergistic effect in the desired biological activity.

As is conventional in the art, the evaluation of a synergistic effect in a combination of therapeutic agents (drugs) may be made by analyzing the quantification of the interactions between individual drugs, using the median effect principle described by Chou et al. in *Adv. Enzyme Reg.* (1984) 22:27. Briefly, this principle states that interactions (synergism, additivity, antagonism) between two drugs can be quantified using the combination index (hereinafter referred as CI) defined by the following equation:

$$CI_x = \frac{ED_x^{1c}}{ED_x^{1a}} + \frac{ED_x^{2c}}{ED_x^{2a}}$$

wherein $ED_x$ is the dose of the first or respectively second drug used alone (1a, 2a), or in combination with the second or respectively first drug (1c, 2c), which is needed to produce a given effect. The said first and second drug have synergistic or additive or antagonistic effects depending upon CI<1, CI=1, or CI>1, respectively.

Synergistic activity of the pharmaceutical compositions or combined preparations of this invention, for instance in iNKT cell activation, or anti-metatstatic activity, or anti-tumor effect, or immunomodulation, may also be readily determined by means of one or more tests such as, but not limited to, the isobologram method, as previously described by Elion et al. in *J. Biol. Chem.* (1954) 208:477-488 and by Baba et al. in *Antimicrob. Agents Chemother.* (1984) 25:515-517, using $EC_{50}$ for calculating the fractional inhibitory concentration (hereinafter referred as FIC). When the minimum FIC index corres-ponding to the FIC of combined compounds (e.g., $FIC_x + FIC_y$) is equal to 1.0, the combination is said to be additive; when it is beween 1.0 and 0.5, the combination is defined as subsynergistic, and when it is lower than 0.5, the combination is defined as synergistic. When the minimum FIC index is between 1.0 and 2.0, the combination is defined as subantagonistic and, when it is higher than 2.0, the combination is defined as antagonistic.

In view of the fact that, when several active ingredients are used in combination, they do not necessarily bring out their joint therapeutic effect directly at the same time in the mammal to be treated, the corresponding composition may also be in the form of a medical kit or package containing the two ingredients in separate but adjacent repositories or compartments. In the latter context, each active ingredient may therefore be formulated in a way suitable for an administration route different from that of the other ingredient, e.g. one of them may be in the form of an oral or parenteral formulation whereas the other is in the form of an ampoule for intravenous injection or an aerosol.

Depending upon the specific disease to be treated, the pharmaceutical compositions according to this invention may be administered orally or in any other suitable fashion. In case of oral administration, the preparation may have the form of a tablet, aqueous dispersion, dispersible powder or granule, emulsion, hard or soft capsule, syrup, elixir or gel. The dosing forms may be prepared using any method known in the art for manufacturing these pharmaceutical compositions and may comprise as additives sweeteners, flavouring agents, colouring agents, preservatives and the like. Carrier materials and excipients are detailed herein below and may include, inter alia, calcium carbonate, sodium carbonate, lactose, calcium phosphate or sodium phosphate; granulating and disintegrating agents, binding agents and the like. The pharmaceutical composition of this invention may be included in a gelatin capsule mixed with any inert solid diluent or carrier material, or has the form of a soft gelatin capsule, in which the ingredient is mixed with a water or oil medium. Aqueous dispersions may comprise the biologically active composition or combined preparation in combination with a suspending agent, dispersing agent or wetting agent. Oil dispersions may comprise suspending agents such as a vegetable oil. Rectal administration is also applicable, for instance in the form of suppositories or gels.

Due to the water-solubility characteristics of the compounds of the present invention under physiological conditions, injection (e.g. intramuscularly or intraperitoneously) is also applicable as a mode of administration, for instance in the form of injectable aqueous solutions or dispersions, depending upon the disorder to be treated and the condition of the patient. Examples of aqueous solutions include, but are not limited to, water saline, phosphate buffered saline, Hank's solution, Ringer's solution, dextrose/saline, glucose solutions and the like. The pharmaceutical injectable compositions may contain one or more pharmaceutically acceptable auxiliary substances as required to approximate physiological conditions or to improve stability, appearance or ease of administration, such as buffering agents, tonicity adjusting agents, wetting agents, detergents and the like. Additives can also include additional active ingredients such as bactericidal agents, vaccine adjuvants or stabilising agents. For example, the aqueous solution of the invention may contain one or more additives selected from the group consisting of sodium acetate, sodium lactate, sodium chloride, potassium chloride, calcium chloride, sorbitan monolaurate and triethanolamine oleate. These aqueous compositions can be sterilised by conventional, well-known sterilisation techniques, or can be sterile filtered. The resulting aqueous solutions can be packaged for use as such, or can be lyophilised, the lyophilised preparation being combined with a sterile aqueous solution prior to administration. Such aqueous solutions are appropriate for injection and, in particular, for intravenous injection. Intravenous injection may be a particularly appropriate means of delivery for certain compounds of this invention. The intravenous solution can include detergents and emulsifiers such as lipids. Aqueous solutions also are useful for oral and enteral and other routes of administration as tonics, and for administration to mucous or other membranes as, e.g., nose or eye drops. The aqueous composition of this invention may contain the galactosyl ceramide compound, or a pharmaceutically acceptable salt thereof, in an amount from about 1 mg/ml to about 100 mg/ml, preferably from about 5 to 20 mg/ml.

The term "pharmaceutically acceptable carrier or excipient" as used herein in relation to any type of pharmaceutical compositions means any material or substance with which the active principle, i.e. the galactosyl ceramide derivative of this invention, may be formulated in order to facilitate its application or dissemination to the locus to be treated, for instance by dissolving, dispersing or diffusing the said composition, and/or to facilitate its storage, transport or handling without impairing its effectiveness. The pharmaceutically acceptable carrier may be a solid or a liquid or a gas which has been compressed to form a liquid, i.e. the compositions of this invention can suitably be used as concentrates, emulsions, solutions, granulates, dusts, sprays, aerosols, pellets or powders.

Suitable pharmaceutical carriers for use in the said pharmaceutical compositions and their formulation are well known to those skilled in the art. There is no particular restriction to their selection within the present invention although special attention may be paid to the selection of suitable carrier combinations that can assist in properly formulating the galactosyl ceramide derivative in view of the expected time release profile. Suitable pharmaceutical carriers include additives such as wetting agents, dispersing agents, stickers, adhesives, emulsifying or surface-active agents, thickening agents, complexing agents, gelling agents, solvents, coatings, antibacterial and antifungal agents (for example phenol, sorbic acid, chlorobutanol), isotonic agents (such as sugars or sodium chloride) and the like, provided the same are consistent with pharmaceutical practice, i.e. carriers and additives which do not create permanent damage to mammals.

The pharmaceutical compositions of the present invention may be prepared in any known manner, for instance by homogeneously mixing, dissolving, spray-drying, extruding, coating and/or grinding the active ingredients, in a one-step or a multi-steps procedure, with the selected carrier material and, where appropriate, the other additives such as surface-active agents. The compositions may also be prepared by extrusion-spheronization or micronisation, for instance in view to obtain them in the form of microspheres usually having a diameter of about 1 to 10 µm, namely for the manufacture of microcapsules for controlled or sustained release of the biologically active agent.

Suitable surface-active agents to be used in the pharmaceutical compositions of the present invention are non-ionic, cationic and/or anionic surfactants having good emulsifying, dispersing and/or wetting properties.

Suitable anionic surfactants include both water-soluble soaps and water-soluble synthetic surface-active agents. Suitable soaps are alkaline or alkaline-earth metal salts, unsubstituted or substituted ammonium salts of higher fatty acids ($C_{10}$-$C_{22}$), e.g. the sodium or potassium salts of oleic or stearic acid, or of natural fatty acid mixtures obtainable form coconut oil or tallow oil. Synthetic surfactants include sodium or calcium salts of polyacrylic acids; fatty sulphonates and sulphates; sulphonated benzimidazole derivatives and alkylarylsulphonates. Fatty sulphonates or sulphates are usually in the form of alkaline or alkaline-earth metal salts, unsubstituted ammonium salts or ammonium salts substituted with an alkyl or acyl radical having from 8 to 22 carbon atoms, e.g. the sodium or calcium salt of lignosulphonic acid or dodecylsulphonic acid or a mixture of fatty alcohol sulphates obtained from natural fatty acids, alkaline or alkaline-earth metal salts of sulphuric or sulphonic acid esters (such as sodium lauryl sulphate) and sulphonic acids of fatty alcohol/ethylene oxide adducts. Suitable sulphonated benzimidazole derivatives preferably contain 8 to 22 carbon atoms. Examples of alkylarylsulphonates are the sodium, calcium or alcanolamine salts of dodecylbenzene sulphonic acid or dibutyl-naphthalenesulphonic acid or a naphtalene-sulphonic acid/formaldehyde condensation product. Also suitable are the corresponding phosphates, e.g. salts of phosphoric acid ester and an adduct of p-nonylphenol with ethylene and/or propylene oxide, or phospholipids. Suitable phospholipids for this purpose are the natural (originating from animal or plant cells) or synthetic phospholipids of the cephalin or lecithin type such as e.g. phosphatidylethanolamine, phosphatidylserine, phosphatidylglycerine, lysolecithin, cardiolipin, dioctanyl-phosphatidylcholine, dipalmitoylphoshatidylcholine and their mixtures.

Suitable non-ionic surfactants include polyethoxylated and polypropoxylated derivatives of alkylphenols, fatty alcohols, fatty acids, aliphatic amines or amides containing at least 12 carbon atoms in the molecule, alkylarenesulphonates and dialkylsulphosuccinates, such as polyglycol ether derivatives of aliphatic and cycloaliphatic alcohols, saturated and unsaturated fatty acids and alkylphenols, said derivatives preferably containing 3 to 10 glycol ether groups and 8 to 20 carbon atoms in the (aliphatic) hydrocarbon moiety and 6 to 18 carbon atoms in the alkyl moiety of the alkylphenol. Further suitable non-ionic surfactants are water-soluble adducts of polyethylene oxide with poylypropylene glycol, ethylene-diamino-polypropylene glycol containing 1 to 10 carbon atoms in the alkyl chain, which adducts contain 20 to 250 ethyleneglycol ether groups and/or 10 to 100 propyleneglycol ether groups. Such compounds usually contain from 1 to 5 ethyleneglycol units per propyleneglycol unit. Representative examples of non-ionic surfactants are nonylphenol-polyethoxyethanol, castor oil poly-glycolic ethers, polypropylene/polyethylene oxide adducts, tributylphenoxypolyethoxyethanol, polyethyleneglycol and octylphenoxypolyethoxyethanol. Fatty acid esters of polyethylene sorbitan (such as polyoxyethylene sorbitan trioleate), glycerol, sorbitan, sucrose and pentaerythritol are also suitable non-ionic surfactants.

Suitable cationic surfactants include quaternary ammonium salts, preferably halides, having four hydrocarbon radicals optionally substituted with halo, phenyl, substituted phenyl or hydroxy; for instance quaternary ammonium salts containing as N-substituent(s) at least one $C_8$-$C_{22}$ alkyl radical (e.g. cetyl, lauryl, palmityl, myristyl, oleyl and the like) and, as further substituents, unsubstituted or halogenated lower alkyl, benzyl and/or hydroxy-$C_{1-4}$ alkyl radicals.

A more detailed description of surface-active agents suitable for this purpose may be found for instance in "McCutcheon's Detergents and Emulsifiers Annual" (MC Publishing Crop., Ridgewood, N.J., 1981), "Tensid-Taschenbuch", $2^{nd}$ ed. (Hanser Verlag, Vienna, 1981) and "Encyclopaedia of Surfactants (Chemical Publishing Co., New York, 1981).

Structure-forming, thickening or gel-forming agents may be included into the pharmaceutical compositions and combined preparations of the invention. Suitable such agents are in particular highly dispersed silicic acid, such as the product commercially available under the trade name Aerosil; bentonites; tetraalkyl ammonium salts of montmorillonites (e.g. products commercially available under the trade name Bentone), wherein each of the alkyl groups may contain from 1 to 20 carbon atoms; cetostearyl alcohol and modified castor oil products (e.g. the product commercially available under the trade name Antisettle).

Gelling agents which may be included into the pharmaceutical compositions of the present invention include, but are not limited to, cellulose derivatives such as carboxymethylcellulose, cellulose acetate and the like; natural gums such as arabic gum, xanthum gum, tragacanth gum, guar gum and the like; gelatin; silicon dioxide; synthetic polymers such as carbomers, and mixtures thereof. Gelatin and modified celluloses represent a preferred class of gelling agents.

Other optional excipients which may be included in the pharmaceutical compositions of the present invention include additives such as magnesium oxide; azo dyes; organic and inorganic pigments such as titanium dioxide; UV-absorbers; stabilisers; odor masking agents; viscosity enhancers; antioxidants such as, for example, ascorbyl palmitate, sodium bisulfite, sodium metabisulfite and the like, and mixtures thereof; preservatives such as, for example, potassium sorbate, sodium benzoate, sorbic acid, propyl gallate, benzylalcohol, methyl paraben, propyl paraben and the like; sequestering agents such as ethylene-diamine tetraacetic acid; flavoring agents such as natural vanillin; buffers such as citric acid and acetic acid; extenders or bulking agents such as silicates, diatomaceous earth, magnesium oxide or aluminum oxide; densification agents such as magnesium salts; and mixtures thereof.

Additional ingredients may be included in order to control the duration of action of the biologically-active agent (a galactosyl ceramide compound represented by any one of the above structural formulae (I), (II) and (III), including any specific embodiment thereof, or a pharmaceutically acceptable salt thereof) in the pharmaceutical compositions of the invention. Control release pharmaceutical compositions may thus be achieved by selecting appropriate polymer carriers such as for example polyesters, polyamino-acids, polyvinylpyrrolidone, ethylene-vinyl acetate copolymers, methylcellulose, carboxy-methylcellulose, protamine sulfate and the like. The rate of drug release and duration of action may also be controlled by incorporating the active agent into particles, e.g. microcapsules, of a polymeric substance such as hydrogels, polylactic acid, hydroxymethylcellulose, polymethylmethacrylate and the other above-described polymers. Such methods include colloid drug delivery systems like liposomes, microspheres, micro-emulsions, nanoparticles, nanocapsules and so on. Depending upon the route of administration, the pharmaceutical composition of this invention may also require protective coatings well known in the art.

Pharmaceutical forms suitable for injectable use include sterile aqueous solutions or dispersions and sterile powders for the extemporaneous preparation thereof. Typical carriers for this purpose therefore include biocompatible aqueous buffers, ethanol, glycerol, propylene glycol, polyethylene glycol, complexing agents such as cyclodextrins and the like, and mixtures thereof in any suitable proportions.

Other modes of local drug administration can also be used. For example, the selected glycosylceramide active agent of this invention may be administered topically, in an ointment, gel or the like, or transdermally, using a conventional transdermal drug delivery system.

In another aspect, this invention provides various methods of treatment of disorders or prevention of physiological conditions in mammals, especially human beings, in need thereof, the said methods comprising administering an effective amount of a galactosyl ceramide compound represented by any one of the above structural formulae (I), (II) and (III), including any one of the specific embodiments described hereinabove, or a pharmaceutically acceptable salt thereof, to said mammal. When using one or more compounds according to any one of the structural formulae (I) to (III) as defined herein:

the active ingredients of the compound(s) may be administered to the mammal (including a human) to be treated by any means well known in the art, i.e. orally, intranasally, subcutaneously, intramuscularly, intradermally, intravenously, intra-arterially, parenterally or by catheterization;

the therapeutically effective amount of the preparation of the compound(s) for the treatment of disorders in humans and other mammals may readily be determined by the practician depending upon the type of compound, the severity of the disorder, the general condition of the patient and other parameters conventional in the art.

Depending upon the pathologic condition to be treated and the patient's condition, the therapeutically effective amount may be divided into several sub-units per day, or may be administered at more than one day intervals.

In particular the present invention relates to methods of treatment or prevention of such diseases in mammals, especially human beings, wherein NKT cells stimulation is desired. The present invention also relates to methods of stimulating an immune response in a mammal, especially a human being, the said methods comprising administering an effective amount of a galactosyl ceramide compound represented by any one of the above structural formulae (I), (II) and (III), including any one of the specific embodiments described hereinabove, or a pharmaceutically acceptable salt thereof, to said mammal. The invention also relates to methods of treatment or prevention of diseases associated with a disruption of the Th1/Th2 cytokine response balance in a mammal (especially a human being), in particular:

cell proliferative disorders,
immune disorders (e.g. organ and cells transplant rejections),
auto-immune disorders, and
infectious diseases.

Within the framework of cell proliferative disorders, the methods of the present invention are particularly useful for treating various forms of cancer such as, but not limited to, breast cancer, leukemia, Burkitt's lymphoma, colorectal cancer, esophageal cancer, bladder cancer, gastric cancer, head and neck cancer, hepatocellular cancer, Hodgkin's lymphoma, hairy cell leukemia Wilm's tumor, thyroid cancer, thymoma and thymic carcinoma, testicular cancer, T-cell lymphoma, prostate cancer, lung cancer, liver cancer, renal cell cancer, sarcoma, osteosarcoma and melanoma. Within this aspect of the method of treatment of the present invention, a galactosyl ceramide compound represented by any one of the above structural formulae (I), (II) and (III), including any one of the specific embodiments described hereinabove, or a pharmaceutically acceptable salt thereof, is especially useful in view of its anti-tumor effect and/or its anti-metastatic activity. It may be administered to the patient in need thereof, simultaneously or not, with one or more anti-tumor or anti-metastatic agents, or cell proliferation inhibitors well known in the art of cancer treatment, in view of obtaining an enhanced response or synergistic activity.

Within the framework of auto-immune disorders, the present invention is particularly useful for treating (1) a rheumatic disease such as, but not limited to, rheumatoid arthritis, systemic lupus erythematosus, Sjogren's syndrome, scleroderma, mixed connective tissue disease, dermatomyositis, polymyositis, Reiter's syndrome or Behcet's disease, (2) type I or type II diabetes, (3) an autoimmune thyroid disease such as, but not limited to, Hashimoto's thyroiditis or Graves' Disease, (4) an autoimmune disease of the central nervous system such as, but not limited to, multiple sclerosis, myasthenia gravis, or encephalomyelitis, (5) a variety of phemphigus such as, but not limited to, phemphigus vulgaris, phemphigus vegetans, phemphigus foliaceus, Senear-Usher syndrome, or Brazilian phemphigus, (6) skin diseases such as, but not limited to, psoriasis or neurodermitis, and (7) inflammatory bowel disease (e. g., ulcerative colitis or Crohn's Disease). Within this aspect of the method of treatment of the present invention, a galactosyl ceramide compound represented by any one of the above structural formulae (I), (II) and (III), including any one of the specific embodiments described hereinabove, or a pharmaceutically acceptable salt thereof, may be administered to the patient in need thereof, simultaneously or not, with one or more immunomodulating agents well known in the art of immunologic therapy, in view of obtaining an enhanced response or synergistic activity.

The present invention also relates to the use of a galactosyl ceramide compound represented by any one of the above structural formulae (I), (II) and (III), including any one of the above described more specific embodiments thereof, or a pharmaceutically acceptable salt thereof, as an immune adjuvant to improve the efficiency of a vaccine against a human tumor or an infectious disease such as, but not limited to, tuberculosis, malaria and various forms of the autoimmune deficiency syndrome (AIDS). Within the framework of this use, without wishing to be bound by theory, it is believed that the galactosyl ceramide compound of the present invention may act at many sites in the immune response, e.g. directly on T cells or on dendritic cells, for instance by polarizing the immune response toward a Th2 type, or by inducing suppressive macrophages and/or cytokines.

The following examples are provided for illustration purposes only, and are based on the synthetic schemes and compound notations shown in the attached FIGS. 11-15, which merely constitutes a particular embodiment of the more generally applicable synthetic procedures shown in these figures.

In one specific embodiment of the present invention we synthesized a diverse set of derivatives modified at the C-5"- or C-6"-position of the galactopyranosyl ring. Towards this end, a divergent synthetic route was developed in which key intermediates 3 and 4 gave easy access to the desired amides 5-11, triazoles 12-16 and carbamates 17-19. This route also allowed to combine two known Th1 featuring modifications as in galacturonic acid 21 and fucosyl analogue 23. Analogues 24 and 25 were synthesized to assess the biological effect of combining the CD1d affinity enhancing sugar modifications with an OCH-like phytosphingosine chain.

EXAMPLE 1

Synthesis of Carbamate-containing Galactopyranosyl Compounds

General Structure and Synthesis of C-6"-carbamates

The synthesis of the desired carbamates 3a-c started from compound 1 (FIG. 12: reagents and conditions: (a) R—N=C=O, dimethylformamide (DMF), room temperature, or R—NH$_2$, 1,1'-carbonyldiimidazole (CDI), DMF, room temperature till 70° C.; (b) Pd black, H$_2$, solvent mixture EtOH/CHCl$_3$, room temperature), an intermediate previously used in the synthesis of galacturonic acid and α-D-fucopyranosyl analogues of α-GalCer. The C-6"-carbamate group was introduced by reaction of the free primary hydroxyl group on the galactosyl ring with the appropriate isocyanate (respectively 4-chloro-phenyl isocyanate and 1-naphthyl isocyanate), affording 2a and 2b. When pyridin-4-yl isocyanate was not commercially available, compound 2c was obtained by using 4-aminopyridine and 1,1'-carbonyldiimidazole (CDI). Final de-benzylation by means of catalytic hydrogenation resulted in the desired carbamates 3a-c.

Pre-coated Macherey-Nagel SIL G/UV$_{254}$ plates were used for thin layer chromatography (TLC), and spots were examined under ultra-violet (UV) light at 254 nm and further visualized by means of a sulfuric acid-anisaldehyde spray.

Column chromatography was performed on Biosolve silica gel (63-200 μm, 60 Å, commercially available from ICN, Asse, Belgium).

Nuclear magnetic resonance (NMR) spectra were obtained with a Varian Mercury 300 Spectrometer. Chemical shifts are given in ppm relative to the residual solvent signals as follows:

in the case of CDCl$_3$: 7.26 ppm for $^1$H; 77.4 ppm for $^{13}$C, and in the case of pyridine-d$_5$: 8.74, 7.58 and 7.22 ppm for $^1$H; 149.9, 135.5 and 123.5 ppm for $^{13}$C.

Exact mass measurements were performed on a Waters LCT Premier XE TOF equipped with an electrospray ionization interface and coupled to a Waters Alliance high performance liquid chromatography (HPLC) system. Samples were infused in a CH$_3$CN/HCOOH (1000:1) mixture at a rate of 10 mL/minute.

Detailed Procedure for the Synthesis of Carbamate-containing Galacto-pyranosyl Compounds from an Appropriate Isocyanate (2a-2b)

To a solution of compound 1 (0.07 mmole) in DMF (1 mL) was added the appropriate isocyanate (0.18 mmole), respectively 4-chlorophenyl isocyanate and 1-naphthyl isocyanate). After stirring overnight, the reaction mixture was evaporated to dryness under reduced pressure. Purification by means of column chromatography (hexanes/ethyl acetate (EtOAc) mixture: 8/2) afforded carbamates 2a (74% yield) and 2b (67% yield) respectively.

Detailed Procedure for the Synthesis of Carbamate-containing Galacto-pyranosyl Compounds from an Appropriate Amine and CDI (2c)

To a solution of compound 1 (50 mg, 0.04 mmol) in DMF (0.5 mL) was added 1,1'-carbonyldiimidazole (CDI) (31 mg, 0.18 mmol). After stirring overnight, the reaction mixture was heated until the temperature reached 70° C. and then 4-aminopyridine was added. The reaction mixture was stirred at 70°

C. during 48 hours followed by evaporation to dryness under reduced pressure. Purification by column chromatography (hexanes/EtOAc mixture: 7/3) afforded the carbamate 2c (26 mg, 33% yield).

(2S,3S,4R)-3,4-di-O-benzyl-1-O-(2,3,4-tri-O-benzyl-6-O-(4-chlorophenylcarbamoyl)-α-D-calactopyranosyl)-2-hexacosylamino-octadecane-1,3,4-triol (2a) was Characterized as Follows:

$^1$H NMR (300 MHz, CDCl$_3$): δ 8.29 (s, 1H, NH), 7.31-7.10 (m, 29H, arom. H), 5.71 (d, J=6.6 Hz, 1H, NH), 4.88 (d, J=11.6 Hz, 1H, CH$_2$—Ph), 4.79 (d, J=3.9 Hz, 1H, H-1"), 4.75 (d, J=11.6 Hz, 1H, CH$_2$—Ph), 4.67 (d, J=12.0 Hz, 1H, CH$_2$—Ph), 4.61 (d, J=11.8 Hz, 1H, CH$_2$—Ph), 4.62 (d, J=11.9 Hz, 1H, CH$_2$—Ph), 4.57 (d, J=11.6 Hz, 1H, CH$_2$—Ph), 4.52 (d, J=11.4 Hz, 1H, CH$_2$—Ph), 4.51 (d, J=11.8 Hz, 1H, CH$_2$—Ph), 4.42 (d, J=11.6 Hz, 1H, CH$_2$—Ph), 4.41 (d, J=11.6 Hz, 1H, CH$_2$—Ph), 4.33-4.26 (m, 2H, H-2, H-6"), 4.01-3.90 (m, 3H, H-2", H-1), 3.86-3.75 (m, 4H, H-3, H-3", H-4", H-5"), 3.69 (dd, J=1.6 and 11.4 Hz, 1H, H-6"), 3.51-3.46 (m, 1H, H-4), 1.96-1.84 (m, 2H, COCH$_2$), 1.58-1.06 (m, 72H, CH$_2$), 0.77 (t, J=6.9 Hz, 6H, CH$_3$);

$^{13}$C NMR (75 MHz, CDCl$_3$): δ 173.93, 153.51, 138.79, 138.73, 138.69, 138.47, 138.22, 137.63, 129.90, 128.96, 128.68, 128.64, 128.60, 128.57, 128.13, 128.04, 127.99, 127.90, 127.84, 127.73, 127.66, 119.69, 100.52, 80.54, 79.72, 79.48, 77.67, 77.45, 77.25, 76.83, 76.65, 75.20, 74.52, 73.88, 73.66, 73.62, 72.38, 70.26, 70.17, 65.87, 60.62, 52.34, 37.04, 32.17, 32.16, 30.88, 29.97, 29.96, 29.94, 29.92, 29.89, 29.79, 29.61, 29.60, 29.48, 26.17, 25.81, 22.93, 21.28, 14.43, and 14.36 ppm; and Exact mass (ESI-MS) for C$_{92}$H$_{133}$ClN$_2$O$_{10}$ [M+H]$^+$ found, 1461.9786; calculated, 1461.9727.

(2S,3S,4R)-3,4-di-O-benzyl-1-O-(2,3,4-tri-O-benzyl-6-O-(4-pyridinylcarbamoyl)-α-D-galactopyranosyl)-2-hexacosylamino-octadecane-1,3,4-triol (2b) was Characterized as Follows:

$^1$H NMR (300 MHz, pyridine-d$_5$): δ 10.66 (s, 1H, NH), 8.99 (d, J=8.4 Hz, 1H, NH), 8.84 (d, J=8.4 Hz, 1H, arom. H), 8.37 (d, J=7 Hz, 1H, arom. H), 7.96 (d, J=7.9 Hz, 1H, arom. H), 7.78 (d, J=8.1 Hz, 1H, arom. H), 7.66-7.29 (m, 26H, arom. H), 5.43 (d, J=3.4 Hz, 1H, H-1"), 5.17 (d, J=11.1 Hz, 1H, CH$_2$—Ph), 5.13 (d, J=10.2 Hz, 1H, CH$_2$—Ph), 5.00-4.82 (m, 4H, CH$_2$—Ph , H-6", H-2), 4.78-4.68 (m, 5H, H-6", CH$_2$—Ph), 4.64-4.58 (m, 2H, H-5", CH$_2$—Ph), 4.54 (dd, J=2.0 and 8.4 Hz, 1H, H-3), 4.48-4.43 (m, 3H, H-1, H-2", CH$_2$—Ph), 4.34 (dd, J=2.7 and 10.2 Hz, 1H, H-3"), 4.25-4.20 (m, 2H, H-1, H-4"), 3.97-3.93 (m, 1H, H-4), 2.66-2.56 (m, 2H, COCH$_2$), 2.15-1.18 (m, 72H, CH$_2$), 0.90 (t, J=6.7 Hz, 3H, CH$_3$), 0.89 (t, J=6.4 Hz, 3H, CH$_3$);

$^{13}$C NMR (75 MHz, pyridine-d$_5$): δ 172.21, 154.34, 138.55, 138.41, 138.21, 138.12, 127.65, 127.50, 127.29, 126.89, 126.80, 126.75, 126.58, 125.16, 125.11, 97.63, 80.00, 78.76, 77.89, 76.09, 74.88, 73.94, 73.24, 72.26, 71.67, 70.70, 68.77, 61.38, 50.13, 49.97, 48.02, 38.95, 35.66, 34.03, 30.97, 28.99, 28.87, 28.80, 28.74, 28.66, 28.43, 25.62, 25.27, 23.71, 21.78, and 13.12 ppm; and Exact mass (ESI-MS) for C$_{96}$H$_{136}$N$_2$O$_{10}$ [M+H]$^+$ found, 1478.0220; calculated, 1478.0273.

(2S,3S,4R)-3,4-di-O-benzyl-1-O-(2,3,4-tri-O-benzyl-6-O-(4-pryridinylcarbamoyl)-α-D-galactopyranosyl)-2-hexacosylamino-octadecane-1,3,4-triol (2c) was Characterized as Follows:

$^1$H NMR (300 MHz, CDCl$_3$): δ 7.87 (s, 1H, NH), 7.35-7.15 (m, 28H, arom. H), 6.93 (s, 1H, arom. H), 5.69 (d, J=8.2 Hz, 1H, NH), 4.90 (d, J=11.7 Hz, 1H, CH$_2$—Ph), 4.81 (d, J=3.7 Hz, 1H, H-1"), 4.76 (d, J=11.1 Hz, 1H, CH$_2$—Ph), 4.73 (d, J=11.3 Hz, 1H, CH$_2$—Ph), 4.69 (d, J=11.3 Hz, 1H, CH$_2$—Ph), 4.65 (d, J=11.7 Hz, 1H, CH$_2$—Ph), 4.58 (d, J=11.7 Hz, 1H, CH$_2$—Ph), 4.55 (d, J=11.7 Hz, 1H, CH$_2$—Ph), 4.48 (d, J=11.7 Hz, 1H, CH$_2$—Ph), 4.40 (d, J=11.7 Hz, 1H, CH$_2$—Ph), 4.39 (d, J=11.5 Hz, 1H, CH$_2$—Ph), 4.29-4.20 (m, 2H, H-2, H-6"), 4.12-4.06 (m, 1H, H-6"), 3.99 (dd, J=3.3 and 9.8 Hz, 1 H, H-2"), 3.94 (m, 1 H, H-5"), 3.85 (dd, J=2.5 and 10.1 Hz, 1H, H-3"), 3.81 (dd, J=4.91 and 11.0 Hz, 1H, H-1), 3.75 (app. s, 1H, H-4"), 3.68-3.64 (m, 1H, H-3), 3.62-3.56 (m, 1H, H-1), 3.48-3.43 (m, 1H, H-4), 1.86-1.74 (m, 2H, COCH$_2$), 1.54-1.09 (m, 72H, CH$_2$), 0.83-0.76 (m, 6H, CH$_3$);

$^{13}$C NMR (75 MHz, CDCl$_3$): δ 173.09, 148.33, 138.68, 138.62, 138.52, 138.01, 137.32, 130.68, 128.76, 128.73, 128.68, 128.66, 128.64, 128.60, 128.54, 128.16, 128.07, 128.05, 127.97, 127.82, 127.78, 127.68, 117.33, 99.09, 80.11, 79.67, 79.13, 74.56, 73.83, 73.48, 72.12, 68.33, 68.16, 66.68, 60.63, 56.66, 50.42, 36.97, 32.16, 31.82, 30.51, 30.04, 29.96, 29.93, 29.89, 29.84, 29.67, 29.64, 29.60, 29.59, 26.02, 25.94, 22.92, 22.88, 21.27, 14.22 and 14.35 ppm; and Exact mass (ESI-MS) for C$_{89}$H$_{131}$N$_3$O$_{10}$ [M+H]$^+$ found, 1402.9974; calculated, 1402.9907.

Procedure for Debenzylation (3a-c)

A solution of the protected carbamate (0.03 mmole) in CHCl$_3$ (0.4 mL) and EtOH (1.2 mL) was hydrogenated under atmospheric pressure in the presence of palladium black (10 mg). Upon completion of the reaction, the mixture was diluted with pyridine and filtered through Celite. The filter cake was rinsed with CHCl$_3$ and EtOH and the filtrate was evaporated to dryness. After purification by column chromatography (CH$_2$Cl$_2$/MeOH mixture: 28/2), the final compounds 3a (81% yield), 3b (88% yield) and 3c (86% yield) were respectively obtained.

(2S,3S,4R)-1-O-(6-O-(4-chlorophenylcarbamoyl)-α-D-galactopyranosyl)-2-hexacosylamino-octadecane-1,3,4-triol (3a) was Characterized as Follows:

$^1$H NMR (300 MHz, pyridine-d$_5$): δ 10.73 (s, 1H, NH), 8.58 (d, J=8.2 Hz, 1H, NH), 7.91 (d, J=8.7 Hz, 2H, arom. H), 7.40 (d, J=8.9 Hz, 2H, arom. H), 6.99 (br. s, 1 H, OH), 6.75 (br. s, 1 H, OH), 6.62 (d, J=3.7 Hz, 1H, OH), 6.45 (d, J: 6.6 Hz, 1H, OH), 6.27 (d, J=6.8 Hz, 1H, OH), 5.51 (d, J=3.9 Hz, 1H, H-1"), 5.21-5.18 (m, 1H, H-2), 5.03 (dd, J=8.1 and 11.0 Hz, 1 H, H-6"), 4.79 (dd, J=3.54 and 11.0 Hz, 1 H, H-6"), 4.66-4.57 (m, 3H, H-1, H-2", H-5"), 4.39-4.24 (m, 5H, H-3", H-4", H-1, H-3, H-4), 2.46 (t, J=7.5 Hz, 2H, COCH$_2$), 1.98-1.18 (m, 72H, CH$_2$), 0.88 (t, J=6.3 Hz, 6H, CH$_3$);

$^{13}$C NMR (75 MHz, pyridine-d$_5$): δ 172.33, 153.39, 138.14, 128.14, 128.05, 126.14, 119.21, 100.24, 74.89, 71.53, 70.08, 69.72, 69.27, 68.86, 67.57, 64.78, 50.50, 35.64, 32.88, 30.96, 30.94, 29.31, 29.18, 28.98, 28.87, 28.84, 28.76, 28.74, 28.70, 28.63, 28.57, 28.45, 28.43, 25.37, 25.18, 21.77 and 13.11; and Exact mass (ESI-MS) for C$_{57}$H$_{103}$ClN$_2$O$_{10}$ [M+H]$^+$ found, 1011.7393; calculated, 1011.7374.

(2S,3S,4R)-1-O-(6-O-(1-naphthylcarbamoyl)-α-D-galactopyranosyl)-2-hexa-cosylamino-octadecane-1,3,4-triol (3b) was Characterized as Follows:

$^1$H NMR (300 MHz, pyridine-d$_5$): δ 10.68 (s, 1H, NH), 8.74-8.70 (m, 1H, arom H)), 8.58 (d, J=8.6 Hz, 1H, NH), 8.26 (d, J=7.3 Hz, 1H, arom. H), 7.94 (d, J=7.5 Hz, 1H, arom. H), 7.74 (d, J=8.4 Hz, 1H, arom. H), 7.62-7.51 (m, 3H, arom. H), 5.58 (d, J=3.9 Hz, 1H, H-1"), 5.28-5.22 (m, 1H, H-2), 5.17-5.06 (m, 1H, H-6"), 4.94 (dd, J=4.2 and 11.2 Hz, 1H, H-6"), 4.84-4.65 (m, 3H, H-1, H-5", H-2"), 4.48-4.37 (m, 4H, H-1, H-3, H-3", H-4"), 4.33-4.28 (m, 1H, H-4), 2.51-2.46 (m, 2H, COCH$_2$), 1.93-1.23 (m, 72H, CH$_2$), 0.91-0.86 (m, 6H, CH$_3$);

$^{13}$C NMR (75 MHz, pyridine-d$_5$): δ 172.27, 154.65, 149.43, 135.00, 133.63, 127.56, 125.15, 125.11, 125.04, 123.71, 100.24, 75.11, 71.50, 70.10, 69.75, 69.29, 68.90, 64.83, 50.45, 35.66, 30.95, 30.94, 29.19, 28.95, 28.86, 28.83, 28.76, 28.74, 28.68, 28.62, 28.58, 28.45, 28.43, 25.32, 25.22, 21.76 and 13.10 ppm; and Exact mass (ESI-MS) for $C_{61}H_{106}N_2O_{10}$ [M+H]$^+$ found, 1027.7919; calculated, 1027.7926.

(2S,3S,4R)-1-O-(6-O-(4pyridinylcarbamoyl)-α-D-galactopyranosyl)-2-hexa-cosylamino-octadecane-1,3,4-triol (3c) was Characterized as Follows:

$^1$H NMR (300 MHz, pyridine-d$_5$): δ 11.18 (s, 1H, NH), 8.83 (d, J=8.3 Hz, 1H, NH), 8.67 (dd, J=1.4 and 4.8 Hz, 2H, arom. H), 7.93 (dd, J=1.4 and 4.8 Hz, 2H, arom. H), 5.55 (d, J=3.8 Hz, 1H, H-1"), 5.26-5.20 (m, 1H, H-2), 5.08 (dd, J=8.2 and 11.0 Hz, 1H, H-6"), 4.77 (dd, J=3.4 and 11.0 Hz, 1H, H-6"), 4.72-4.62 (m, 3H, H-1, H-2", H-5"), 4.45-4.30 (m, 5H, H-3", H-4", H-1, H-3, H-4), 2.53 (t, J=7.5 Hz, 2H, COCH$_2$), 1.95-1.23 (m, 72H, CH$_2$), and 0.88 (t, J=6.5 Hz, 6H, CH$_3$);

Exact mass (ESI-MS) for $C_{56}H_{103}N_3O_{10}$ [M+H]$^+$ found, 978.7662; calculated, 978.7722.

EXAMPLE 2

In vivo Stimulation in Mice

Materials and methods for this biological assay were as follows:

Glycolipids from this invention were synthesized according to the procedure of example 1. α-C-GalCer was kindly provided by Aaron Diamond AIDS Research Center (New York, USA) and the NIH Tetramer Core Facility. Lyophilized glycolipids were dissolved in pure dimethylsulfoxide (DMSO) (Sigma) at a 10 mg/mL concentration and stored at −20° C. Glycolipids were solubilized by adding phosphate buffer saline (PBS) (Invitrogen) or a standard vehicle (96 mg/mL sucrose, 10 mg/mL sodium deoxycholate, 0,05% Tween 20), warming to 80° C. for 20 minutes, and then sonication for 10 minutes.

Cell Lines

The murine iNKT hybridoma N38-2C12 (Vα14Vβ8.1/8.2b) was provided by Brown University, Providence, Rhode Island, USA). Cells were cultured in DMEM Sigma) supplemented with 10% fetal calf serum (Invitrogen), 1% glutamine (Sigma), 1% penicillin streptomycin (Sigma), and 2-mercapto-ethanol (Sigma) (hereinafter called cDMEM). B16 melanoma cells were cultured in advanced RPMI (Sigma) supplemented with 10% fetal calf serum (Invitrogen), 1% glutamine (Sigma) and 1% penicillin streptomycin (Sigma). They were harvested using cell dissociation buffer, which was washed away twice first using the medium and second with PBS. 400,000 cells were intravenously (IV) injected within 30 minutes after harvest into the tail vein.

Isolation and Expansion of BMDC

BMDC were isolated from the mouse bone marrow as described previously.

Mice

C57BL/6 and CD45.1 mice were in house bred (in accordance with the general recommendations for animal breeding and housing) or purchased from the Harlan Laboratory, Jα18-knockout mice on the C57BL/6 background were kindly provided by RIKEN (Tsurumi, Yokohama, Japan). Experiments were conducted according to the guidelines of the Ethical Committee of Laboratory Animals Welfare of Ghent University (Belgium). Mice used for experiments were between 5 and 12 weeks old.

In vitro and in vivo Activation of iNKT Cells

For in vitro stimulation, murine iNKT hybridoma cells at $5·10^4$ cells/well in 96-well plates were stimulated with the $10^5$ cells/well glycolipid pulsed BMDCs in cDMEM for 4, 16 or 24 hours at 3TC, and levels of murine IL-2 secretion were determined by ELISA.

For in vivo activation of iNKT cells C57BL/6 mice were either intraperitoneally injected with 5 μg glycolipid (dissolved in PBS) or intravenously with $6·10^5$ or $1·10^4$ glycolipid pulsed BMDCs.

Isolation of Human PBMC and iNKT Cells

Human iNKT cells from healthy adult individuals were sorted and expanded. PBMCs were isolated by means of density centrifugation, incubated overnight in the presence of indicated glycolipids (100 ng/ml), washed and irradiated (40 Gy). Subsequently, $5×10^4$ iNKT cells were stimulated with $10^5$ glycolipid pulsed autologous PBMCs in RPMI 1640 media supplemented with 10% human AB serum (Lonza), 1% sodium pyruvate, 1% nonessential amino acids and 1% penicillin/streptomycin (all from Invitrogen). Supernatants were collected after 24 hours of culture and cytokine levels were determined by means of cytometric Bead Arrays (CBA) following the manufacturer's instructions (BD).

Isolation of Murine Lymphocytes

Spleen cells were isolated. Lymphocytes were isolated at the interface and washed, depleted with an anti-CD3 kit (Miltenyi Biotec, Sunnyvale, Canada) and re-suspended in a staining buffer containing saturating amount of anti-Fcγ Receptor type II/type III monoclonal antibodies (Miltenyi). Hereafter cells were stained with fluorochrome-conjugated mAbs (all from Bioscience) directed against the described antigens. Live cells (exclusion with DAPI) were acquired on a FACSCanto (BD) flow cytometer and analyzed using FlowJo (Tree Star) software.

Surface Plasmon Resonance (SPR) Experiments

SPR studies were conducted using a Biacore 3000 (Biacore). Glycolipids were dissolved at 1 mg/ml in DMSO and before loading were diluted to 0.25 mg/ml with vehicle solution (50 mM Tris-HCl pH 7.0, 4.8 mg/ml sucrose, 0.5 mg/ml deoxycholate and 0.022% Tween-20), heated for 20 minutes at 80° C. After cooling 1 μg of each lipid was incubated with 10 μg enzymatically biotinylated mCD1d overnight at room temperature. In one embodiment, 400-600 response units (RU) of mCD1d-glycolipid complexes were immobilized onto a CA capture chip (Biacore). A reference surface was generated in another flow channel with unloaded mCD1d immobilized at RU of 500. During the association phase, a series of increasing concentrations of TCR (in 10 mM HEPES, 150 mM NaCl, 3.0 mM EDTA, pH 7.4) in duplicate were injected for 80 seconds and the dissociation phase (running buffer only) was monitored over 45 minutes. Experiments were carried out at 25° C. with a flow rate of 30 μl/min and performed at least two to three times, each time with a different batch of TCR preparation. Kinetic parameters were calculated after subtracting the response to mCD1d molecules in the reference channel, using a simple Langmuir 1:1 model in the BIA evaluation software version 4.1. One representative sensorgram for each lipid is shown.

In an alternative embodiment, 500-600 RU of the mCD1d-glycolipids complexes were captured on a streptavidin sensor chip surface (GE Healthcare). TCR protein was diluted in detergent-free running buffer (10 mM Hepes, 150 mM NaCl, and 3 mM EDTA, pH 7.4). The TCR was injected in serial dilutions (0, 0.0156-2 μM) for 1.5-3 minutes at 30 μl/minute to measure the association phase, while dissociation was continued for 45 minutes at 25° C. A reference surface containing "empty" CD1d was generated in flow channel one of the streptavidin sensor chip and its TCR binding response was subtracted from the other sensorgrams before calculating binding kinetics using a simple Langmuir 1:1 model in the BIA evaluation software version 4.1. Experiments were performed three times, each using a different TCR preparation.
Statistical Analysis The statistical test used throughout this study was Kruskal-Wallis test with Dunn's multiple comparison test or Mann Whitney U test (unpaired, two-sided) unless otherwise stated. Data was analyzed using Excel (Microsoft) and Graphpad Prism 5.

Figure 8:
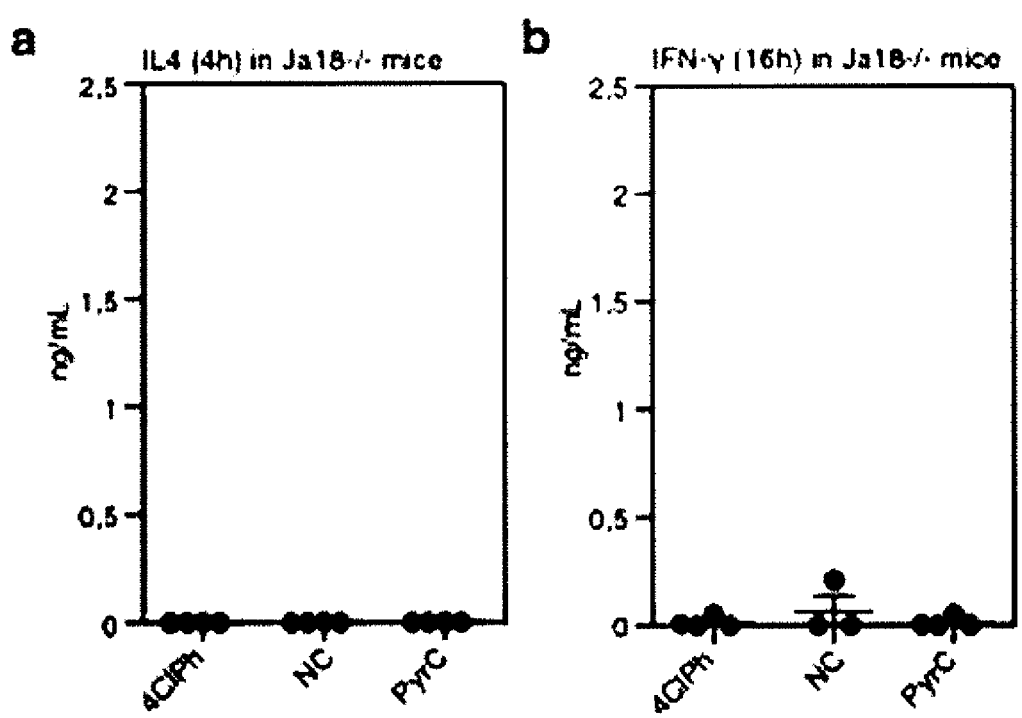
FIG. 8 shows data of IL-4 secretion 4 hours (a) and IFN-γ secretion 16 hours after injection of 5 μg glycolipid in mice lacking iNKT (Jα18–/–) cells for three representative galactopyranosyl compounds of the present invention (NC-α-GalCer, 4ClPhC-α-GalCer, and PyrC-α-GalCer).

In order to assess the antigenicity of the carbamate-containing galactopyranosyl compounds of example 1 and their ability to induce Th1-skewing, mice were bled at 16 hours after intraperitoneal glycolipid exposure because this is known to afford peak levels of IFN-y, the hallmark Th1 cytokine. Strikingly, all carbamate-linked glycolipids induced significantly higher IFN-γ levels than NU-α-GalCer and α-GalCer (FIG. 1). In this setting, NU-α-GalCer induced comparable or slightly lower IFN-γ production compared to α-GalCer. IFN-y production in response to glycolipid dependent iNKT cell activation is known to be dependent on IL-12[10-12], which was therefore analyzed. As expected also IL-12 production was significantly higher for the carbamate-based glycolipids compared to α-GalCer. However, only PyrC-α-GalCer was capable of inducing significantly higher IL-12 levels than NU-α-GalCer. Administration of these novel glycolipids to Jα18−/− mice, which lack iNKT cells, did not induce any cytokine production, thereby excluding non-specific effects (FIG. 8).

Figure 2:
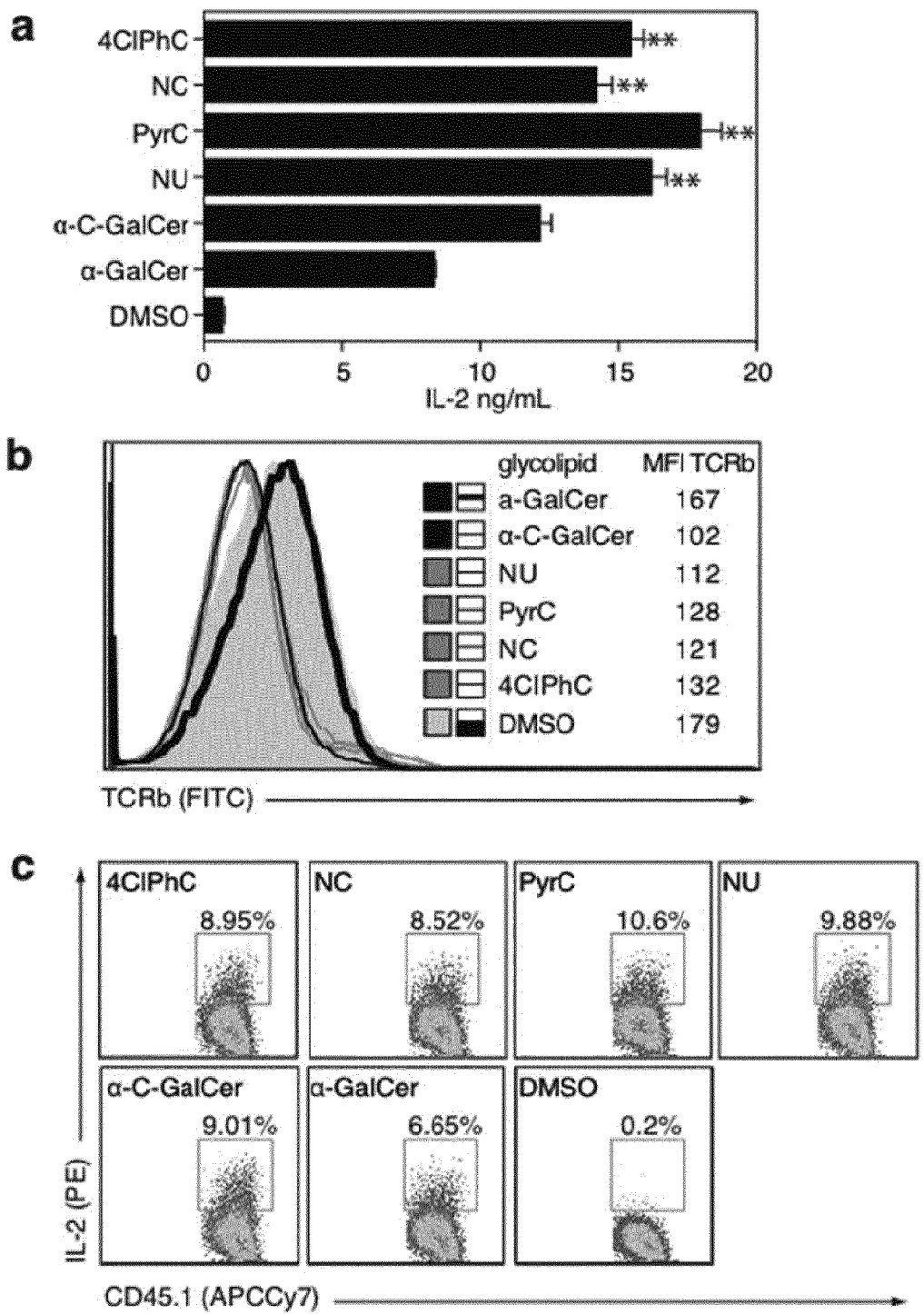
FIG. 2 shows (a) IL-2 production as measured by ELISA after 16 hours co-culture with an iNKT cell line 2C12; (b) TCRb expression by the iNKT cell line 2C12 24 hours after co-culture with the glycolipid-pulsed CD45.1 bone marrow-derived dendritic cells (BMDC); (c) intracellular IL-2 production by 2C12 cells, 4 hours after co-culture. In each set-up three representative galactopyranosyl compounds of the present invention (NC-α-GalCer, 4ClPhC-α-GalCer, and PyrC-α-GalCer) are compared with α-GalCer itself, its naphthylurea derivative NU-α-GalCer, and DMSO as a standard reference.

TCR Affinity and Stability of the CD1d-glycolipid Complex iNKT cell polarization is a matter of debate and it has been shown uptake by different cells can also affect the outcome. To avoid these host dependent parameters we set up a simple in vitro model, which consists of co-cultures of glycolipid-pulsed bone marrow dendritic cells and an iNKT cell hybridoma (i.c. 2C12 containing a Vβ8.2 TCR). IL-2 production is used as a read-out for TCR affinity for the whole CD1d-glycolipid complex. Here the carbamates, NU-α-GalCer and α-C-GalCer induce higher IL-2 levels (FIG. 2). To confirm this we also measured intracellular IL-2 production in 2C12 cells already 4 hours after coculture, where a similar result was obtained (FIG. 2). Because IL-2 production is a downstream event of TCR signaling we analyzed TCRβ expression. FIG. 2 suggests that TCR internalization occurs in vitro and correlates well with the intracellular IL-2 production.

However IL-2 production and TCR triggering are the result of both molecular TCR affinity and CD1d stability. Surface plasmon resonance data show a similar $K_D$ for all tested 6"OH-altered glycolipids (33-75 nM), slightly weaker compared to α-GalCer (11 nM). Thus in contrast to BnNH-GSL-1' the glycolipid presentation by CD1d and/or the glycolipid interaction with the TCR is not significantly affected by the presence of carbamate linked aromatic groups. However, 4ClPhC-α-GalCer shows with 75 nM a 6-fold reduced affinity compared to α-GalCer and this appears to be the result of the 4Cl modification of the phenyl group, as the same compound lacking the Cl atom, PyrC-α-GalCer has the highest affinity of the three tested compounds (33 nM).

Figure 3:
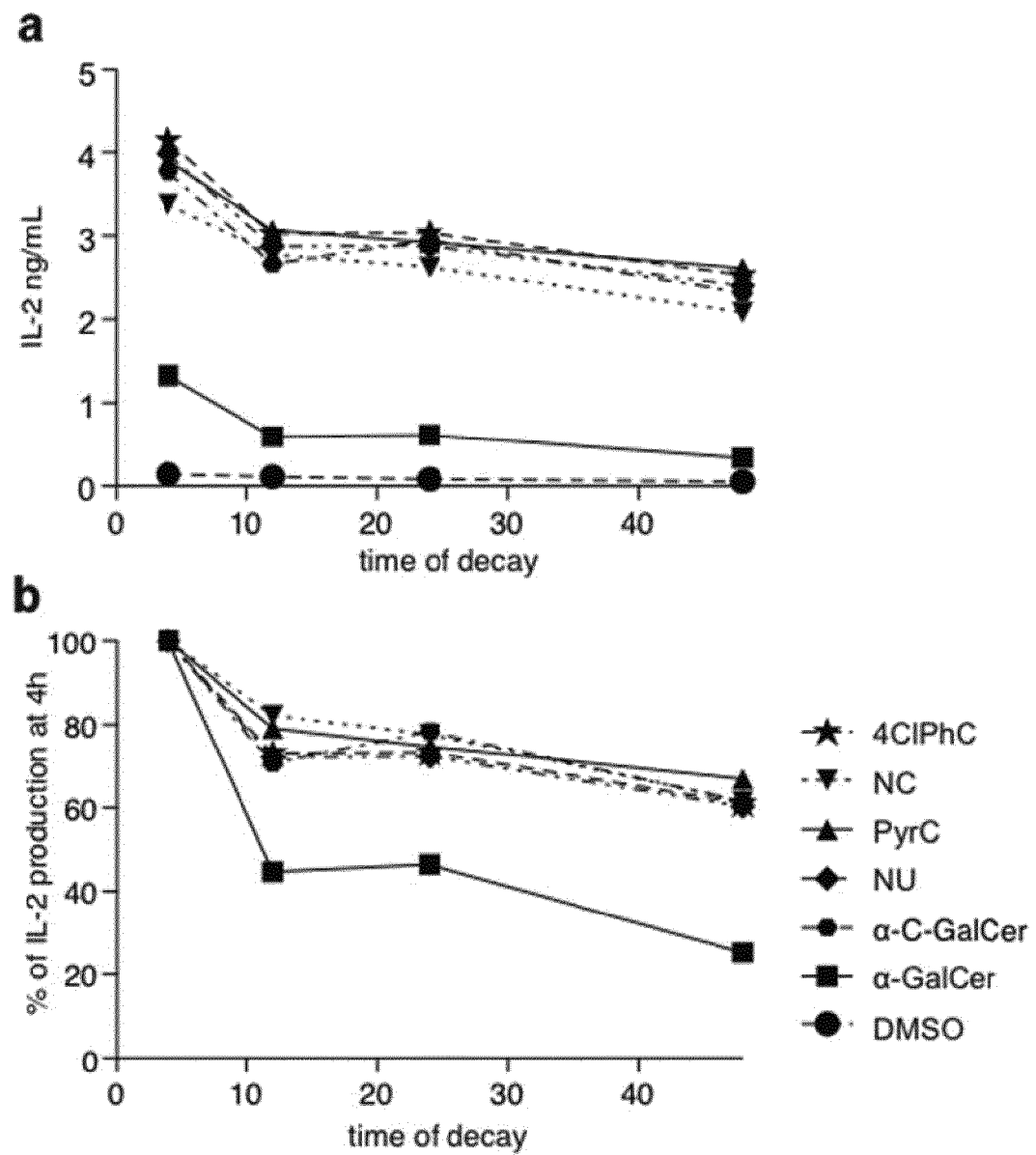
FIG. 3 shows (a) IL-2 production after loading BMDC during 20 hours with 100 ng/mL glycolipid, then washing the glycolipid, and leaving cells in appropriate medium for the time intervals (4 hours, 12 hours, 24 hours and 48 hours) shown on the X-axis; (b) data from (a) normalized to the 4 hours time point, representing the stability of each glycolipid towards CD1d. Three representative galactopyranosyl compounds of the present invention (NC-α-GalCer, 4ClPhC-α-GalCer, and PyrC-α-GalCer) are compared with α-GalCer itself, its naphthylurea derivative NU-α-GalCer, and DMSO as a standard reference.

Secondly, we investigated the role of CD1d-glycolipid stability. We used a cellular assay to determine the binding stability of the novel glycolipids. Bone marrow dendritic cells were loaded with 100 ng/mL glycolipid during 20 hours. After removal of the free glycolipid, cells were left in appropriate medium for several time intervals (ranging from 4 hours to 48 hours). Again dissociated glycolipid was removed and co-culture with 2C12 cells was initiated. IL-2 production in the medium was used as a surrogate marker for remaining CD1d with glycolipid. The strong Th1 polarizing α-C-GalCer, characterized by a higher binding stability to CD1d, was also included into this assay. IL-2 data were normalized to the values of 4 hours of wash off to exclude the effect of TCR affinity. FIG. 3B shows very clearly that all 6'-OH analogs and α-C-GalCer behave very similarly and have a much slower decay compared to α-GalCer. So we conclude that all tested Th1 analogs have a similar stability with CD1 d in vitro, which is much higher than for the CD1d-α-GalCer complex.

Carbamate-pulsed BMDC Confer to Strong Anti-metastatic Potential

Figure 4:
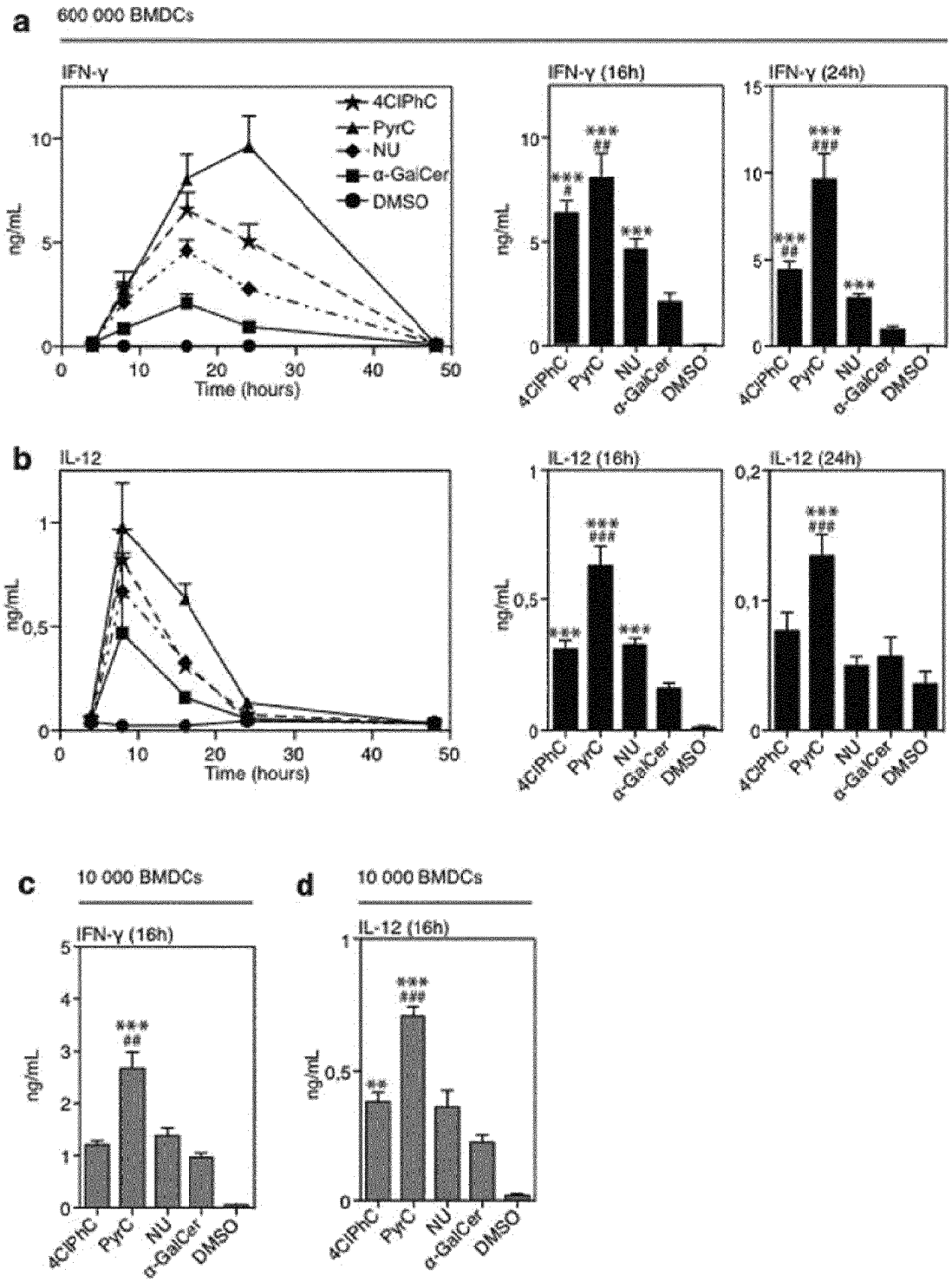
FIG. 4 shows IFN-γ levels (a) and IL-12 levels (b) at different time intervals (4 hours, 8 hours, 16 hours, 24 hours and 48 hours) after injection of a 100 ng/mL dose of glycolipid-pulsed BMDC; IFN-γ levels (c) and IL-12 levels (d) at 16 hours after injection of a 10000 glycolipid-pulsed BMDC. Three representative galactopyranosyl compounds of the present invention (NC-α-GalCer, 4ClPhC-α-GalCer, and PyrC-α-GalCer) are compared with α-GalCer, and DMSO as a standard reference.
Figure 5:
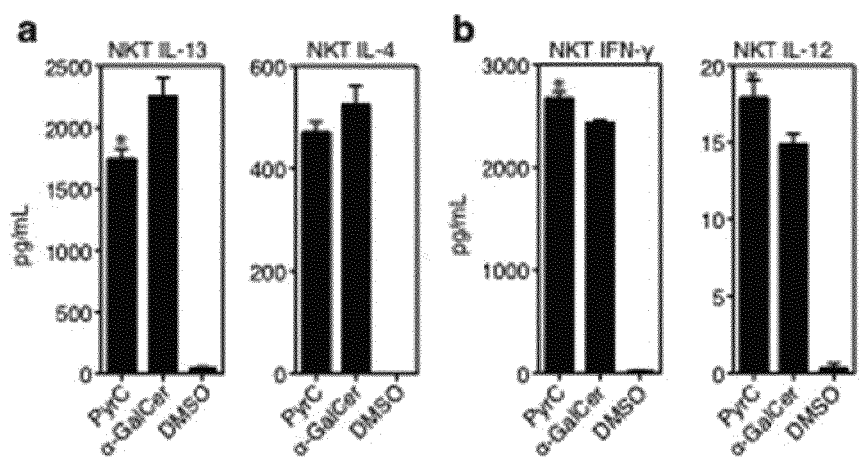
FIG. 5 shows production of IL-13 and IL-4 (a), IFN-γ and IL-12 (b) in human stimulated iNKT cells. One representative galactopyranosyl compound of the present invention (PyrC-α-GalCer) is compared with α-GalCer, and DMSO as a standard reference.

Next we examined if the glycolipid pulsed BMDC behave similarly in vivo. For cytokine analysis we bled the mice at several time points after injection. We focused on IFN-γ and IL-12 secretion. Again at 16 hours both carbamates induced a significantly higher IFN-γ secretion compared to NU-α-GalCer (which in this context is also significantly higher than α-GalCer) (FIG. 4). Strikingly for PyrC-α-GalCer the IFN-γ level increased up to 24 hours after injection in contrast to 4ClPhC-α-GalCer and NU-α-GalCer. Similarly IL-12 secretion was very high with PyrC-α-GalCer and even after 24 hours markedly higher than for NU-α-GalCer. Furthermore, PyrC-α-GalCer and the other 6"-OH altered glycolipids were also able to induce Th1-biased cytokine secretion (more IFN-γ and IL-12 and less IL-4 and IL-13 compared to α-GalCer) in cultures of purified human iNKT cells (FIG. 5). A similar trend was seen with human peripheral blood mononuclear cells (PBMCs) highlighting the conserved nature of the Th polarization.

Figure 6:
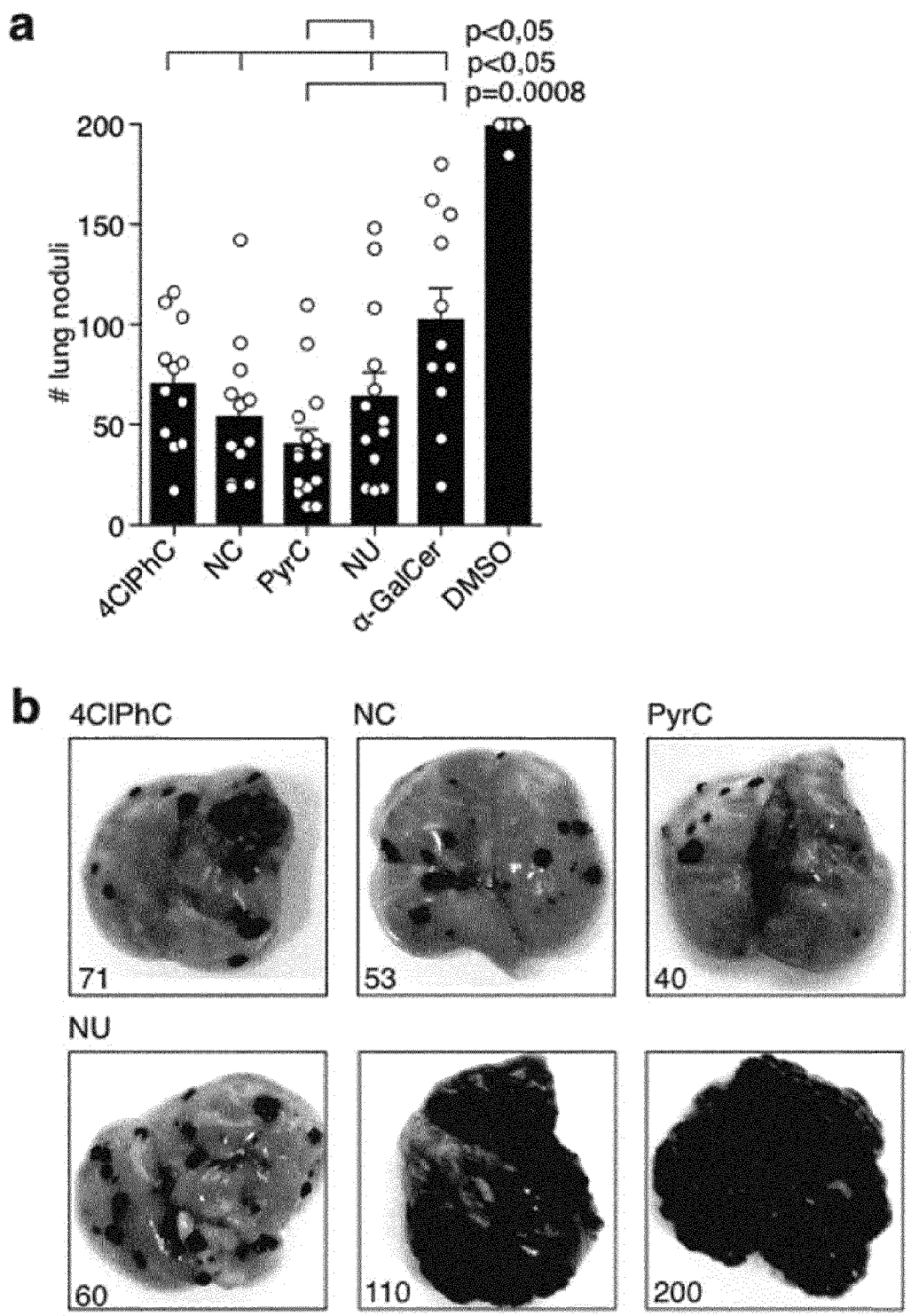
FIG. 6 shows results of tumor suppression by iNKT cell stimulation in a B16 melanoma lung metastasis model: (a) quantity of lung nodules after injection of 10 000 glycolipid-loaded BMDC, and (b) pictures of lungs used for analysis in (a). Three representative galactopyranosyl compounds of the present invention (NC-α-GalCer, 4ClPhC-α-GalCer, and PyrC-α-GalCer) are compared with α-GalCer itself, its naphthylurea derivative NU-α-GalCer, and DMSO as a standard reference.
Figure 9:
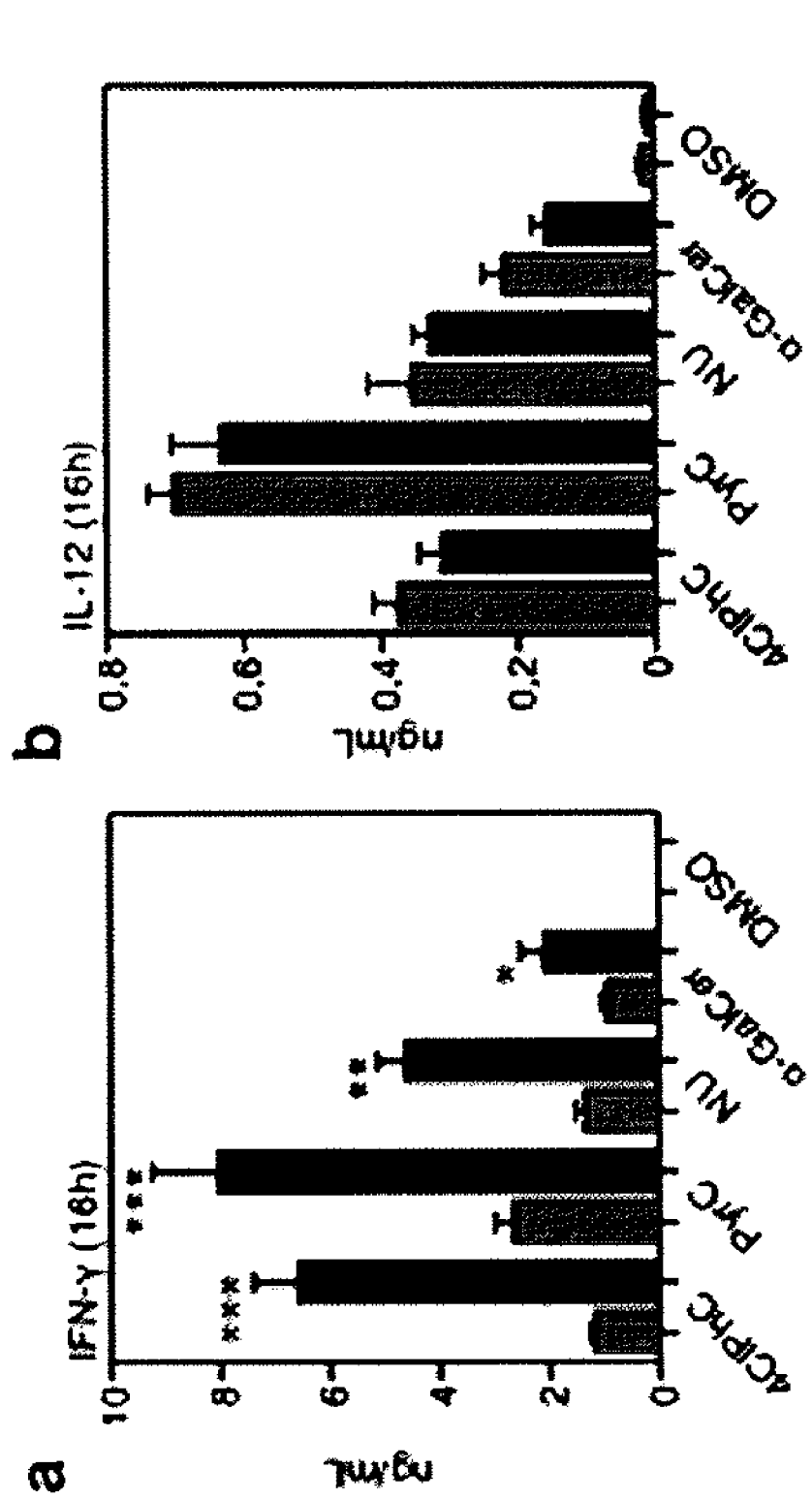
FIG. 9 shows the dose effect on Th1-Th2 profile: IFN-γ levels (a) and IL-12 levels (b) at 16 hours after injection of 10000 glycolipid-pulsed BMDC (grey, same data as in FIG. 4) or 600000 glycolipid-pulsed BMDC (black). Three representative galactopyranosyl compounds of the present invention (NC-α-GalCer, 4ClPhC-α-GalCer, and PyrC-α-GalCer) are compared with α-GalCer, and DMSO as a standard reference.
Figure 10:
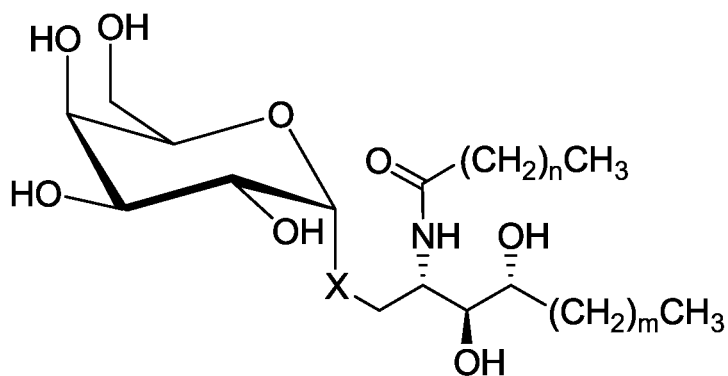
FIG. 10 schematically shows the structural formulae of various α-GalCer analogues of the prior art.
Figure 10:
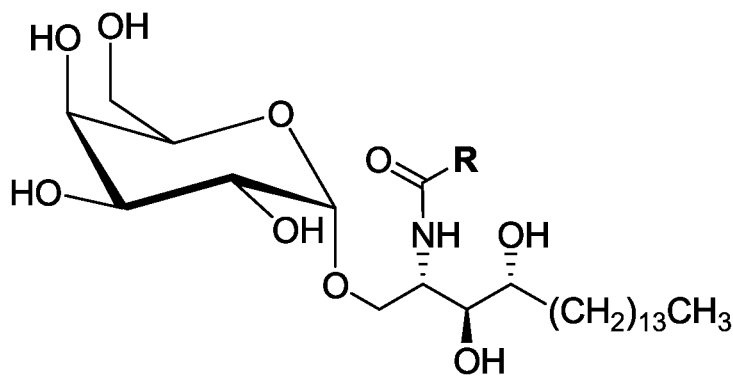

In order to determine if the new glycolipids can also mimic the anti-metastatic activity of NU-α-GalCer, we examined them in the B16 lung melanoma model. Even if NU-α-GalCer was significantly stronger compared to α-GalCer, PyrC-α-GalCer was still better in preventing tumor metastasis in the B16 lung model (FIG. 6). As little as 10,000 pulsed BMDC were enough to exert this marked tumor response. To analyze if these anti-tumor results still correspond to strong cytokine responses mice were bled 16 hours after injection of 10,000 pulsed bone marrow dendritic cells. Similar to the cytokine results with the high dose and the anti-metastatic results, PyrC-α-GalCer caused significantly higher IL-12 and IFN-γ production. Strikingly, the IL-12 results were not different between the 2 doses in contrast to the IFN-γ production, which was more dose-dependent (FIG. 9). This might indicate that other cytokines such as IL-18, which is also necessary for the induction of IFN-γ by NK cells might play an additional role in iNKT cell dependent Th1 polarization.

6'-OH Carbamate Analogues Markedly Modulate the Co-stimulatory Landscape

Figure 7:
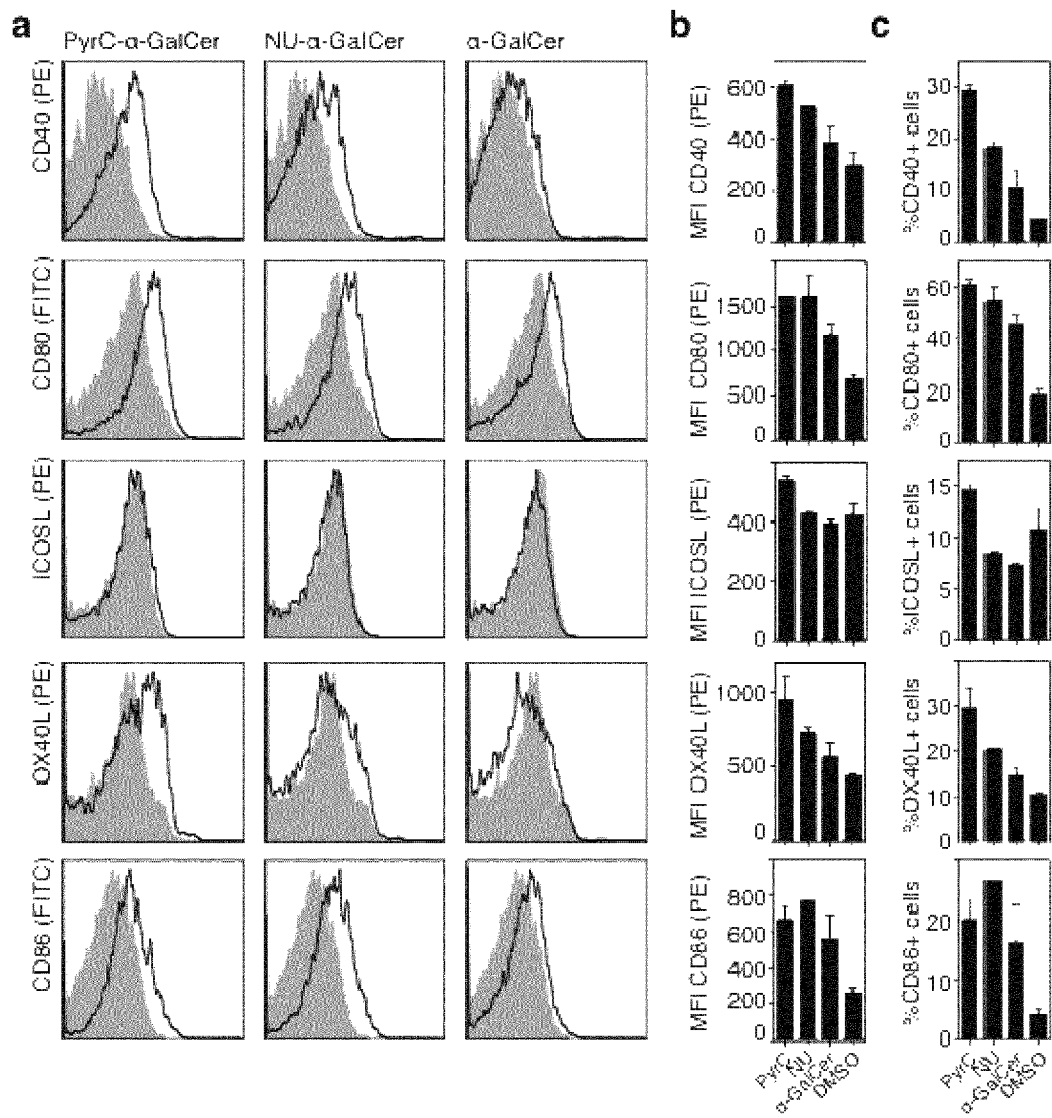
FIG. 7 shows the co-stimulatory effects of injecting 600000 glycolipid-pulsed BMDC in dendritic cells from spleens of C57/BL6 mice that were stained with antibodies against CD40, OX40L, ICOSL, CD80 and CD86: (a) co-stimulatory molecule expression was analyzed by gating on CD11c$^+$ CD11b$^+$ splenocytes. (b) graphs indicate the mean with s.e.m. of MFI for each costimulatory molecule. (c) Graphs indicate the mean percentage value of CD11c$^+$ CD11b$^+$ double positive splenocytes that are positive for each co-stimulatory molecule.

Expression of co-stimulatory markers at the cell surface is linked to cytokine polarization because this determines the degree of activation of by-stander cells such as NK cells, whose IFN-y production is responsible for Th1 polarized cytokine profile. For α-C-GalCer, it has been shown that expression of CD40 is essential for IL-12 and subsequent NK cell dependent IFN-γ production. In contrast, OCH, a Th2 polarizing antigen, is not able to induce CD40 expression at the surface of DCs. Additionally OX40L up-regulation by dendritic cells (DC) has been found important for α-GalCer dependent tumour killing. Here we show that PyrC-α-GalCer, which induces the highest levels of IL-12, induces early CD40 up-regulation on spleen DCs (CD11c CD11b double positive) both quantitatively and qualitatively (FIG. 7), emphasizing the importance of this co-stimulatory pathway for the production of IL-12 and its subsequent anti-tumor response.

Glycolipid stimulation of iNKT cells leads to CD28 expression, and induces CD80 and CD86 expression at the dendritic cell surface, which is required for induction of IL-12 by dendritic cells. This was confirmed here as all glycolipids induced up-regulation of both CD80 and CD86. In conclusion we herein demonstrate that the compounds of this invention induce a different pattern of co-stimulatory molecule expression, which is related to the induction of their superior Th1 profile.

EXAMPLE 3

Preparation of Related Carbamate-containing Galactopyranosyl Compounds

The following arylcarbamate-containing galactopyranosyl compounds are obtained whilst using the above described synthetic procedure for making compound 3b (example 1—, but replacing naphthyl isocyanate with another appropriate aryl isocyanate as described hereinabove:

(2S,3S,4R)-1-O-(6-O-(4-fluorophenylcarbamoyl)-α-D-galactopyranosyl)-2-hexacosylamino-octadecane-1,3,4-triol,
(2S,3S,4R)-1-O-(6-O-(3-fluorophenylcarbamoyl)-α-D-galactopyranosyl)-2-hexacosylamino-octadecane-1,3,4-triol,
(2S,3S,4R)-1-O-(6-O-(2-fluorophenylcarbamoyl)-α-D-galactopyranosyl)-2-hexacosylamino-octadecane-1,3,4-triol,
(2S,3S,4R)-1-O-(6-O-(phenylcarbamoyl)-α-D-galactopyranosyl)-2-hexacosylamino-octadecane-1,3,4-triol,
(2S,3S,4R)-1-O-(6-O-(3-methylphenylcarbamoyl)-α-D-galactopyranosyl)-2-hexacosylamino-octadecane-1,3,4-triol,
(2S,3S,4R)-1-O-(6-O-(4-methylphenylcarbamoyl)-α-D-galactopyranosyl)-2-hexacosylamino-octadecane-1,3,4-triol,
(2S,3S,4R)-1-O-(6-O-(2-trifluoromethylphenylcarbamoyl)-α-D-galactopyranosyl)-2-hexacosylamino-octadecane-1,3,4-triol,
(2S,3S,4R)-1-O-(6-O-(4-methoxyphenylcarbamoyl)-α-D-galactopyranosyl)-2-hexacosylamino-octadecane-1,3,4-triol,
(2S,3S,4R)-1-O-(6-O-(3-methoxyphenylcarbamoyl)-α-D-galactopyranosyl)-2-hexacosylamino-octadecane-1,3,4-triol,
(2S,3S,4R)-1-O-(6-O-(2-methoxyphenylcarbamoyl)-α-D-galactopyranosyl)-2-hexacosylamino-octadecane-1,3,4-triol,
(2S,3S,4R)-1-O-(6-O-(2-chlorophenylcarbamoyl)-α-D-galactopyranosyl)-2-hexacosylamino-octadecane-1,3,4-triol,
(2S,3S,4R)-1-O-(6-O-(3-chlorophenylcarbamoyl)-α-D-galactopyranosyl)-2-hexacosylamino-octadecane-1,3,4-triol,
(2S,3S,4R)-1-O-(6-O-(2,4-dichlorophenylcarbamoyl)-α-D-galactopyranosyl)-2-hexacosylamino-octadecane-1,3,4-triol,
(2S,3S,4R)-1-O-(6-O-(3,4-dichlorophenylcarbamoyl)-α-D-galactopyranosyl)-2-hexacosylamino-octadecane-1,3,4-triol,
(2S,3S,4R)-1-O-(6-O-(2,4-difluorophenylcarbamoyl)-α-D-galactopyranosyl)-2-hexacosylamino-octadecane-1,3,4-triol,
(2S,3S,4R)-1-O-(6-O-(2-trifluoromethoxyphenylcarbamoyl)-α-D-galactopyranosyl)-2-hexacosylamino-octadecane-1,3,4-triol,
(2S,3S,4R)-1-O-(6-O-(2,6-difluorophenylcarbamoyl)-α-D-galactopyranosyl)-2-hexacosylamino-octadecane-1,3,4-triol,
(2S,3S,4R)-1-O-(6-O-(2,5-difluorophenylcarbamoyl)-α-D-galactopyranosyl)-2-hexacosylamino-octadecane-1,3,4-triol,
(2S,3S,4R)-1-O-(6-O-(2-ethoxyphenylcarbamoyl)-α-D-galactopyranosyl)-2-hexacosylamino-octadecane-1,3,4-triol,
(2S,3S,4R)-1-O-(6-O-(4-ethoxyphenylcarbamoyl)-α-D-galactopyranosyl)-2-hexacosylamino-octadecane-1,3,4-triol,
(2S,3S,4R)-1-O-(6-O-(2-nitrophenylcarbamoyl)-α-D-galactopyranosyl)-2-hexacosylamino-octadecane-1,3,4-triol,
(2S,3S,4R)-1-O-(6-O-(4-nitrophenylcarbamoyl)-α-D-galactopyranosyl)-2-hexacosylamino-octadecane-1,3,4-triol,
(2S,3S,4R)-1-O-(6-O-(3-nitrophenylcarbamoyl)-α-D-galactopyranosyl)-2-hexacosylamino-octadecane-1,3,4-triol,
(2S,3S,4R)-1-O-(6-O-(4-tert-butylphenylcarbamoyl)-α-D-galactopyranosyl)-2-hexacosylamino-octadecane-1,3,4-triol,
(2S,3S,4R)-1-O-(6-O-(2-tert-butylphenylcarbamoyl)-α-D-galactopyranosyl)-2-hexacosylamino-octadecane-1,3,4-triol,
(2S,3S,4R)-1-O-(6-O-(4-isopropylphenylcarbamoyl)-α-D-galactopyranosyl)-2-hexacosylamino-octadecane-1,3,4-triol,
(2S,3S,4R)-1-O-(6-O-(2,6-diisopropylphenylcarbamoyl)-α-D-galactopyranosyl)-2-hexacosylamino-octadecane-1,3,4-triol,
(2S,3S,4R)-1-O-(6-O-(3-cyanophenylcarbamoyl)-α-D-galactopyranosyl)-2-hexacosylamino-octadecane-1,3,4-triol,
(2S,3S,4R)-1-O-(6-O-(2,4-dimethoxyphenylcarbamoyl)-α-D-galactopyranosyl)-2-hexacosylamino-octadecane-1,3,4-triol,
(2S,3S,4R)-1-O-(6-O-(2,6-dimethylphenylcarbamoyl)-α-D-galactopyranosyl)-2-hexacosylamino-octadecane-1,3,4-triol,
(2S,3S,4R)-1-O-(6-O-(4-dimethylaminophenylcarbamoyl)-α-D-galactopyranosyl)-2-hexacosylamino-octadecane-1,3,4-triol,
(2S,3S,4R)-1-O-(6-O-(3-methylthiophenylcarbamoyl)-α-D-galactopyranosyl)-2-hexacosylamino-octadecane-1,3,4-triol.

EXAMPLE 4

Preparation of Related Thiocarbamate-containing Galacto-Pyranosyl Compounds

The following compounds are obtained using the above synthetic procedure described for example 1, but replacing naphthyl isocyanate with an appropriate isothiocyanate as described hereinabove:

(2S,3S,4R)-1-O-(6-O-(4-chlorophenylthiocarbamoyl)-α-D-galactopyranosyl)-2-hexacosylamino-octadecane-1,3,4-triol,
(2S,3S,4R)-1-O-(6-O-(naphthylthiocarbamoyl)-α-D-galactopyranosyl)-2-hexacosylamino-octadecane-1,3,4-triol,
(2S,3S,4R)-1-O-(6-O-(4-fluorophenylthiocarbamoyl)-α-D-galactopyranosyl)-2-hexacosylamino-octadecane-1,3,4-triol,
(2S,3S,4R)-1-O-(6-O-(3-fluorophenylthiocarbamoyl)-α-D-galactopyranosyl)-2-hexacosylamino-octadecane-1,3,4-triol,
(2S,3S,4R)-1-O-(6-O-(2-fluorophenylthiocarbamoyl)-α-D-galactopyranosyl)-2-hexacosylamino-octadecane-1,3,4-triol, (2S,3S,4R)-1-O-(6-O-(phenylthiocarbamoyl)-α-D-galactopyranosyl)-2-hexacosylamino-octadecane-1,3,4-triol,
(2S,3S,4R)-1-O-(6-O-(3-methylphenylthiocarbamoyl)-α-D-galactopyranosyl)-2-hexacosylamino-octadecane-1,3,4-triol,
(2S,3S,4R)-1-O-(6-O-(4-methylphenylthiocarbamoyl)-α-D-galactopyranosyl)-2-hexacosylamino-octadecane-1,3,4-triol,
(2S,3S,4R)-1-O-(6-O-(2-trifluoromethylphenylthiocarbamoyl)-α-D-galactopyranosyl)-2-hexacosylamino-octadecane-1,3,4-triol,
(2S,3S,4R)-1-O-(6-O-(4-methoxyphenylthiocarbamoyl)-α-D-galactopyranosyl)-2-hexacosylamino-octadecane-1,3,4-triol,
(2S,3S,4R)-1-O-(6-O-(3-methoxyphenylthiocarbamoyl)-α-D-galactopyranosyl)-2-hexacosylamino-octadecane-1,3,4-triol,
(2S,3S,4R)-1-O-(6-O-(2-methoxyphenylthiocarbamoyl)-α-D-galactopyranosyl)-2-hexacosylamino-octadecane-1,3,4-triol,
(2 S,3S,4R)-1-O-(6-O-(2-chlorophenylthiocarbamoyl)-α-D-galactopyranosyl)-2-hexacosylamino-octadecane-1,3,4-triol,
(2 S,3S,4R)-1-O-(6-O-(3-chlorophenylthiocarbamoyl)-α-D-galactopyranosyl)-2-hexacosylamino-octadecane-1,3,4-triol,
(2S,3S,4R)-1-O-(6-O-(2,4-dichlorophenylthiocarbamoyl)-α-D-galactopyranosyl)-2-hexacosylamino-octadecane-1,3,4-triol,
(2S,3S,4R)-1-O-(6-O-(3,4-dichlorophenylthiocarbamoyl)-α-D-galactopyranosyl)-2-hexacosylamino-octadecane-1,3,4-triol,
(2S,3S,4R)-1-O-(6-O-(2,4-difluorophenylthiocarbamoyl)-α-D-galactopyranosyl)-2-hexacosylamino-octadecane-1,3,4-triol,
(2S,3S,4R)-1-O-(6-O-(2-trifluoromethoxyphenylthiocarbamoyl)-α-D-galactopyranosyl)-2-hexacosylamino-octadecane-1,3,4-triol,
(2S,3S,4R)-1-O-(6-O-(2,6-difluorophenylthiocarbamoyl)-α-D-galactopyranosyl)-2-hexacosylamino-octadecane-1,3,4-triol,
(2S,3S,4R)-1-O-(6-O-(2,5-difluorophenylthiocarbamoyl)-α-D-galactopyranosyl)-2-hexacosylamino-octadecane-1,3,4-triol,
(2S,3S,4R)-1-O-(6-O-(2-ethoxyphenylthiocarbamoyl)-α-D-galactopyranosyl)-2-hexacosylamino-octadecane-1,3,4-triol,
(2S,3S,4R)-1-O-(6-O-(4-ethoxyphenylthiocarbamoyl)-α-D-galactopyranosyl)-2-hexacosylamino-octadecane-1,3,4-triol,
(2S,3S,4R)-1-O-(6-O-(2-nitrophenylthiocarbamoyl)-α-D-galactopyranosyl)-2-hexacosylamino-octadecane-1,3,4-triol,
(2S,3S,4R)-1-O-(6-O-(4-nitrophenylthiocarbamoyl)-α-D-galactopyranosyl)-2-hexacosylamino-octadecane-1,3,4-triol,
(2S,3S,4R)-1-O-(6-O-(3-nitrophenylthiocarbamoyl)-α-D-galactopyranosyl)-2-hexacosylamino-octadecane-1,3,4-triol,
(2S,3S,4R)-1-O-(6-O-(4-tert-butylphenylthiocarbamoyl)-α-D-galactopyranosyl)-2-hexacosylamino-octadecane-1,3,4-triol,
(2S,3S,4R)-1-O-(6-O-(2-tert-butylphenylthiocarbamoyl)-α-D-galactopyranosyl)-2-hexacosylamino-octadecane-1,3,4-triol,
(2S,3S,4R)-1-O-(6-O-(4-isopropylphenylthiocarbamoyl)-α-D-galactopyranosyl)-2-hexacosylamino-octadecane-1,3,4-triol,
(2S,3S,4R)-1-O-(6-O-(2,6-diisopropylphenylthiocarbamoyl)-α-D-galactopyranosyl)-2-hexacosylamino-octadecane-1,3,4-triol,
(2S,3S,4R)-1-O-(6-O-(3-cyanophenylthiocarbamoyl)-α-D-galactopyranosyl)-2-hexacosylamino-octadecane-1,3,4-triol,
(2S,3S,4R)-1-O-(6-O-(2,4-dimethoxyphenylthiocarbamoyl)-α-D-galactopyranosyl)-2-hexacosylamino-octadecane-1,3,4-triol,
(2S,3S,4R)-1-O-(6-O-(2,6-dimethylphenylthiocarbamoyl)-α-D-galactopyranosyl)-2-hexacosylamino-octadecane-1,3,4-triol,
(2S,3S,4R)-1-O-(6-O-(4-dimethylaminophenylthiocarbamoyl)-α-D-galactopyranosyl)-2-hexacosylamino-octadecane-1,3,4-triol, and
(2S,3S,4R)-1-O-(6-O-(3-methylthiophenylthiocarbamoyl)-α-D-galactopyranosyl)-2-hexacosylamino-octadecane-1,3,4-triol.

EXAMPLE 5

Anti-microbial Screening Assay

The following illustrative, but non-limiting, methodology is carried out for testing the anti-microbial activity of the compounds of this invention. *Streptococcus pyogenes* (ATCC #97-03 14289) are grown in Todd Hewitt Broth (THB) (Difco Laboratories #0492-17-6) overnight until they reach an optical density (OD) of 0.636 at 570 nm by reading 0.1 ml in a 96 well microtiter plate in a Molecular Devices Thermomax. This preparation is kept frozen as stocks in 30% v/v glycerol in 1.5 ml aliquots at −70° C. until use. Prior to experiments, 1.5 ml aliquots are thawed and diluted into 50 ml THB. 200 µl of this dilution is added to 92 wells of microtiter plate. To three wells THB (200 µl) is added to serve as a blank and a sterility control. Test compounds in DMSO and appropriate concentrations of DMSO are added to Growth/Solvent Controls at 0 time. Plates are read at 0 time at 570 nm in the Molecular Devices plate reader to obtain compounds correction factors for insoluble or colored compounds. Plates are read again at 4 hours time. Percent inhibition is calculated with the following formulae:

$$a) \text{ Color correction} = (O.D.\ 0\ hr - \text{blank}\ 0\ hr) - (\text{Solvent Control}\ 0\ hr - \text{blank}\ 0\ hr);$$

$$b) \%\ \text{inhib.} = 100 - \frac{O.D.\ \text{test compound}\ 4\ hr - \text{blank}\ 4\ hr - \text{color correction}}{O.D.\ \text{growth/solvent control}\ 4\ hr - \text{blank}\ 4\ hr}$$

EXAMPLE 6

Use of a Galactopyranosyl Compound as an Immune Adjuvant

In order to assess the role of a GalCer derivative compound of this invention as an adjuvant for a T cell-mediated immune response, we used ovalbumin (OVA) as antigen since antigen presentation can be readily monitored using CD4+ and CD8+ OVA-specific TCR transgenic T cells. OVA was administered to mice intravenously either as a soluble protein (where 5 mg was required) or in association with dying osmotically shocked, syngeneic, TAP^(â"/â") splenocytes (where only 1 μg was associated with the injected cells; the dying cells efficiently target to dendritic cells in spleen, accounting for the high efficiency of presentation. Briefly, spleen cells were incubated with hypertonic medium at 37° C. in the presence or absence of 10 mg/ml OVA for 10 minutes, and further incubated with hypotonic medium for 2 minutes to induce apoptosis, followed by washing with cold PBS. After injection of OVA in either soluble or cell-associated forms, the following tests for antigen presentation were done. (a) CD11c$^+$DC-enriched and CD11c$^{â"}$ DC-depleted spleen cells were isolated 4 hours after OVA injection and used to stimulate proliferation of OT-I or OT-II T cells in culture. (b) 7 days after OVA injection, mice were tested for T cell priming by quantifying OVA-specific, IFN-γ and IL-4 producing T cells in the spleen. (c) Mice were given $10^6$ OT-I OVA-specific T cells intravenously and 1 day later the animals were primed with OVA and a GalCer derivative compound of this invention; 3 days later, the OVA-specific T cells were monitored for expansion in cell numbers and intracellular IFN-γ production. (d) CD11c$^+$ DC-enriched and CD11c$^{â"}$ DC-depleted spleen cells were isolated 4 hours after OVA injection and used at a dose of 1 and $10\times10^6$ respectively to prime naive recipients, assessed as in approach (b) above.

EXAMPLE 7

Synthesis of Further Aromatic, Heterocyclic and Non-aromatic Carbamate-containing Galactopyranosyl Compounds While using the general principles and the detailed synthetic methodologies outlined in example 1, and making reference to FIG. 12, a series of further aromatic, heterocyclic and non-aromatic carbamate-containing galacto-pyranosyl compounds has been prepared and characterized as follows.

To a solution of compound 1 (0.08 mmol) in DMF (2 mL) was added CDI (1.8 mmol) and potassium tert-butoxide (0.13 mmol) followed by heating until 50° C. After stirring for 3 hours the appropriate amine (3.68 mmol) was added. The reaction mixture was stirred overnight at 50° C. followed by evaporation to dryness under reduced pressure except for the synthesis of compound 2e. There the reaction mixture was first extracted with $H_2O$ and DCM, washed with $H_2O$, dried on $Na_2SO_4$ and filtrated before evaporating under reduced pressure. Purification by column chromatography (hexanes/EtOAc: 7/3) afforded the carbamate 2d (76% yield), purification by flash column chromatography ($CH_2Cl_2$/MeOH: 9/1) afforded the carbamate 2e (70% yield), purification by flash column chromatography (hexanes/EtOAc: 7.5/2.5) afforded the carbamate 2f (75% yield), and purification by flash column chromatography (hexanes/EtOAc: 5.5/4.5) afforded the carbamate 2h (75% yield).

(2S,3S,4R)-3,4-di-O-benzyl-1-O-(2,3,4-tri-O-benzyl-6-O-(morpholine-4-carboxyl)-α-D-galactopyranosyl)-2-hexacosanamido-octadecane-1,3,4-triol (2d) was Characterized as Follows:

$^1$H NMR (300 MHz, CDCl$_3$): δ 7.33-7.14 (m, 25H, arom. H), 5.84 (d, J=8.5 Hz, 1H, NH), 4.89 (d, J=11.4 Hz, 1H, CH$_2$—Ph), 4.83 (d, J=3.5 Hz, 1H, H-1"), 4.79-4.66 (m, 4H, CH$_2$—Ph), 4.59-4.53 (m, 2H, CH$_2$—Ph), 4.51 (d, J=11.4 Hz, 1H, CH$_2$—Ph), 4.43 (d, J=11.7 Hz, 1H, CH$_2$—Ph), 4.13-4.11 (m, 1H, H-2), 4.08-4.04 (m, 2H, H-6"), 3.99 (dd, J=3.5 and 10.0 Hz, 1H, H-2"), 3.86-3.81 (m, 2H, H-5", H-3"), 3.78-3.66 (m, 4H, H-1, H-4", H-3), 3.58-3.19 (m, 9H, H-4, CH$_2$), 1.93-1.80 (m, 2H, COCH$_2$), 1.60-1.16 (m, 72H, CH$_2$), 0.80 (t, J=6.7, 6H, CH$_3$);

$^{13}$C NMR (75 MHz, CDCl$_3$): δ 172.95, 155.08, 138.81, 138.75, 138.60, 138.44, 138.37, 128.66, 128.60, 128.58, 128.54, 128.11, 128.02, 128.00, 127.83, 127.66, 71.99, 36.93, 32.16, 29.96, 29.94, 29.59, 28.62, 22.92, 14.35; and Exact mass (ESI-MS) for $C_{90}H_{136}N_2O_{11}$ [M+H]$^+$ found, 1422.0332; calculated, 1422.0217.

(2S,3S,4R)-3,4-di-O-benzyl-1-O-(2,3,4-tri-O-benzyl-6-O-(2-(dimethylamino)ethylcarbamoyl)-α-D-galactopyranosyl)-2-hexacosanamido-octadecane-1,3,4-triol (2e) was Characterized as Follows:

$^1$H NMR (300 MHz, CDCl$_3$): δ 7.40-7.21 (m, 25H, arom. H), 5.95 (d, J=8.2 Hz, 1H, NH), 5.33 (m, 1H, NH), 4.95 (d, J=11.1 Hz, 1H, CH$_2$—Ph), 4.88 (d, J=3.5 Hz, 1H, H-1"), 4.84-4.74 (m, 4H, CH$_2$—Ph), 4.65-4.57 (m, 3H, CH$_2$—Ph), 4.51 (d, J=11.4 Hz, 1H, CH$_2$—Ph), 4.46 (d, J=11.7 Hz, 1H, CH$_2$—Ph), 4.21-4.18 (m, 1H, H-2), 4.07-3.99 (m, 1H, H-6"), 3.91-3.88 (m, 2H, H-2", H-6"), 3.91-3.88 (m, 4H, H-1, H-3", H-4", H-5"), 3.86-3.77 (m, 2H, H-1, H-3), 3.53-3.48 (m, 1H, H-4), 3.20-3.12 (m, 2H, CH$_2$) 2.32 (t, J=6.16 Hz 2H, CH$_2$), 2.18 (s, 6H, CH$_3$), 2.04-1.88 (m, 2H, COCH$_2$), 1.67-1.23 (m, 72H, CH$_2$), 0.90-0.86 (m, 6H, CH$_3$);

$^{13}$C NMR (75 MHz, CDCl$_3$): δ 138.85, 128.64, 128.58, 128.10, 128.03, 127.97, 127.79, 127.63, 36.95, 32.16, 29.96, 29.93, 29.61, 22.92, 14.35; and Exact mass (ESI-MS) for $C_{90}H_{139}N_3O_{10}$ [M+H]$^+$ found, 1423.0958; calculated, 1423.0533.

(2S,3S,4R)-3,4-di-O-benzyl-1-O-(2,3,4-tri-O-benzyl-6-O-(minolin-4-ylcarbamoyl)-α-D-galactopyranosyl)-2-hexacosanamido-octadecane-1,3,4-triol (2f) was Characterized as Follows:

$^1$H NMR (300 MHz, CDCl$_3$): δ 9.24 (s, 1H, NH), 8.76 (d, J=5.3 Hz, 1H, arom.H), 8.46 (d, J=8.5 Hz, 1H, arom.H), 8.10-8.06 (m, 2H, arom.H), 8.70-8.64 (m, 2H, arom.H), 7.39-7.44 (m, 1H, arom.H), 7.43-7.19 (m, 25H, arom. H), 5.81 (d, J=6.4 Hz, 1H, NH), 4.98 (d, J=11.7 Hz, 1H, CH$_2$—Ph), 4.93-4.85 (m, 2H, H-1", CH$_2$—Ph), 4.81-4.58 (m, 5H, CH$_2$—Ph), 4.56-4.42 (m, 4H, H-2, H-6", CH$_2$—Ph), 4.11-4.04 (m, 3H, H-1, H-2"), 3.96-3.90 (m, 1H, H-5"), 3.88-3.84 (m, 3H, H-3, H-3", H-4"), 3.77 (dd, J=1.3 and 11.6 Hz, 1 H, H-6"), 3.52-3.50 (m, 1 H, H-4), 3.75 (app. s, 1 H, H-4"), 3.68-3.64 (m, 1H, H-3), 3.62-3.56 (m, 1H, H-1), 3.48-3.43 (m, 1H, H-4), 2.10-1.96 (m, 2H, COCH$_2$), 1.62-0.96 (m, 72H, CH$_2$), 0.90-0.82 (m, 6H, CH$_3$);

$^{13}$C NMR (75 MHz, CDCl$_3$): δ 173.31, 173.18, 171.15, 153.40, 150.85, 148.65, 142.37, 138.56, 138.38, 138.200, 137.94, 129.70, 129.12, 128.47, 128.30, 127.97, 127.72, 127.58, 127.46, 125.73, 121.44, 120.27, 108.83, 100.73, 80.63, 79.22, 79.08, 75.11, 74.88, 74.55, 74.33, 73.72, 73.59, 73.48, 73,22, 73.10, 72.16, 71.87, 71.30, 70.14, 69.901, 66.52, 60.40, 52.33, 36.78, 31.94, 30.76, 30.12, 29.71, 29.39, 29.26, 27.91, 25.80, 25.68, 22.70, 21.06, 14.13; and Exact mass (ESI-MS) for $C_{95}H_{135}N_3O_{10}$ [M+H]$^+$ found, 1479.0785; calculated, 1479.0220.

(2S,3S,4R)-3,4-di-O-benzyl-1-O-(2,3,4-tri-O-benzyl-6-O-(1-benzylpiperidin-4-ylcarbamoyl)-α-D-galactopyranosyl)-2-hexacosanamido-octadecane-1,3,4-triol (2h) was Characterized as Follows:

$^1$H NMR (300 MHz, CDCl$_3$): δ 7.39-7.19 (m, 30H, arom. H), 5.85 (d, J=7.6 Hz, 1H, NH), 5.08 (d, J=7.6 Hz, 1H, NH), 4.94 (d, J=11.4 Hz, 1H, CH$_2$—Ph), 4.87 (d, J=3.8 Hz, 1H, H-1"), 4.85-4.70 (m, 4H, CH$_2$—Ph), 4.64-4.57 (m, 2H, CH$_2$—Ph), 4.60 (d, J=8.5 Hz, 1H, CH$_2$—Ph), 4.51 (d, J=8.8 Hz, 1H, CH$_2$—Ph), 4.51 (d, J=8.8 Hz, 1H, CH$_2$—Ph), 4.23-4.22 (m, 1H, H-2), 4.15 (dd, J=7.47 and 10.9 Hz, 1H, H-6"), 4.05 (dd, J=3.66 and 9.81 Hz, 1H, H-2"), 3.96-3.85 (m, 7H, H-1, H-3, H-3", H-4", H-5", H-6"), 3.55-3.47 (m, 1H, H-4), 3.46 (s, 2H, CH$_2$—Ph), 3.41-3.38 (m, 1H, CH), 2.76-2.74 (m, 2H, piperidin H), 2.03-1.98 (m, 2H, piperidin H), 1.95-1.87 (m, 2H, COCH$_2$), 1.85-1.77 (m, 4H, piperdin CH$_2$), 1.71-1.23 (m, 72H, CH$_2$), 0.90-0.85 (m, 6H, CH$_3$);

$^{13}$C NMR (75 MHz, CDCl$_3$): δ 172.92, 155.43, 138.60, 138.57, 138.55, 138.35, 138.16, 129.04, 128.43, 128.38, 128.37, 128.35, 128.19, 1278.93, 127.83, 127.79, 127.72, 127.67, 127.64, 127.60, 127.42, 126.99, 99.25, 79.83, 79.30, 79.12, 74.77, 74.50, 73.63, 73.52, 73.14, 71.82, 69.57, 68.59, 64.34, 63.00, 52.15, 50.79, 48.20, 36.76, 32.31, 31.95, 31.94, 30.13, 29.82, 29.75, 29.71, 29.67, 29.64, 29.48, 29.39, 29.37, 26.02, 25.69, 22.70, 14.13; and Exact mass (ESI-MS) for C$_{98}$H$_{145}$N$_3$O$_{10}$ [M+H]$^+$ found, 1525.0098; calculated, 1525.1003.

Procedure for Debenzylation (3d-q)

A solution of the protected carbamate (0.03 mmol) in CHCl$_3$ (0.4 mL) and EtOH (1.2 mL) was hydrogenated under atmospheric pressure in the presence of palladium black (10 mg). Upon reaction completion, the mixture was diluted with pyridine and filtered through celite. The filter cake was rinsed with CHCl$_3$ and EtOH and the filtrate was evaporated to dryness. After purification by column chromatography (CH$_2$Cl$_2$/MeOH), final compounds 3a-g were obtained in good yields.

(2S,3S,4R)-1-O-(6-O-(morpholine-4-carboxyl)-α-D-galactopyanosyl)-2-hexacosanamido-octadecane-1,3,4-triol (3d) was Characterized as Follows:

$^1$H NMR (300 MHz, pyridine-d$_5$): δ 8.54 (d, J=8.5 Hz, 1H, NH), 6.63 (s, 1H, OH), 6.38 (s, 1H, OH), 6.10 (s, 1H, OH), 5.55 (d, J=2.77, 1H, OH), 5.55 (d, J=3.1, 1H, H-1"), 5.27 (app. s, 1H, H-2), 4.91 (app. s, 1H, H-6"), 4.81 (dd, J=3.8 and 10.7 Hz, 1H, H-6"), 4.70-4.63 (m, 2H, H-1, H-2"), 4.50-4.56 (m, 1H, H-5"), 4.43-4.33 (m, 5H, H-1, H-3, H-4, H-3", H-4"), 3.59 (app.d, 8H, CH$_2$), 2.48 (t, J=7.0 Hz, 2H, COCH$_2$), 1.94-1.27 (m, 72H, CH$_2$), 0.89-0.87 (m, 6H, CH$_3$);

$^{13}$C NMR (75 MHz, pyridine-d$_5$): δ 172.00, 154.34, 99.91, 75.48, 71.40, 70.08, 69.55, 68.97, 68.58, 67.06, 65.50, 64.90, 50.00, 43.25, 35.61, 33.14, 30.94, 30.95, 29.21, 28.98, 28.63, 28.83, 28.76, 28.74, 28.70, 28.65, 28.60, 28.45, 28.43, 25.59, 25.32, 25.24, 21.76, 13.10; and Exact mass (ESI-MS) for C$_{55}$H$_{106}$N$_2$O$_{11}$ [M+H]$^+$ found, 971.7872; calculated, 971.7869.

(2S,3S,4R)-1-O-(6-O-(2-(dimethylamino)ethylcarbamoyl)-α-D-galactopyranosyl)-2-hexacosanamido -octadecane-1,3,4-triol (3e) was Characterized as Follows:

$^1$H NMR (300 MHz, pyridine-d$_5$): δ 8.65 (d, J=7.8 Hz, 1H, NH), 7.93 (app. s, 1 H, NH), 5.50 (app. s, 1 H, H-1"), 5.21 (app. s, 1H, H-2"), 4.94-4.87 (m, 1 H, H-6"), 4.79-4.75 (m, 1 H, H-6"), 4.68-4.59 (m, 1 H, H-1, H-2", H-5"), 4.41-4.32 (m, 5H, H-1, H-3, H-4, H-3", H-4"), 3.62-3.60 (m, 2H, CH$_2$), 2.89-2.80 (m, 2H, CH$_2$), 2.42 (s, 6H, CH$_3$), 2.29-2.14 (m, 2H, COCH$_2$), 2.00-1.27 (m, 72H, CH$_2$), 0.89-0.87 (m, 6H, CH$_3$); and Exact mass (ESI-MS) for C$_{55}$H$_{109}$N$_3$O$_{10}$ [M+H]$^+$ found, 972.8184; calculated, 972.8186.

(2S,3S,4R)-1-O-(6-O-(quinolin-4-ylcarbamoyl)-α-D-galactopyanosyl)-2-hexacosanamido-octadecane-1,3,4-triol (3f) was Characterized as Follows:

Exact mass (ESI-MS) for C$_{60}$H$_{105}$N$_3$O$_{10}$ [M+H]$^+$ found, 1028.7860; calculated, 1028.7873.

(2S,3S,4R)-1-O-(6-O-(piperidin-4-ylcarbamoyl)-α-D-galactopyranosyl)-2-hexacosanamido-octadecane-1,3,4-triol (3g) was Characterized as Follows:

Exact mass (ESI-MS) for C$_{56}$H$_{109}$N$_3$O$_{10}$ [M+H]$^+$ found, 984.8155; calculated, 984.8186.

EXAMPLE 8

Preparation of Related Aromatic, Heterocyclic and Non-aromatic Carbamate-containing Galactopyranosyl Compounds The following carbamate-containing galactopyranosyl compounds are obtained whilst using the above described synthetic procedure for making compounds 3a-h (examples 1 and 7), but making use of another appropriate aromatic, heterocyclic or non-aromatic isocyanate as described hereinabove:

(2S,3S,4R)-1-O-(6-O-(methylcarbamoyl)-α-D-galactopyranosyl)-2-hexa-cosylamino-octadecane-1,3,4-triol,
(2S,3S,4R)-1-O-(6-O-(ethylcarbamoyl)-α-D-galactopyranosyl)-2-hexa-cosylamino-octadecane-1,3,4-triol,
(2S,3S,4R)-1-O-(6-O-(propylcarbamoyl)-α-D-galactopyranosyl)-2-hexa-cosylamino-octadecane-1,3,4-triol,
(2S,3S,4R)-1-O-(6-O-(isopropylcarbamoyl)-α-D-galactopyranosyl)-2-hexa-cosylamino-octadecane-1,3,4-triol,
(2S,3S,4R)-1-O-(6-O-(butylcarbamoyl)-α-D-galactopyranosyl)-2-hexa-cosylamino-octadecane-1,3,4-triol,
(2S,3S,4R)-1-O-(6-O-(tert-butylcarbamoyl)-α-D-galactopyranosyl)-2-hexa-cosylamino-octadecane-1,3,4-triol,
(2S,3S,4R)-1-O-(6-O-(octylcarbamoyl)-α-D-galactopyranosyl)-2-hexa-cosylamino-octadecane-1,3,4-triol,
(2S,3S,4R)-1-O-(6-O-(benzylcarbamoyl)-α-D-galactopyranosyl)-2-hexa-cosylamino-octadecane-1,3,4-triol,
(2S,3S,4R)-1-O-(6-O-(phenethylcarbamoyl)-α-D-galactopyranosyl)-2-hexa-cosylamino-octadecane-1,3,4-triol,
(2S,3S,4R)-1-O-(6-O-(1-phenylethylcarbamoyl)-α-D-galactopyranosyl)-2-hexa-cosylamino-octadecane-1,3,4-triol,
(2S,3S,4R)-1-O-(6-O-(cyclopentylmethylcarbamoyl)-α-D-galactopyranosyl)-2-hexa-cosylamino-octadecane-1,3,4-triol,
(2S,3S,4R)-1-O-(6-O-(cyclohexylmethylcarbamoyl)-α-D-galactopyranosyl)-2-hexa-cosylamino-octadecane-1,3,4-triol,
(2S,3S,4R)-1-O-(6-O-((4-morpholynyl)ethylcarbamoyl)-α-D-galactopyranosyl)-2-hexa-cosylamino-octadecane-1,3,4-triol,
(2S,3S,4R)-1-O-(6-O-((4-morpholinyl)butylcarbamoyl)-α-D-galactopyranosyl)-2-hexa-cosylamino-octadecane-1,3,4-triol,
(2S,3S,4R)-1-O-(6-O-(cyclopentylcarbamoyl)-α-D-galactopyranosyl)-2-hexa-cosylamino-octadecane-1,3,4-triol, and
(2S,3S,4R)-1-O-(6-O-(cyclohexylcarbamoyl)-α-D-galactopyranosyl)-2-hexa-cosylamino-octadecane-1,3,4-triol.

EXAMPLE 9

Preparation of Related Non-aromatic Thiocarbamate-containing Galactopyranosyl Compounds The following thiocarbamate-containing galactopyranosyl compounds are obtained whilst using the above described synthetic procedure for making compounds 3a-h (examples 1 and 7), but making use of another appropriate non-aromatic thioisocyanate as described hereinabove:

(2S,3S,4R)-1-O-(6-O-(benzylthiocarbamoyl)-α-D-galactopyranosyl)-2-hexa-cosylamino-octadecane-1,3,4-triol, (2S,3S,4R)-1-O-(6-O-(phenethylthiocarbamoyl)-α-D-galactopyranosyl)-2-hexa-cosylamino-octadecane-1,3,4-triol, and (2S,3S,4R)-1-O-(6-O-(methylthiocarbamoyl)-α-D-galactopyranosyl)-2-hexa-cosylamino-octadecane-1,3,4-triol.

EXAMPLE 10

Synthesis of Triazolyl-containing Galactopyranosyl Compounds

The synthesis of the desired triazolyl-containing galactopyranosyl compounds was performed in accordance with the scheme of FIG. 14, starting from compound 7. Conversion of the primary hydroxyl group to an azido group via a Mitsunobu reaction with diphenylphosphorazidate (DPPA) afforded compound 38 in excellent yield. We then performed the CuAAC reaction under microwave conditions (70-120° C., 250 W) in the presence of the appropriate alkyne, successfully obtaining compounds 39-43 in good yields. Due to solubility reasons, DMF was chosen as a solvent. More specifically, to a solution of azide 38 (80 mg, 0.06 mmol) in DMF (2 mL) was added the appropriate alkyne, sodium ascorbate and copper(II)sulfate. The reaction mixture was stirred for 20 minutes at 70° C. in the microwave. After extraction with EtOAc, the organic phase was washed with brine and dried over $Na_2SO_4$, followed by evaporation of the solvent and purification by column chromatography (hexanes/EtOAc: 7.5/2.5), affording the benzyloxy-protected compounds 39 (74%), 40 (60%), 41 (95%), 42 (80%) and 43 (97%) in good yields. The non-substituted triazolyl compound (R=H) was obtained by treatment with vinyl acetate (120° C.), thus provides an improved and simple method compared to the use of acetylene gas. Final debenzylation by a catalytic hydrogenolysis afforded the desired final compoundss 44-48 and the corresponding non-substituted triazolyl compound 49 (not represented in FIG. 14).

(2S,3S,4R)-3,4-di-O-benzyl-1-O-(2,3,4-tri-O-benzyl-6-deoxy-6-(4-butyltriazol-1-yl)-α-D-galactopyranosyl)-2-hexacosylamino-octadecane-1,3,4-triol (39) was Characterized as Follows:

$^1$H NMR (300 MHz, $CDCl_3$): 67.27-7.03 (m, 26H, arom. H), 5.63 (d, J=8.5 Hz, 1H, NH), 4.94 (d, J=11.1 Hz, 1H, $CH_2$—Ph), 4.78 (d, J=3.5 Hz, 1H, H-1"), 4.73 (d, J=11.7 Hz, 1H, $CH_2$—Ph), 4.71 (d, J=11.7 Hz, 1H, $CH_2$—Ph), 4.64 (d, J=11.7 Hz, 2H, $CH_2$—Ph), 4.57 (d, J=11.7 Hz, 1H, $CH_2$—Ph), 4.56 (d, J=11.1 Hz, 1H, $CH_2$—Ph), 4.48 (d, J=11.7 Hz, 1H, $CH_2$—Ph), 4.40 (d, J=11.7 Hz, 1H, $CH_2$—Ph), 4.39 (d, J=11.7 Hz, 1H, $CH_2$—Ph), 4.31 (dd, J=5.9 and 13.7 Hz, 1H, H-6"), 4.21-4.15 (m, 1H, H-2), 4.12 (dd, J=5.9 and 13.1 Hz, 1H, H-6"), 4.00-3.96 (m, 2H, H-2", H-5"), 3.80 (dd, J=2.6 and 10.2 Hz, 1 H, H-3"), 3.68-3.59 (m, 3H, H-4", H-3, H-1), 3.52-3.41 (m, 2H, H-1, H-4), 2.57 (app. t, J=7.7 Hz, 2H, $CH_2$), 1.88-1.71 (m, 2H, $COCH_2$), 1.56-1.05 (m, 72H, $CH_2$), 0.84 (t, J=7.3 Hz, 3H, $CH_3$), 0.81 (t, J=6.8 Hz, 6H, $CH_3$);

$^{13}$C NMR (75 MHz, $CDCl_3$): δ173.01, 148.40, 138.82, 138.77, 138.56, 138.49, 138.44, 128.76, 128.68, 128.65, 128.62, 128.57, 128.16, 128.11, 128.09, 127.99, 127.92, 127.81, 127.66, 122.29, 99.41, 79.87, 79.78, 79.25, 77.67, 77.45, 77.25, 76.82, 76.47, 74.95, 74.76, 73.81, 73.51, 73.41, 72.08, 70.17, 50.28, 36.87, 32.16, 31.75, 30.08, 29.96, 29.94, 29.91, 29.89, 29.85, 29.70, 29.61, 29.59, 26.06, 25.88, 25.52, 22.92, 22.55, 14.35, 14.05; and Exact mass (ESI-MS) for $C_{91}H_{138}N_4O_8$ $[M+H]^+$ found, 1416.0526; calculated, 1416.0593.

(2S,3S,4R)-3,4-di-O-benzyl-1-O-(2,3,4-tri-O-benzyl-6-deoxy-6-(4-phenyltriazol-1-yl)-α-D-galactopyranosyl)-2-hexacosylamino-octadecane-1,3,4-triol (40) was Characterized as Follows:

$^1$H NMR (300 MHz, $CDCl_3$): δ7.93-7.72 (m, 3H, arom. H), 7.31-7.18 (m, 28H), 5.55 (d, J=8.2 Hz, 1H, NH), 4.95 (d, J=10.9 Hz, 1H, $CH_2$—Ph), 4.78 (app. s, 1H, H-1"), 4.73-4.55 (m, 6H, $CH_2$—Ph), 4.47-4.34 (m, 4H, $CH_2$—Ph, H-6"), 4.25-4.18 (m, 2H, H-2, H-6"), 4.06-3.97 (m, 2H, H-5", H-2"), 3.79 (app. d, J=10.0 Hz, 1H, H-3"), 3.69-3.52 (m, 4H, H-4", H-3, H-1), 3.42-3.41 (m, 1H, H-4), 1.82-1.66 (m, 2H, $COCH_2$), 1.49-0.99 (m, 72H, $CH_2$), 0.80 (t, J=6.5 Hz, 6H, $CH_3$);

$^{13}$C NMR (75 MHz, $CDCl_3$): δ173.19, 162.87, 138.76, 138.68, 138.58, 138.51, 138.48, 130.85, 129.03, 128.82, 128.69, 128.68, 128.63, 128.58, 128.28, 128.21, 128.13, 128.01, 127.98, 127.91, 127.81, 127.68, 125.88, 121.47, 99.69, 80.15, 79.45, 79.27, 77.70, 77.49, 77.28, 76.86, 76.45, 75.06, 74.75, 73.80, 73.60, 73.40, 72.00, 70.10, 68.90, 50.41, 36.86, 36.73, 32.17, 31.69, 30.50, 30.08, 29.95, 29.90, 29.84, 29.65, 29.60, 25.86, 22.93, 14.37; and Exact mass (ESI-MS) for $C_{93}H_{134}N_4O_8$ $[M+H]^+$ found, 1436.0295; calculated, 1436.0274, $[M+Na]^+$ found 1458.0104; calculated, 1458.0094, $[M+K]^+$ found 1473.9843, calculated, 1473.9833.

(2S,3S,4R)-3,4-di-O-benzyl-1-O-(2,3,4-tri-O-benzyl-6-deoxy-6-(4-benzyltriazol-1-yl)-α-D-galactopyranosyl)-2-hexacosylamino-octadecane-1,3,4-triol (41) was Characterized as Follows:

$^1$H NMR (300 MHz, $CDCl_3$): δ7.30-7.09 (m, 31H, arom. H), 5.63 (d, J=8.6 Hz, 1H, NH), 4.92 (d, J=11.1 Hz, 1H, $CH_2$—Ph), 4.74 (d, J=2.9 Hz, 1H, H-1"), 4.70 (d, J=11.8 Hz, 1H, $CH_2$—Ph), 4.69 (d, J=13.0 Hz, 1H, $CH_2$—Ph), 4.66 (d, J=12.1 Hz, 1H, $CH_2$—Ph), 4.64 (d, J=11.6 Hz, 1H, $CH_2$—Ph), 4.56 (d, J=11.8 Hz, 1H, $CH_2$—Ph), 4.50 (d, J=11.1 Hz, 1H, $CH_2$—Ph), 4.48 (d, J=11.8 Hz, 1H, $CH_2$—Ph), 4.39 (d, J=11.8 Hz, 1H, $CH_2$—Ph), 4.38 (d, J=11.6 Hz, 1H, $CH_2$—Ph), 4.25 (dd, J=5.6 and 13.8 Hz, 1H, H-6"), 4.16-4.09 (m, 2H, H-2, H-6"), 3.98-3.93 (m, 4H, $CH_2$—Ph, H-2", H-5"), 3.79 (dd, J=2.4 and 10.1 Hz, 1H, H-3"), 3.68 (app. s, 1H, H-4"), 3.64 (dd, J=3.5 and 5.7 Hz, 1H, H-3), 3.55 (dd, J=6.1 and 10.7 Hz, 1H, H-1), 3.45-3.38 (m, 2H, H-4, H-1), 1.89-1.70 (m, 2H, $COCH_2$), 1.54-1.18 (m, 72H, $CH_2$), 0.80 (t, J=6.7 Hz, 6H, $CH_3$);

$^{13}$C NMR (75 MHz, $CDCl_3$): δ172.98, 147.54, 139.32, 138.82, 138.53, 138.46, 138.34, 128.85, 128.83, 128.71, 128.69, 128.64, 128.62, 128.58, 128.17, 128.11, 128.06, 128.04, 128.00, 127.95, 127.88, 127.81, 127.68, 126.97, 123.19, 99.27, 79.97, 79.58, 79.21, 77.67, 77.45, 77.25, 76.83, 76.42, 74.90, 74.71, 73.82, 73.49, 73.39, 72.04, 70.06, 68.41, 50.52, 50.17, 36.89, 32.38, 32.16, 30.34, 30.10, 29.97, 29.94, 29.89, 29.86, 29.71, 29.61, 29.60, 26.11, 25.90, 22.93, 14.36; and Exact mass (ESI-MS) for $C_{94}H_{136}N_4O_8$ $[M+H]^+$ found, 1450.0453; calculated, 1450.0431, $[M+Na]^+$ found 1472.0304; calculated, 1472.0250.

(2S,3S,4R)-3,4-di-O-benzyl-1-O-(2,3,4-tri-O-benzyl-6-deoxy-6-(4-ethylphenyltriazol-1-yl)-α-D-galactopyranosyl)-2-hexacosylamino-octadecane-1,3,4-triol (42) was Characterized as Follows:

$^1$H NMR (300 MHz, $CDCl_3$): δ7.30-7.06 (m, 31H, arom. H), 5.64 (d, J=8.5 Hz, 1H, NH), 4.93 (d, J=11.3 Hz, 1H, $CH_2$—Ph), 4.77 (d, J=3.7 Hz, 1H, H-1"), 4.73-4.62 (m, 3H, $CH_2$—Ph), 4.57 (d, J=11.7 Hz, 1H, $CH_2$—Ph), 4.52 (d, J=9.2 Hz, 1H, $CH_2$—Ph), 4.48 (d, J=9.6 Hz, 1H, $CH_2$—Ph), 4.40 (d, J=11.5 Hz, 1H, $CH_2$—Ph), 4.39 (d, J=11.5 Hz, 1H, $CH_2$—

Ph), 4.29 (dd, J=5.92 and 13.7 Hz, 1H, H-6"), 4.22-4.15 (1H, H-2), 4.14 (dd, J=6.7 and 13.9 Hz, 1H, H-6"), 4.01-3.95 (m, 2H, H-2", H-5"), 3.79 (dd, J=2.6 and 10.2 Hz, 1H, H-3"), 3.65-3.57 (m, 3H, H-4", H-3, H-1), 3.51-3.41 (m, 2H, H-1, H-4), 2.96-2.82 (m, 4H, $CH_2$—$CH_2$—Ph), 1.88-1.70 (m, 2H, $COCH_2$), 1.53-1.04 (m, 72H, $CH_2$), 0.81 (t, J=6.7 Hz, 6H, $CH_3$), $^{13}C$ NMR (75 MHz, $CDCl_3$): δ173.04, 147.29, 141.38, 138.80, 138.76, 138.56, 138.48, 138.41, 128.76, 128.69, 128.66, 128.61, 128.58, 128.17, 128.11, 128.09, 128.01, 127.93, 127.82, 127.65, 126.31, 122.61, 99.37, 79.84, 79.25, 77.67, 77.45, 77.25, 76.83, 76.48, 74.93, 74.71, 73.82, 73.54, 73.42, 72.08, 70.09, 68.50, 50.36, 50.28, 36.88, 35.71, 32.16, 30.45, 30.08, 29.96, 29.89, 29.86, 29.70, 29.61, 29.59, 27.61, 26.05, 25.89, 22.93, 21.28, 14.43, 14.36; and Exact mass (ESI-MS) for $C_{95}H_{138}N_4O_8$ [M+H]$^+$ found, 1464.0540; calculated, 1464.0593.

(2S,3S,4R)-3,4-di-O-benzyl-1-O-(2,3,4-tri-O-benzyl-6-deoxy-6-(4-propylphenyltriazol-1-yl)-α-D-galactopyranosyl)-2-hexacosylamino-octadecane-1,3,4-triol (43) was Characterized as Follows:

$^1H$ NMR (300 MHz, $CDCl_3$): δ7.36-7.17 (m, 31H, arom. H), 5.73 (d, J=8.5 Hz, 1H, NH), 5.03 (d, J=11.9 Hz, 1H, $CH_2$—Ph), 4.87 (d, J=3.5 Hz, 1H, H-1"), 4.82 (d, J=11.8 Hz, 1H, $CH_2$—Ph), 4.80 (d, J=11.8 Hz, 1H, $CH_2$—Ph), 4.73 (d, J=12.0 Hz, 2H, $CH_2$—Ph), 4.66 (d, J=11.8 Hz, 1H, $CH_2$—Ph), 4.65 (d, J=11.27 Hz, 1H, $CH_2$—Ph), 4.57 (d, J=11.6 Hz, 1H, $CH_2$—Ph), 4.49 (d, J=11.8 Hz, 1H, $CH_2$—Ph), 4.47 (d, J=11.6 Hz, 1H, $CH_2$—Ph), 4.40 (dd, J=6.0 and 13.8 Hz, 1 H, H-6"), 4.32-4.20 (m, 2H, H-2, H-6"), 4.11-4.05 (m, 2H, H-5", H-2"), 3.89 (dd, J=2.6 and 10.0 Hz, 1H, H-3"), 3.76 (app. d, J=1.5 Hz, 1H, H-4"), 3.74-3.66 (m, 2H, H-3, H-1), 3.59 (dd, J=4.6 and 10.7 Hz, 1H, H-1), 3.54-3.50 (m, 1H, H-4), 2.77-2.64 (m, 4H, $CH_2$-$CH_2$—Ph), 2.05-1.81 (m, 4H, $CH_2$, $CH_2$, $COCH_2$), 1.61-1.28 (m, 72H, $CH_2$), 0.90 (t, J=6.7 Hz, 6H, $CH_3$);

$^{13}C$ NMR (75 MHz, $CDCl_3$): δ173.04, 147.93, 142.09, 138.84, 138.79, 138.57, 138.51, 138.44, 128.79, 128.76, 128.72, 128.70, 128.66, 128.64, 128.61, 128.58, 128.18, 128.13, 128.10, 128.02, 127.94, 127.83, 127.68, 126.17, 126.07, 122.41, 99.43, 79.80, 79.26, 77.73, 77.30, 76.88, 76.50, 74.96, 74.75, 73.84, 73.54, 73.44, 72.08, 70.15, 68.94, 50.31, 36.88, 35.65, 34.87, 32.18, 31.29, 30.42, 30.30, 30.09, 29.98, 29.96, 29.94, 29.91, 29.87, 29.72, 29.63, 26.06, 25.91, 25.39, 22.95, 18.06, 14.38; and Exact mass (ESI-MS) for $C_{96}H_{140}N_4O_8$ [M+H]$^+$ found, 1478.0772; calculated, 1478,0749.

(2S,3S,4R)-3,4-di-O-benzyl-1-O-(2,3,4-tri-O-benzyl-6-deoxy-6-(triazol-1-yl)-α-D-galactopyranosyl)-2-hexacosylamino-octadecane-1,3,4-triol Here the azide 38 was dissolved in vinyl acetate and stirred at 120° C. in the microwave. After 6 hours, the reaction mixture was evaporated to dryness. Purification by column chromatography (hexanes/EtOAc: 7.5/2.5) afforded the desired non-substituted triazolyl compound (93 mg, yield 71%) which was characterized as follows:

$^1H$ NMR (300 MHz, $CDCl_3$): δ 7.53 (dd, J=0.9 and 7.3 Hz, 2H, arom. H), 7.36-7.22 (m, 25H, arom. H), 5.68 (d, J=8.5 Hz, 1 H, NH), 5.01 (d, J=11.2 Hz, 1 H, $CH_2$—Ph), 4.84 (d, J=3.6 Hz, 1 H, H-1"), 4.80 (d, J=11.8 Hz, 1H, $CH_2$—Ph), 4.78 (d, J=11.8 Hz, 1H, $CH_2$—Ph), 4.71 (d, J=11.7 Hz, 1H, $CH_2$—Ph), 4.70 (d, J=11.7 Hz, 1H, $CH_2$—Ph), 4.64 (d, J=11.7 Hz, 1H, $CH_2$—Ph), 4.63 (d, J=11.2 Hz, 1H, $CH_2$—Ph), 4.55 (d, J=11.6 Hz, 1H, $CH_2$—Ph), 4.47 (d, J=11.8 Hz, 1H, $CH_2$—Ph), 4.45 (d, J=11.8 Hz, 1H, $CH_2$—Ph), 4.39 (dd, J=5.2 and 13.9 Hz, 1H, H-6"), 4.29 (d, J=7.7 and 13.9 Hz, 1H, H-6"), 4.23-4.17 (m, 1H, H-2), 4.07-4.01 (m, 2H, H-2", H-5"), 3.87 (dd, J=2.6 and 10.1 Hz, 1H, H-3"), 3.77 (app. d, J=1.3 Hz, 1H, H-4"), 3.68 (dd, J=3.6 and 5.2 Hz, 1H, H-3), 3.62 (dd, J=6.9 and 10.6 Hz, 1H, H-1), 3.55-3.47 (m, 2H, H-1, H-4), 1.95-1.77 (m, 2H, $COCH_2$), 1.61-1.13 (m, 72H, $CH_2$), 0.88 (t, J=6.7 Hz, 6H, $CH_3$);

$^{13}C$ NMR (75 MHz, $CDCl_3$): δ172.95, 149.61, 138.59, 138.49, 138.33, 138.27, 138.08, 133.65, 128.57, 128.51, 128.48, 128.45, 128.41, 128.37, 128.03, 127.89, 127.88, 127.85, 127.79, 127.73, 127.62, 127.47, 124.77, 116.19, 99.01, 79.69, 79.61, 78.96, 76.25, 74.73, 74.63, 73.58, 73.38, 73.11, 71.96, 69.94, 50.40, 50.04, 36.69, 31.94, 30.28, 29.83, 29.74, 29.69, 29.67, 29.62, 29.46, 29.39, 29.37, 25.86, 25.67, 22.70, 14.13; and Exact mass (ESI-MS) for $C_{87}H_{130}N_4O_8$ [M+H]$^+$ found, 1359.9907; calculated, 1359.9967, [M+Na]$^+$found, 1381.9797; calculated, 1381.9786.

General Procedure for Debenzylation

A solution of the protected triazolyl-containing galactopyranosyl compound (0.06 mmol) in $CHCl_3$ (0.4 mL) and EtOH (1.2 mL) was hydrogenated under atmospheric pressure in the presence of palladium black (10 mg). Upon reaction completion, the mixture was diluted with pyridine and filtered through Celite. The filter cake was rinsed with $CHCl_3$ and EtOH and the filtrate was evaporated to dryness. After purification by column chromatography ($CH_2Cl_2$/MeOH: 8/2), final non-substituted (31%) and substituted compounds 44 (50%), 45 (40%), 46 (22%), 47 (31%) and 48 (53%) were obtained as white powders.

(2S,3S,4R)-1-O-(6-deoxy-6-(triazol-1-yl)-α-D-galactopyranosyl)-2-hexacosylamino-octadecane-1,3,4-triol was Characterized as Follows:

$^1H$ NMR (300 MHz, pyridine-$d_5$): δ8.42 (d, J=8.9 Hz, 1H, NH), 8.21 (d, J=0.9 Hz, 1H,arom. H), 7.92 (d, J=0.9 Hz, 1H, arom. H), 5.5 (d, J=3.7 Hz, 1H, H-1"), 5.26-5.19 (m, 1H, H-2), 5.14-4.99 (m, 2H, H-6"), 4.67-4.61 (m, 2H, H-2", H-5"), 4.38-4.30 (3H, H-1, H-3", H-3), 4.26-4.21 (m, 2H, H-4, H-4"), 4.09 (dd, J=4.9 Hz and 10.6 Hz, 1H, H-1), 2.50-2.36 (m, 2H, $COCH_2$), 2.01-1.09 (m, 72H, $CH_2$), 0.88 (t, J=6.7 Hz, 6H, $CH_3$);

$^{13}C$ NMR (75 MHz, pyridine-$d_5$): δ 171.92, 149.07, 148.72, 148.36, 147.99, 135.00, 134.66, 134.33, 134.00, 133.64, 132.60, 124.24, 122.98, 122.65, 122.32, 121.99, 121.61, 99.98, 75.54, 71.23, 69.78, 69.67, 69.47, 68.57, 67.06, 50.30, 49.77, 35.57, 33.34, 30.94, 29.21, 28.97, 28.86, 28.83, 28.75, 28.69, 28.63, 28.58, 28.43, 25.27, 25.20, 21.76, 13.10;

IR: 3462, 3451, 3335, 2922, 2850, 1653 cm$^{-1}$.; and

Exact mass (ESI-MS) for $C_{52}H_{100}N_4O_8$[M+H]$^+$ found, 909.7681; calculated, 909.7619, [M+Na]+ found, 931.7450; calculated, 931.7439.

(2S,3S,4R)-1-O-(6-deoxy-6-(4-butyltriazol-1-yl)-α-D-galactopyranosyl)-2-hexacosylamino-octadecane-1,3,4-triol (44) was Characterized as Follows:

$^1H$ NMR (300 MHz, pyridine-$d_5$): δ 8.42 (d, J=8.7 Hz, 1H, NH), 7.93 (s, 1H, arom. H), 6.83 (br. s, 1H, OH), 6.37 (br. s, 1H, OH), 6.05 (br. s, 1H, OH), 5.52 (d, J=3.9 Hz, 1H, H-1"), 5.26-5.19 (m, 1H, H-2), 5.03 (app. d, J=6.5 Hz, 2H, H-6"), 4.70-4.62 (m, 2H, H-5", H-2"), 4.41 (dd, J=5.4 and 10.7 Hz, 1H, H-1), 4.32 (dd, J=3.2 and 9.9 Hz, 1H, H-3"), 4.27-4.22 (m, 3H, H-3, H-4", H-4), 4.16 (dd, J=4.9 and 10.6 Hz, 1H, H-1), 2.83 (t, J=7.6 Hz, 2H, $CH_2$), 2.48-2.39 (m, 2H, $COCH_2$), 1.94-1.11 (m, 76H, $CH_2$), 0.93-0.86 (m, 9H, $CH_3$);

$^{13}C$ NMR (75 MHz, pyridine-$d_5$): δ 171.94, 100.11, 75.56, 71.24, 69.83, 69.72, 69.41, 68.62, 67.25, 50.21, 49.90, 35.58, 33.32, 30.94, 30.81, 29.24, 28.98, 28.86, 28.83, 28.75, 28.74, 28.71, 28.64, 28.61, 28.44, 28.43, 25.29, 25.21, 24.59, 21.76, 21.39, 13.10, 12.82; and Exact mass (ESI-MS) for $C_{56}H_{108}N_4O_8$ [M+H]$^+$ found, 965.8295; calculated, 965.8240, [M+Na]$^+$ found, 987.8087; calculated, 987.8059, [M+K]$^+$ found, 1003.7825; calculated, 1003.7799.

(2S,3S,4R)-1-O-(6-deoxy-6-(4-phenyltriazol-1-yl)-α-D-galactopyranosyl)-2-hexacosylamino-octadecane-1,3,4-triol (45) was Characterized as Follows:

$^1$H NMR (300 MHz, pyridine-d$_5$): δ8.66 (s, 1H, arom. H), 8.40 (d, J=8.7 Hz, 1H, NH), 8.21-8.18 (m, 2H, arom. H), 7.50-7.45 (m, 2H, arom. H), 7.38-7.33 (m, 1H, arom. H), 5.55 (d, J=3.7 Hz, 1H, H-1"), 5.28-5.19 (m, 1H, H-2), 5.10 (app. d, J=5.5 Hz, 2H, H-6"), 4.75 (t, J=6.6 Hz, 1H, H-5"), 4.66 (dd, J=3.7 and 9.8 Hz, 1H, H-2"), 4.45 (dd, J=5.6 and 10.6 Hz, 1H, H-1), 4.35 (dd, J=3.2 and 9.9 Hz, 1H, H-3"), 4.27-4.22 (m, 3H, H-3, H-4, H-4"), 4.15 (dd, J=4.9 and 10.8 Hz, 1H, H-1), 2.45-2.22 (m, 2H, COCH$_2$), 1.90-1.17 (m, 72H, CH$_2$), 0.88 (t, J=6.7 Hz, 6H, CH$_3$);

$^{13}$C NMR (75 MHz, pyridine-d$_5$): δ 171.95, 149.40, 149.07, 148.71, 148.35, 146.54, 134.66, 134.33, 134.00, 130.91, 128.07, 126.94, 124.95, 122.99, 122.66, 122.33, 122.00, 121.60, 121.01, 100.05, 75.56, 71.22, 69.79, 69.54, 69.25, 68.60, 67.07, 50.34, 49.83, 35.54, 33.32, 30.94, 29.23, 28.97, 28.87, 28.83, 28.75, 28.74, 28.70, 28.61, 28.58, 28.44, 28.43, 25.26, 25.18, 21.76, 13.10; and Exact mass (ESI-MS) for $C_{58}H_{104}N_4O_8$ [M+H]$^+$ found, 985.7953; calculated, 985.7927, [M+Na]$^+$ found, 1007.7729; calculated, 1007.7746.

(2S,3S,4R)-1-O-(6-deoxy-6-(4-benzyltriazol-1-yl)-α-D-galactopyranosyl)-2-hexacosylamino-octadecane-1,3,4-triol (46) was Characterized as Follows:

$^1$H NMR (300 MHz, pyridine-d$_5$): δ 8.41 (d, J=8.7 Hz, 1H, NH), 7.91 (s, 1H, arom. H), 7.47-7.45 (m, 2H, arom. H), 7.41-7.36 (m, 2H, arom. H), 7.28-7.26 (m, 1H, arom. H), 5.48 (d, J=3.7 Hz, 1H, H-1"), 5.23-5.19 (m, 1H, H-2), 5.01-4.99 (m, 2H, H-6"), 4.64-4.59 (m, 2H, H-2", H-5"), 4.36 (dd, J=5.2 and 10.7 Hz, 1 H, H-1), 4.32-4.25 (m, 3H, H-4, H-4", H-3, CH$_2$—Ph), 4.21 (app. d, J=2.4 Hz, 1H, H-3"), 4.14 (dd, J=4.6 and 10.7 Hz, 1H, H-1), 2.48-2.41 (m, 2H, COCH$_2$), 1.93-1.26 (m, 72H, CH$_2$), 0.88 (t, J=6.6 Hz, 6H, CH$_3$);

$^{13}$C NMR (75 MHz, pyridine-d$_5$): δ 171.92, 149.06, 148.70, 148.35, 147.98, 146.06, 139.26, 135.00, 134.66, 134.33, 133.99, 133.64, 128.02, 127.78, 125.45, 122.98, 122.65, 122.32, 122.20, 121.99, 100.13, 75.55, 71.30, 69.79, 69.71, 69.47, 68.56, 67.44, 50.37, 49.83, 35.58, 33.29, 31.33, 30.95, 29.24, 28.98, 28.87, 28.83, 28.75, 28.74, 28.71, 28.64, 28.61, 28.58, 28.44, 28.43, 28.37, 25.31, 25.22, 21.76, 13.10; and Exact mass (ESI-MS) for $C_{59}H_{106}N_4O_8$ [M+H]$^+$ found, 999.8134; calculated, 999.8089, [M+Na]$^+$ found, 1021.7906; calculated, 1021.7908, [M+K]$^+$ found, 1037.7676; calculated, 1037.7648.

(2S,3S,4R)-1-O-(6-deoxy-6-(4-ethylphenyltriazol-1-yl)-α-D-galactopyranosyl)-2-hexacosylamino-octadecane-1,3,4-triol (47) was Characterized as Follows:

$^1$H NMR (300 MHz, pyridine-d$_5$): δ8.43 (d, J=8.7 Hz, 1H, NH), 7.88 (s, 1H, arom. H), 7.36-7.31 (m, 3H, arom. H), 7.27-7.25 (m, 2H, arom. H), 5.50 (d, J=3.9 Hz, 1H, H-1"), 5.26-5.19 (m, 1H, H-2), 5.01-4.96 (m, 2H, H-2", H-5"), 4.67-4.61 (m, 2H, H-6"), 4.39 (dd, J=5.3 and 10.6 Hz, 1H, H-1), 4.61 (dd, J=3.2 and 9.9 Hz, 1H, H-3" or H-4") 4.56 (m, 2H, H-3, H-4), 4.49 (app. d, J=2.4 Hz, H-3" or H-4"), 4.15 (dd, J=5.0 and 10.7 Hz, 1H, H-1), 3.22-3.11 (m, 4H, CH$_2$), 2.47-2.40 (m, 2H, COCH$_2$), 1.94-1.24 (m, 72H, CH$_2$), 0.89 (t, J=6.7 Hz, 6H, CH$_3$);

$^{13}$C NMR (75 MHz, pyridine-d$_5$): δ 173.49, 150.58, 150.21, 149.86, 147.64, 142.41, 136.17, 135.84, 135.51, 129.24, 129.12, 126.72, 124.49, 124.16, 123.83, 123.50, 123.18, 123.12, 101.57, 77.11, 72.76, 71.34, 71.22, 70.91, 70.14, 51.76, 51.42, 37.10, 36.35, 34.85, 32.46, 32.45, 30.75, 30.49, 30.38, 30.34, 30.27, 30.25, 30.21, 30.14, 30.11, 29.96, 29.94, 28.44, 26.80, 26.72, 23.27, 14.61; and Exact mass (ESI-MS) for $C_{60}H_{108}N_4O_8$ [M+H]$^+$ found, 1013.8259; calculated, 1013.8240.

(2S,3S,4R)-1-O-(6-deoxy-6-(4-propylphenyltriazol-1-yl)-α-D-galactopyranosyl)-2-hexacosylamino-octadecane-1,3,4-triol (48) was Characterized as Follows:

$^1$H NMR (300 MHz, pyridine-d$_5$): δ 8.38 (d, J=8.7 Hz, 1H, NH), 7.93 (s, 1H, arom. H), 7.37-7.24 (m, 5H, arom. H), 7.11 (br. s, 1H, OH), 6.94 (br. s, 1H, OH), 6.82 (d, J=2.9 Hz, 1H, OH), 6.36 (d, J=5.0 Hz, 1H, OH), 6.04 (d, J=3.9 Hz, 1H, OH), 5.51 (d, J=3.7 Hz, 1H, H-1"), 5.26-5.18 (m, 1H, H-2"), 5.03 (d, J=5.03 Hz, 2H, H-6"), 4.71-4.62 (m, H-5", H-2"), 4.41 (dd, J=5.4 and 10.4 Hz, 1H, H-1), 4.33-4.20 (m, 5H, H-3", H-3, H-4, H-4"), 4.15 (dd, J=5.0 and 10.7 Hz, 1H, H-1), 2.86 (t, J=7.6 Hz, 2H, CH$_2$), 2.72 (t, J=7.6 Hz, 2H, CH$_2$), 2.41 (ddd, J=3.0 and 7.5 Hz, 2H, COCH$_2$), 2.10 (quintet, J=7.6 Hz, 2H, CH$_2$), 1.90-1.18 (m, 72H, CH$_2$), 0.87 (t, J=6.6 Hz, 6H, CH$_3$);

$^{13}$C NMR (75 MHz, pyridine-d$_5$): δ 173.43, 150.58, 150.22, 149.87, 149.49, 148.06, 142.91, 136.51, 136.17, 135.84, 135.51, 135.14, 129.33, 129.10, 126.51, 124.49, 124.16, 123.83, 123.50, 123.10, 101.63, 77.07, 72.75, 71.34, 71.21, 70.88, 70.13, 68.79, 51.70, 51.40, 37.08, 35.92, 34.83, 32.46, 32.45, 31.95, 30.75, 30.50, 30.38, 30.34, 30.27, 30.25, 30.22, 30.15, 30.12, 29.96, 29.94, 26.79, 26.72, 25.92, 23.28, 14.62; and Exact mass (ESI-MS) for $C_{61}H_{110}N_4O_8$ [M+H]$^+$ found, 1027.8478; calculated, 1027.8402.

EXAMPLE 11

Biological Evaluation of Triazolyl-containing Galactopyranosyl Compounds

Figure 16:
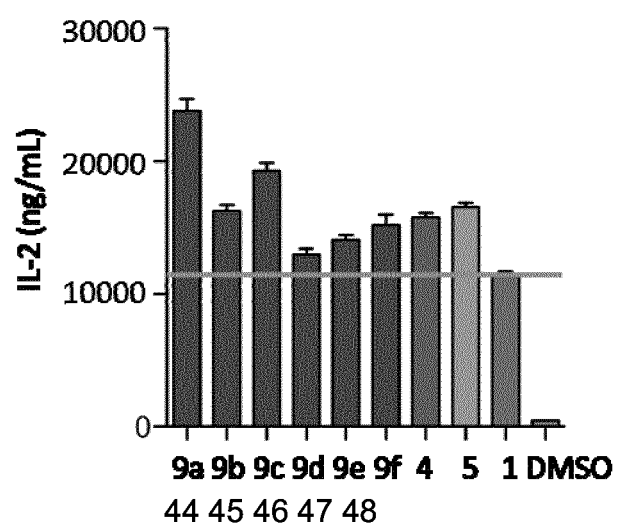
FIG. 16 shows data of IL-2 release of triazolyl-containing galactopyranosyl compounds of the present invention are compared with known α-GalCer compounds.

In order to assess the antigenic activity of the triazolyl-containing galactopyranosyl compounds of example 10, bone marrow dendritic cells (BMDC) were loaded during 20 hours with 100 ng/mL glycolipid. After 16 hours of co-culture with 2C12 cells (iNKT cell hybridoma), IL-2 secretion was determined by ELISA. Compounds 44-48 showed an efficacy to release IL-2 that was higher than or comparable to α-GalCer (FIG. 16). Compounds in which a butyl (44) or phenyl (45) substituent is directly attached to the triazolyl ring tend to induce the highest IL-2 secretion. Hence we demonstrate that the mere presence of a triazol-1-yl ring at position 6" suffices to cause a superior antigenic activity than α-GalCer. Dendritic cells (DCs) loaded with the non-substituted triazolyl compound were even better in stimulating iNKT cells to release IL-2. These data also indicate that a 1,4-substitution of the triazolyl moiety does not interfere in the interaction with CD1d and the TCR, provided that the attached group does not exceed a certain size.

EXAMPLE 12

Characterization of Ternary Complexes of Carbamate-containing Galactopyranosyl Compounds with mCD1d and TCR We herein determine the binding mode of the glycolipids PyrC-α-GalCer (3c) and 4ClPhC-α-GalCer (3a).

First, the ternary mCD1d-lipid-mTCR complexes using the glycolipids 4ClPhC-α-GalCer (3a) and PyrC-α-GalCer (3c) were prepared as described previously for NU-α-GalCer, and purified by size exclusion chromatography (SEC) using Superdex S200 10/300 GL (GE Healthcare). Both mCD1d-4ClPhC-α-GalCer-mTCR and mCD1d-PyrC-α-GalCer-mTCR complexes were concentrated to 3.5 mg/ml in SEC buffer (50 mM Hepes, pH 7.5, 150 mM NaCl). Crystals were grown at 22.3° C. by sitting drop vapor diffusion while by mixing 0.5 µl mCD1d-4ClPhC-α-GalCer-mTCR and 0.5 µl precipitate (20% PEG 4000, 0.2 M sodium thiocyanate) or by mixing 1 µl mCD1d-PyrC-α-GalCer-mTCR and 1 pl precipitate (20% PEG 4000, 0.2 M di-ammonium hydrogen citrate), respectively.

Crystals were flash-cooled at 100° K in a mother liquor containing 30% glycerol. Diffraction data from a single crystal were collected at the Stanford Synchrotron Radiation Laboratory beamlines 9-2 (mCD1d-4ClPhC-α-GalCer-mTCR) and 11-1 (mCD1d-PyrC-α-GalCer-mTCR), and were processed with the HKL2000 (25) and iMosflm (26) software to 3.0 Å, and 2.8 Å resolution, respectively. The mCD1d-4ClPhC-α-GalCer-mTCR crystal belongs to orthorhombic space group $C222_1$ with cell parameters a=79.28 Å, b=191.86 Å, and c=151.59 Å. The mCD1d-PyrC-α-GalCer-mTCR crystal also belongs to space group $C222_1$ with cell parameters a=78.97 Å, b=191.40 Å, and c=151.22 Å.

The asymmetric unit contains one mCD1d-glycolipid-TCR molecule with estimated solvent content of 57.3% based on a Matthews' coefficient (Vm) of 2.88 $A^3$/Da for 4ClPhC-α-GalCer and 56.9% (VM) of 2.86 $A^3$/Da for PyrC-α-GalCer. Crystal structures were determined by molecular replacement using MOLREP as part of the CCP4 suite. Protein coordinates from mCD1d-iGB3-mTCR (from Protein Data Bank code 3RZC), as the search model, with the ligand removed, were used for molecular replacement (MR) for mCD1d-PyrC-α-GalCer-mTCR. The protein mCD1d coordinates from the mCD1d-iGB3 structure (from PDB 2Q7Y) and the mouse Vα14Vβ8.2 TCR (from PDB 3QUY) coordinates were used for mCD1d-4ClPhC-α-GalCer-mTCR structure determination by MR. The REFMAC glycolipid libraries, were created using the Dundee ProDRG2 server. After the MR solutions for both crystal structures were obtained, containing both mCD1d and mTCR, the model was rebuilt into $\sigma_A$-weighted $2F_o-F_c$ and $F_o-F_c$ difference electron density maps using the program COOT. Final refinement steps were performed using the translation, libration and screw axis (TLS) procedure in REFMAC with five anisotropic domains (α1-α2 domain of mCD1d, including carbohydrates and glycolipids, α3-domain, β2m, variable domain, and constant domain of mTCR). The mCD1d-PyrC-α-GalCer-mTCR structure has the final $R_{cryst}$=19.13% and $R_{free}$=23.94% and was refined to 2.8 Å, while mCD1d-4ClPhC-α-GalCer-mTCR was refined to 3.00 Å with a final $R_{cryst}$=18.59% and $R_{free}$=22.84%. The high quality of both models was confirmed with the program Molprobity.

Surprisingly, while the binding of both glycolipids is highly similar to that of α-GalCer, neither of the aromatic substitutions of PyrC-α-GalCer and 4ClPhC-α-GalCer insert down into the CD1d binding groove, as has been demonstrated for NU-α-GalCer. Instead, both 6"-OH aromatic substitutions are presented differently above the A' pocket of CD1d. While 4ClPhC-α-GalCer does not induce a structural change in the A' roof of CD1d, it interacts more intimately with CD1d. In contrast, PyrC-α-GalCer is slightly elevated and its pyridine group contacts the TCR. Similar to α-GalCer, the galactose moiety of both glycolipids forms H-bonds with the TCR through the 2"-and 3"-OH groups, while the 4"-OH group looses this contact. It is known that the TCR contact with the 4"-OH group is the key determinant in TCR interaction. However, both PyrC-α-GalCer and 4ClPhC-α-GalCer lost the H-bond (while still making a Van der Waals contact with 3.5-3.8 Å distance) and still have similar binding affinities compared to α-GalCer, suggesting that the 6"-OH modifications compensate in part for the loss of the 4"-OH H-bond with the TCR. Most surprisingly, major Van der Waals interactions were observed between the pyridine of PyrC-α-GalCer and the Gln52 of the TCR. The pyridine moiety makes intimate contacts with Gln52 (distance 3.3-3.5 Å) compared to 6.4-6.9 Å for the 4Cl-phenyl group (4ClPhC-α-GalCer). As a result, the TCR exhibits many more interaction with PyrC-α-GalCer than with 4ClPhC-α-GalCer, leading to high affinity TCR binding. Even though the pyridine ring forms extra contacts with Gln52 of the TCR, the binding affinity does not exceed the binding affinity of mTCR to α-GalCer-CD1d, likely as it lacks the important H-bond with between the 4"-OH of galactose and Asn30 of the TCR. Interestingly, the additional glycolipid contact with TCR residue Gln52 has previously not been seen in any other structure. Therefore, our data provide a structural framework for the design of novel compounds that target Gln52 to increase TCR contacts.

Binding of 4ClPhC-α-GalCer (3a) and PyrC-α-GalCer (3c) to CD1d equals that of α-GalCer. All the H-bond interactions between the 2"-OH (with Asp153) and 3"-OH (with Asp153) of the glycolipid galactose and the 3-OH (with Asp80), 4-OH (with Asp 80) of the glycolipid ceramide backbone with CD1d residues are conserved. Carbamate linked aromatic groups of 4ClPhC-α-GalCer and PyrC-α-GalCer, however, do not form the extra H-bond interactions between the carbonyl oxygen of the urea linker that connects the galactose and the naphthyl moieties with Thr159 of CD1d as shown in NU-α-GalCer. Thus the carbamate linker results in a more flexible presentation of the substituents as well as a less tight interaction of the linker itself with CD1d, explaining the slightly less well ordered electron density for the glycolipid 6"-OH modification, versus NU-α-GalCer. Analysis of the buried surface areas (a measure of the extent to which two molecules contact each other) between the glycolipids and CD1d indicates that 4ClPhC-α-GalCer binds as extensively to CD1d as NU-α-GalCer (1,124 vs. 1146 $Å^2$), correlating with their enhanced CD1d-stability, while PyrC-α-GalCer (1,045$Å^2$) and α-GalCer (1,027 $Å^2$) interact less extensively with CD1d. PyrC-α-GalCer, however, interacts more with the TCR α-chain (199.2 $Å^2$ vs. 137.1-155.7 $Å^2$) and also shows an increased stability when bound to CD1d. The increased contacts of 4ClPhC-α-GalCer (3a) are mostly the result of novel or increased Van der Waals interactions with CD1d residues including Met69, Met162 and more importantly, Thr159. Glycolipid contacts with Thr159 are not formed when α-GalCer or PyrC-α-GalCer (3c) bind to CD1d.

As a result, we observe two different glycolipid binding modes compared to α-GalCer: glycolipids that form increased contacts with CD1d (4ClPhC-α-GalCer) and glycolipids that form increased contacts with the TCR (PyrC-α-GalCer). In addition, our data suggest that the tested 6"-OH modified α-GalCer compounds generally exhibit increased stability when loaded on CD1d, even in the absence of additional molecular contacts with CD1d. In addition, our data show that the stability of the CD1d-carbamate glycolipid complexes is much higher than that of α-GalCer, suggesting a role of the aromatic 6"-OH modification for the overall CD1d-glycolipid stability.

Comparison of the presentation of both carbamate-linked, aromatic substitutions reveals the paucity of binding orientations that are adopted by the different chemical groups. By forming intimate contacts with the TCR (PyrC-α-GalCer), the aromatic groups bridge about 11 Å between the CD1d and TCR interface with the capacity to induce structural changes within CD1d, depending on the composition of the linker and aromatic substitution.

As a conclusion, the observed enlargement of the TCR footprint may contribute to an enhanced stability of the trimolecular complex and thus higher cytokine production. This previously unknown flexibility of the NKTCR footprint opens new avenues for such novel Th1 polarizing glycolipids with therapeutical potential in cancer treatment.

The invention claimed is:

1. A carbamate-containing galactopyranosyl compound represented by the structural formula (I):

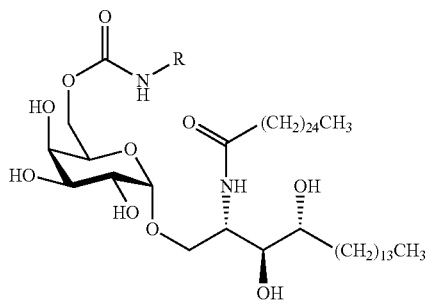

wherein R is selected from the group consisting of $C_{1-8}$ alkyl, $C_{3-10}$ cycloalkyl, aryl-$C_{1-4}$ alkyl, heterocyclyl-$C_{1-4}$ alkyl, cycloalkyl-$C_{1-4}$ alkyl, aryl and heterocyclyl; and wherein each of the $(CH_2)_{24}CH_3$ and $(CH_2)_{13}CH_3$ groups may independently be replaced with a $C_{6-30}$ alkyl group, and wherein each hydroxyl group on the pyranosyl ring or the lipid chain may independently be replaced with a hydroxyl-protecting group; or a corresponding thiocarbamate-containing galactopyranosyl compound wherein a thiocarbamate group C(=S)NHR replaces the carbamate group C(=O)NHR shown in structural formula (I), or a pharmaceutically acceptable salt thereof.

2. A carbamate-containing galactopyranosyl compound according to claim 1, wherein R is selected from the group consisting of 4-chlorophenyl, naphth-1-yl, and 4-pyridyl.

3. A carbamate-containing galactopyranosyl compound according to claim 1, wherein R is not 4-chlorophenyl, naphth-1-yl or 4-pyridyl.

4. A carbamate-containing or thiocarbamate-containing galacto-pyranosyl compound represented by the structural formula (II):

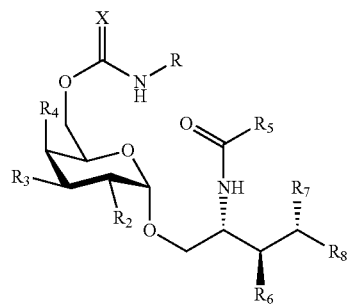

wherein:
X is O or S,
R is selected from the group consisting of selected from the group consisting of $C_{1-8}$ alkyl, $C_{3-10}$ cycloalkyl, aryl-$C_{1-4}$ alkyl, heterocyclyl-$C_{1-4}$ alkyl, cycloalkyl-$C_{1-4}$ alkyl, aryl and heterocyclyl, wherein R is optionally substituted with one or more $R_9$;
$R_2$, $R_3$, $R_4$, $R_6$ and $R_7$ are independently selected from the group consisting of hydroxyl and protected hydroxyl groups;
$R_5$ is selected from the group consisting $C_{6-30}$ alkyl and arylalkyl;
$R_8$ is $C_{6-30}$ alkyl; and
each $R_9$ is independently selected from the group consisting of halogen, hydroxy, trifluoromethyl, trifluoromethoxy, $C_{1-8}$ alkoxy, $C_{1-6}$ alkyl, cyano, methylthio, phenyl, phenoxy, chloromethyl, dichloromethyl, chloro-difluoromethyl, acetyl, nitro, benzyl, heterocyclyl and di-$C_{1-4}$ alkyl-amino, or a pharmaceutically acceptable salt thereof.

5. A carbamate-containing or thiocarbamate-containing galactopyranosyl compound according to claim 4, wherein $R_2$, $R_3$, $R_4$, $R_6$ and $R_7$ are benzyloxy.

6. A carbamate-containing or thiocarbamate-containing galactopyranosyl compound according to claim 4, wherein R is phenyl substituted with one, two or three $R_9$.

7. A carbamate-containing or thiocarbamate-containing galactopyranosyl compound according to claim 6, wherein one $R_9$ is a para-substituent, a meta-substituent or an ortho-substituent.

8. A carbamate-containing or thiocarbamate-containing galactopyranosyl compound according to claim 4, wherein R is selected from the group consisting of pyrid-4-yl, pyrid-3-yl, pyrid-2-yl, pyrazinyl, pyrimidin-2-yl, pyrimidin-4-yl, pyrimidin-5-yl and pyrimidin-6-yl, naphth-1-yl and naphth-2-yl.

9. A pharmaceutical composition comprising a therapeutically effective amount of a galactopyranosyl compound according to claim 1, and one or more pharmaceutically acceptable excipients.

10. A pharmaceutical composition comprising a therapeutically effective amount of a galactopyranosyl compound according to claim 4, and one or more pharmaceutically acceptable excipients.

11. A method of treatment of a disorder in a mammal, the said method comprising administering an effective amount of a galactopyranosyl compound according to claim 1 to the mammal in need thereof, said disorder being selected from the group consisting of cell proliferative disorders, immune disorders, auto-immune disorders, and infectious diseases.

12. A method of treatment of a disorder in a mammal, the said method comprising administering an effective amount of a galactopyranosyl compound according to claim 4 to the mammal in need thereof, said disorder being selected from the group consisting of cell proliferative disorders, immune disorders, auto-immune disorders, and infectious diseases.

13. An immune adjuvant to improve the efficiency of a vaccine against a human tumor or an infectious disease, comprising a galactopyranosyl compound according to claim 1.

14. An immune adjuvant to improve the efficiency of a vaccine against a human tumor or an infectious disease, comprising a galactopyranosyl compound according to claim 4.

* * * * *